(12) United States Patent
Davalos et al.

(10) Patent No.: US 10,694,972 B2
(45) Date of Patent: Jun. 30, 2020

(54) DEVICES, SYSTEMS, AND METHODS FOR REAL-TIME MONITORING OF ELECTROPHYSICAL EFFECTS DURING TISSUE TREATMENT

(71) Applicant: Virginia Tech Intellectual Properties, Inc., Blacksburg, VA (US)

(72) Inventors: Rafael V. Davalos, Blacksburg, VA (US); Mohammad Bonakdar, Blacksburg, VA (US); Eduardo L. Latouche, Blacksburg, VA (US); Roop L. Mahajan, Blacksburg, VA (US); John L. Robertson, Blacksburg, VA (US); Christopher B. Arena, Blacksburg, VA (US); Michael B. Sano, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 19 days.

(21) Appl. No.: 15/536,333

(22) PCT Filed: Dec. 15, 2015

(86) PCT No.: PCT/US2015/065792
§ 371 (c)(1),
(2) Date: Jun. 15, 2017

(87) PCT Pub. No.: WO2016/100325
PCT Pub. Date: Jun. 23, 2016

(65) Prior Publication Data
US 2017/0360326 A1    Dec. 21, 2017

Related U.S. Application Data

(60) Provisional application No. 62/091,703, filed on Dec. 15, 2014.

(51) Int. Cl.
*A61B 5/053* (2006.01)
*A61B 5/01* (2006.01)
*G01N 33/543* (2006.01)

(52) U.S. Cl.
CPC .............. *A61B 5/0538* (2013.01); *A61B 5/01* (2013.01); *G01N 33/5438* (2013.01)

(58) Field of Classification Search
CPC ..... A61B 5/0538; A61B 5/01; G01N 33/5438
See application file for complete search history.

(56) References Cited

U.S. PATENT DOCUMENTS

| 1,653,819 A | 12/1927 | Ephraim |
| 3,730,238 A | 5/1973 | Butler |

(Continued)

FOREIGN PATENT DOCUMENTS

| AU | 2002315095 A1 | 12/2002 |
| AU | 2003227960 A1 | 12/2003 |

(Continued)

OTHER PUBLICATIONS

International Search Report for PCT/US2015/065792 dated Feb. 9, 2016.

(Continued)

*Primary Examiner* — Christine H Matthews
*Assistant Examiner* — Joshua Daryl D Lannu
(74) *Attorney, Agent, or Firm* — New River Valley IP Law, P.C.; Michele L. Mayberry

(57) ABSTRACT

Provided herein are devices, systems, and methods for monitoring lesion or treated area in a tissue during focal ablation or cell membrane disruption therapy. Provided herein are embodiments of an electrical conductivity sensor having an impedance sensor, where the impedance sensor can be configured to measure a low-frequency and a high-frequency impedance and a substrate, where the impedance (Continued)

sensor is coupled to the substrate. The substrate can be flexible. In embodiments, the impedance sensor can contain two or more electrical conductors. The electrical conductors can be in a bipolar configuration. The electrical conductors can be in a tetrapolar configuration. In embodiments, the electrical conductivity sensor can have two impedance sensors that can be coupled to the substrate such that they are orthogonal to each other.

17 Claims, 25 Drawing Sheets

(56) References Cited

U.S. PATENT DOCUMENTS

| | | | |
|---|---|---|---|
| 3,746,004 | A | 7/1973 | Jankelson |
| 3,871,359 | A | 3/1975 | Pacela |
| 4,016,886 | A | 4/1977 | Doss et al. |
| 4,037,341 | A | 7/1977 | Odle et al. |
| 4,216,860 | A | 8/1980 | Heimann |
| 4,226,246 | A | 10/1980 | Fragnet |
| 4,262,672 | A | 4/1981 | Kief |
| 4,267,047 | A | 5/1981 | Henne et al. |
| 4,278,092 | A | 7/1981 | Borsanyi et al. |
| 4,299,217 | A | 11/1981 | Sagae et al. |
| 4,311,148 | A | 1/1982 | Courtney et al. |
| 4,336,881 | A | 6/1982 | Babb et al. |
| 4,344,436 | A | 8/1982 | Kubota |
| 4,392,855 | A | 7/1983 | Oreopoulos et al. |
| 4,406,827 | A | 9/1983 | Carim |
| 4,407,943 | A | 10/1983 | Cole et al. |
| 4,416,276 | A | 11/1983 | Newton et al. |
| 4,447,235 | A | 5/1984 | Clarke |
| 4,469,098 | A | 9/1984 | Davi |
| 4,489,535 | A | 12/1984 | Veltman |
| 4,512,765 | A | 4/1985 | Muto |
| 4,580,572 | A | 4/1986 | Granek et al. |
| 4,636,199 | A | 1/1987 | Victor |
| 4,672,969 | A | 6/1987 | Dew |
| 4,676,258 | A | 6/1987 | Inokuchi et al. |
| 4,676,782 | A | 6/1987 | Yamamoto et al. |
| 4,687,471 | A | 8/1987 | Twardowski et al. |
| 4,716,896 | A | 1/1988 | Ackerman |
| 4,723,549 | A | 2/1988 | Wholey et al. |
| D294,519 | S | 3/1988 | Hardy |
| 4,756,838 | A | 7/1988 | Veltman |
| 4,772,269 | A | 9/1988 | Twardowski et al. |
| 4,798,585 | A | 1/1989 | Inoue et al. |
| 4,810,963 | A | 3/1989 | Blake-Coleman et al. |
| 4,813,929 | A | 3/1989 | Semrad |
| 4,819,637 | A | 4/1989 | Dormandy et al. |
| 4,822,470 | A | 4/1989 | Chang |
| 4,836,204 | A | 6/1989 | Landymore et al. |
| 4,840,172 | A | 6/1989 | Augustine et al. |
| 4,863,426 | A | 9/1989 | Ferragamo et al. |
| 4,885,003 | A | 12/1989 | Hillstead |
| 4,886,496 | A | 12/1989 | Conoscenti et al. |
| 4,886,502 | A | 12/1989 | Poirier et al. |
| 4,889,634 | A | 12/1989 | El-Rashidy |
| 4,907,601 | A | 3/1990 | Frick |
| 4,919,148 | A | 4/1990 | Muccio |
| 4,920,978 | A | 5/1990 | Colvin |
| 4,921,484 | A | 5/1990 | Hillstead |
| 4,946,793 | A | 8/1990 | Marshall, III |
| 4,976,709 | A | 12/1990 | Sand |
| 4,981,477 | A | 1/1991 | Schon et al. |
| 4,986,810 | A | 1/1991 | Semrad |
| 4,987,895 | A | 1/1991 | Heimlich |
| 5,019,034 | A | 5/1991 | Weaver et al. |
| 5,031,775 | A | 7/1991 | Kane |
| 5,052,391 | A | 10/1991 | Silberstone et al. |
| 5,053,013 | A | 10/1991 | Ensminger et al. |
| 5,058,605 | A | 10/1991 | Slovak |
| 5,071,558 | A | 12/1991 | Itoh |
| 5,098,843 | A | 3/1992 | Calvin |
| 5,122,137 | A | 6/1992 | Lennox |
| 5,134,070 | A | 7/1992 | Casnig |
| 5,137,517 | A | 8/1992 | Loney et al. |
| 5,141,499 | A | 8/1992 | Zappacosta |
| D329,496 | S | 9/1992 | Wotton |
| 5,156,597 | A | 10/1992 | Verreet et al. |
| 5,173,158 | A | 12/1992 | Schmukler |
| 5,186,715 | A | 2/1993 | Phillips et al. |
| 5,186,800 | A | 2/1993 | Dower |
| 5,188,592 | A | 2/1993 | Hakki |
| 5,190,541 | A | 3/1993 | Abele et al. |
| 5,192,312 | A | 3/1993 | Orton |
| 5,193,537 | A | 3/1993 | Freeman |
| 5,209,723 | A | 5/1993 | Twardowski et al. |
| 5,215,530 | A | 6/1993 | Hogan |
| 5,224,933 | A | 7/1993 | Bromander |
| 5,227,730 | A | 7/1993 | King et al. |
| 5,242,415 | A | 9/1993 | Kantrowitz et al. |
| 5,273,525 | A | 12/1993 | Hofmann |
| D343,687 | S | 1/1994 | Houghton et al. |
| 5,277,201 | A | 1/1994 | Stern |
| 5,279,564 | A | 1/1994 | Taylor |
| 5,281,213 | A | 1/1994 | Milder |
| 5,283,194 | A | 2/1994 | Schmukler |
| 5,290,263 | A | 3/1994 | Wigness et al. |
| 5,308,325 | A | 5/1994 | Quinn et al. |
| 5,308,338 | A | 5/1994 | Helfrich |
| 5,318,543 | A | 6/1994 | Ross et al. |
| 5,318,563 | A | 6/1994 | Malis et al. |
| 5,328,451 | A | 7/1994 | Davis et al. |
| 5,334,167 | A | 8/1994 | Cocanower |
| 5,348,554 | A | 9/1994 | Imran et al. |
| D351,661 | S | 10/1994 | Fischer |
| 5,383,917 | A | 1/1995 | Desai et al. |
| 5,389,069 | A | 2/1995 | Weaver |
| 5,391,158 | A | 2/1995 | Peters |
| 5,403,311 | A | 4/1995 | Abele et al. |
| 5,405,320 | A | 4/1995 | Twardowski et al. |
| 5,425,752 | A | 6/1995 | Vu Nguyen |
| 5,439,440 | A | 8/1995 | Hofmann |
| 5,458,625 | A | 10/1995 | Kendall |
| 5,484,400 | A | 1/1996 | Edwards et al. |
| 5,484,401 | A | 1/1996 | Rodriguez et al. |
| 5,533,999 | A | 7/1996 | Hood et al. |
| 5,536,240 | A | 7/1996 | Edwards et al. |
| 5,536,267 | A | 7/1996 | Edwards et al. |
| 5,540,737 | A | 7/1996 | Fenn |
| 5,546,940 | A | 8/1996 | Panescu et al. |
| 5,562,720 | A | 10/1996 | Stern et al. |
| 5,575,811 | A | 11/1996 | Reid et al. |
| D376,652 | S | 12/1996 | Hunt et al. |
| 5,582,588 | A | 12/1996 | Sakurai et al. |
| 5,586,982 | A | 12/1996 | Abela |
| 5,588,424 | A | 12/1996 | Insler et al. |
| 5,588,960 | A | 12/1996 | Edwards et al. |
| 5,599,294 | A | 2/1997 | Edwards et al. |
| 5,599,311 | A | 2/1997 | Raulerson |
| 5,616,126 | A | 4/1997 | Malekmehr et al. |
| 5,620,479 | A | 4/1997 | Diederich |
| 5,626,146 | A | 5/1997 | Barber et al. |
| D380,272 | S | 6/1997 | Partika et al. |
| 5,634,899 | A | 6/1997 | Shapland et al. |
| 5,643,197 | A | 7/1997 | Brucker et al. |
| 5,645,855 | A | 7/1997 | Lorenz |
| 5,672,173 | A | 9/1997 | Gough et al. |
| 5,674,267 | A | 10/1997 | Mir et al. |
| 5,683,384 | A | 11/1997 | Gough et al. |
| 5,687,723 | A | 11/1997 | Avitall |
| 5,690,620 | A | 11/1997 | Knott |
| 5,697,905 | A | 12/1997 | d'Ambrosio |
| 5,700,252 | A | 12/1997 | Klingenstein |
| 5,702,359 | A | 12/1997 | Hofmann et al. |
| 5,718,246 | A | 2/1998 | Vona |
| 5,720,921 | A | 2/1998 | Meserol |
| 5,735,847 | A | 4/1998 | Gough et al. |
| 5,752,939 | A | 5/1998 | Makoto |
| 5,778,894 | A | 7/1998 | Dorogi et al. |
| 5,782,882 | A | 7/1998 | Lerman et al. |

(56) References Cited

U.S. PATENT DOCUMENTS

| | | |
|---|---|---|
| 5,800,378 A | 9/1998 | Edwards et al. |
| 5,800,484 A | 9/1998 | Gough et al. |
| 5,807,272 A | 9/1998 | Kun et al. |
| 5,807,306 A | 9/1998 | Shapland et al. |
| 5,807,395 A | 9/1998 | Mulier et al. |
| 5,810,742 A | 9/1998 | Pearlman |
| 5,810,762 A | 9/1998 | Hofmann |
| 5,830,184 A | 11/1998 | Basta |
| 5,836,897 A | 11/1998 | Sakurai et al. |
| 5,836,905 A | 11/1998 | Lemelson et al. |
| 5,843,026 A | 12/1998 | Edwards et al. |
| 5,843,182 A | 12/1998 | Goldstein |
| 5,865,787 A | 2/1999 | Shapland et al. |
| 5,868,708 A | 2/1999 | Hart et al. |
| 5,873,849 A | 2/1999 | Bernard |
| 5,904,648 A | 5/1999 | Arndt et al. |
| 5,919,142 A | 7/1999 | Boone et al. |
| 5,919,191 A | 7/1999 | Lennox et al. |
| 5,921,982 A | 7/1999 | Lesh et al. |
| 5,944,710 A | 8/1999 | Dev et al. |
| 5,947,284 A | 9/1999 | Foster |
| 5,947,889 A | 9/1999 | Hehrlein |
| 5,951,546 A | 9/1999 | Lorentzen |
| 5,954,745 A | 9/1999 | Gertler et al. |
| 5,957,919 A | 9/1999 | Laufer |
| 5,957,963 A | 9/1999 | Dobak |
| 5,968,006 A | 10/1999 | Hofmann |
| 5,983,131 A | 11/1999 | Weaver et al. |
| 5,984,896 A | 11/1999 | Boyd |
| 5,991,697 A | 11/1999 | Nelson et al. |
| 5,999,847 A | 12/1999 | Elstrom |
| 6,004,339 A | 12/1999 | Wijay |
| 6,009,347 A | 12/1999 | Hofmann |
| 6,009,877 A | 1/2000 | Edwards |
| 6,010,613 A | 1/2000 | Walters et al. |
| 6,016,452 A | 1/2000 | Kasevich |
| 6,029,090 A | 2/2000 | Herbst |
| 6,041,252 A | 3/2000 | Walker et al. |
| 6,043,066 A | 3/2000 | Mangano et al. |
| 6,050,994 A | 4/2000 | Sherman |
| 6,055,453 A | 4/2000 | Hofmann et al. |
| 6,059,780 A | 5/2000 | Gough et al. |
| 6,066,134 A | 5/2000 | Eggers et al. |
| 6,068,121 A | 5/2000 | McGlinch |
| 6,068,650 A | 5/2000 | Hofmann et al. |
| 6,071,281 A | 6/2000 | Burnside et al. |
| 6,074,374 A | 6/2000 | Fulton |
| 6,074,389 A | 6/2000 | Levine et al. |
| 6,085,115 A | 7/2000 | Weaver et al. |
| 6,090,016 A | 7/2000 | Kuo |
| 6,090,105 A | 7/2000 | Zepeda et al. |
| 6,090,106 A | 7/2000 | Goble et al. |
| D430,015 S | 8/2000 | Himbert et al. |
| 6,096,035 A | 8/2000 | Sodhi et al. |
| 6,102,885 A | 8/2000 | Bass |
| 6,106,521 A | 8/2000 | Blewett et al. |
| 6,109,270 A | 8/2000 | Mah et al. |
| 6,110,192 A | 8/2000 | Ravenscroft et al. |
| 6,113,593 A | 9/2000 | Tu et al. |
| 6,116,330 A | 9/2000 | Salyer |
| 6,120,493 A | 9/2000 | Hofmann |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,139,545 A | 10/2000 | Utley et al. |
| 6,150,148 A | 11/2000 | Nanda et al. |
| 6,159,163 A | 12/2000 | Strauss et al. |
| 6,178,354 B1 | 1/2001 | Gibson |
| D437,941 S | 2/2001 | Frattini |
| 6,193,715 B1 | 2/2001 | Wrublewski et al. |
| 6,198,970 B1 | 3/2001 | Freed et al. |
| 6,200,314 B1 | 3/2001 | Sherman |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann et al. |
| 6,219,577 B1 | 4/2001 | Brown, III et al. |
| D442,697 S | 5/2001 | Hajianpour |
| 6,233,490 B1 | 5/2001 | Kasevich |
| 6,235,023 B1 | 5/2001 | Lee et al. |
| D443,360 S | 6/2001 | Haberland |
| 6,241,702 B1 | 6/2001 | Lundquist et al. |
| 6,241,725 B1 | 6/2001 | Cosman |
| D445,198 S | 7/2001 | Frattini |
| 6,258,100 B1 | 7/2001 | Alferness et al. |
| 6,261,831 B1 | 7/2001 | Agee |
| 6,277,114 B1 | 8/2001 | Bullivant et al. |
| 6,278,895 B1 | 8/2001 | Bernard |
| 6,280,441 B1 | 8/2001 | Ryan |
| 6,283,988 B1 | 9/2001 | Laufer et al. |
| 6,283,989 B1 | 9/2001 | Laufer et al. |
| 6,284,140 B1 | 9/2001 | Sommermeyer et al. |
| 6,287,293 B1 | 9/2001 | Jones et al. |
| 6,287,304 B1 | 9/2001 | Eggers et al. |
| 6,296,636 B1 | 10/2001 | Cheng et al. |
| 6,298,726 B1 | 10/2001 | Adachi et al. |
| 6,299,633 B1 | 10/2001 | Laufer |
| 6,300,108 B1 | 10/2001 | Rubinsky et al. |
| D450,391 S | 11/2001 | Hunt et al. |
| 6,312,428 B1 | 11/2001 | Eggers et al. |
| 6,326,177 B1 | 12/2001 | Schoenbach et al. |
| 6,327,505 B1 | 12/2001 | Medhkour et al. |
| 6,328,689 B1 | 12/2001 | Gonzalez et al. |
| 6,347,247 B1 | 2/2002 | Dev et al. |
| 6,349,233 B1 | 2/2002 | Adams |
| 6,351,674 B2 | 2/2002 | Silverstone |
| 6,375,634 B1 | 4/2002 | Carroll |
| 6,387,671 B1 | 5/2002 | Rubinsky et al. |
| 6,398,779 B1 | 6/2002 | Buysse et al. |
| 6,403,348 B1 | 6/2002 | Rubinsky et al. |
| 6,405,732 B1 | 6/2002 | Edwards et al. |
| 6,411,852 B1 | 6/2002 | Danek et al. |
| 6,419,674 B1 | 7/2002 | Bowser et al. |
| 6,428,802 B1 | 8/2002 | Atala |
| 6,437,551 B1 | 8/2002 | Krulevitch et al. |
| 6,443,952 B1 | 9/2002 | Mulier et al. |
| 6,463,331 B1 | 10/2002 | Edwards |
| 6,470,211 B1 | 10/2002 | Ideker et al. |
| 6,482,221 B1 | 11/2002 | Hebert et al. |
| 6,482,619 B1 | 11/2002 | Rubinsky et al. |
| 6,485,487 B1 | 11/2002 | Sherman |
| 6,488,673 B1 | 12/2002 | Laufer et al. |
| 6,488,678 B2 | 12/2002 | Sherman |
| 6,488,680 B1 | 12/2002 | Francischelli et al. |
| 6,491,706 B1 | 12/2002 | Alferness et al. |
| 6,493,589 B1 | 12/2002 | Medhkour et al. |
| 6,493,592 B1 | 12/2002 | Leonard et al. |
| 6,500,173 B2 | 12/2002 | Underwood et al. |
| 6,503,248 B1 | 1/2003 | Levine |
| 6,506,189 B1 | 1/2003 | Rittman et al. |
| 6,514,248 B1 | 2/2003 | Eggers et al. |
| 6,520,183 B2 | 2/2003 | Amar |
| 6,526,320 B2 | 2/2003 | Mitchell |
| D471,640 S | 3/2003 | McMichael et al. |
| D471,641 S | 3/2003 | McMichael et al. |
| 6,530,922 B2 | 3/2003 | Cosman et al. |
| 6,533,784 B2 | 3/2003 | Truckai et al. |
| 6,537,976 B1 | 3/2003 | Gupta |
| 6,540,695 B1 | 4/2003 | Burbank et al. |
| 6,558,378 B2 | 5/2003 | Sherman et al. |
| 6,562,604 B2 | 5/2003 | Rubinsky et al. |
| 6,569,162 B2 | 5/2003 | He |
| 6,575,969 B1 | 6/2003 | Rittman et al. |
| 6,589,161 B2 | 7/2003 | Corcoran |
| 6,592,594 B2 | 7/2003 | Rimbaugh et al. |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | Mccormick et al. |
| 6,616,657 B2 | 9/2003 | Simpson et al. |
| 6,627,421 B1 | 9/2003 | Unger et al. |
| D480,816 S | 10/2003 | McMichael et al. |

(56) References Cited

U.S. PATENT DOCUMENTS

| | | |
|---|---|---|
| 6,634,363 B1 | 10/2003 | Danek et al. |
| 6,638,253 B2 | 10/2003 | Breznock |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,689,096 B1 | 2/2004 | Loubens et al. |
| 6,692,493 B2 | 2/2004 | Mcgovern et al. |
| 6,694,979 B2 | 2/2004 | Deem et al. |
| 6,694,984 B2 | 2/2004 | Habib |
| 6,695,861 B1 | 2/2004 | Rosenberg et al. |
| 6,697,669 B2 | 2/2004 | Dev et al. |
| 6,697,670 B2 | 2/2004 | Chomenky et al. |
| 6,702,808 B1 | 3/2004 | Kreindel |
| 6,712,811 B2 | 3/2004 | Underwood et al. |
| D489,973 S | 5/2004 | Root et al. |
| 6,753,171 B2 | 6/2004 | Karube et al. |
| 6,761,716 B2 | 7/2004 | Kadhiresan et al. |
| D495,807 S | 9/2004 | Agbodoe et al. |
| 6,795,728 B2 | 9/2004 | Chornenky et al. |
| 6,801,804 B2 | 10/2004 | Miller et al. |
| 6,812,204 B1 | 11/2004 | McHale et al. |
| 6,837,886 B2 | 1/2005 | Collins et al. |
| 6,847,848 B2 | 1/2005 | Sterzer et al. |
| 6,860,847 B2 | 3/2005 | Alferness et al. |
| 6,865,416 B2 | 3/2005 | Dev et al. |
| 6,881,213 B2 | 4/2005 | Ryan et al. |
| 6,892,099 B2 | 5/2005 | Jaafar et al. |
| 6,895,267 B2 | 5/2005 | Panescu et al. |
| 6,905,480 B2 | 6/2005 | James F Mcguckin et al. |
| 6,912,417 B1 | 6/2005 | Bernard et al. |
| 6,927,049 B2 | 8/2005 | Rubinsky et al. |
| 6,941,950 B2 | 9/2005 | Wilson et al. |
| 6,942,681 B2 | 9/2005 | Johnson |
| 6,958,062 B1 | 10/2005 | Gough et al. |
| 6,960,189 B2 | 11/2005 | Bates et al. |
| 6,962,587 B2 | 11/2005 | Johnson et al. |
| 6,972,013 B1 | 12/2005 | Zhang et al. |
| 6,972,014 B2 | 12/2005 | Eum et al. |
| 6,989,010 B2 | 1/2006 | Francischelli et al. |
| 6,994,689 B1 | 2/2006 | Zadno-Azizi et al. |
| 6,994,706 B2 | 2/2006 | Chornenky et al. |
| 7,011,094 B2 | 3/2006 | Rapacki et al. |
| 7,012,061 B1 | 3/2006 | Reiss et al. |
| 7,027,869 B2 | 4/2006 | Danek et al. |
| 7,036,510 B2 | 5/2006 | Zgoda et al. |
| 7,053,063 B2 | 5/2006 | Rubinsky et al. |
| 7,054,685 B2 | 5/2006 | Dimmer et al. |
| 7,063,698 B2 | 6/2006 | Whayne et al. |
| 7,087,040 B2 | 8/2006 | McGuckin et al. |
| 7,097,612 B2 | 8/2006 | Bertolero et al. |
| 7,100,616 B2 | 9/2006 | Springmeyer |
| 7,113,821 B1 | 9/2006 | Sun et al. |
| 7,130,697 B2 | 10/2006 | Chomenky et al. |
| 7,211,083 B2 | 5/2007 | Chomenky et al. |
| 7,232,437 B2 | 6/2007 | Berman et al. |
| 7,250,048 B2 | 7/2007 | Francischelli et al. |
| D549,332 S | 8/2007 | Matsumoto et al. |
| 7,257,450 B2 | 8/2007 | Auth et al. |
| 7,264,002 B2 | 9/2007 | Danek et al. |
| 7,267,676 B2 | 9/2007 | Chomenky et al. |
| 7,273,055 B2 | 9/2007 | Danek et al. |
| 7,291,146 B2 | 11/2007 | Steinke et al. |
| 7,331,940 B2 | 2/2008 | Sommerich |
| 7,331,949 B2 | 2/2008 | Marisi |
| 7,341,558 B2 | 3/2008 | Torre et al. |
| 7,344,533 B2 | 3/2008 | Pearson et al. |
| D565,743 S | 4/2008 | Phillips et al. |
| D571,478 S | 6/2008 | Horacek |
| 7,387,626 B2 | 6/2008 | Edwards et al. |
| 7,399,747 B1 | 7/2008 | Clair et al. |
| D575,399 S | 8/2008 | Matsumoto et al. |
| D575,402 S | 8/2008 | Sandor |
| 7,419,487 B2 | 9/2008 | Johnson et al. |
| 7,434,578 B2 | 10/2008 | Dillard et al. |
| 7,449,019 B2 | 11/2008 | Uchida et al. |
| 7,451,765 B2 | 11/2008 | Adler |
| 7,455,675 B2 | 11/2008 | Schur et al. |
| 7,476,203 B2 | 1/2009 | DeVore et al. |
| 7,520,877 B2 | 4/2009 | Lee et al. |
| 7,533,671 B2 | 5/2009 | Gonzalez et al. |
| D595,422 S | 6/2009 | Mustapha |
| 7,544,301 B2 | 6/2009 | Shah et al. |
| 7,549,984 B2 | 6/2009 | Mathis |
| 7,565,208 B2 | 7/2009 | Harris et al. |
| 7,571,729 B2 | 8/2009 | Saadat et al. |
| 7,632,291 B2 | 12/2009 | Stephens et al. |
| 7,655,004 B2 | 2/2010 | Long |
| 7,674,249 B2 | 3/2010 | Ivorra et al. |
| 7,680,543 B2 | 3/2010 | Azure |
| D613,418 S | 4/2010 | Ryan et al. |
| 7,718,409 B2 | 5/2010 | Rubinsky et al. |
| 7,722,606 B2 | 5/2010 | Azure |
| 7,742,795 B2 | 6/2010 | Stone et al. |
| 7,765,010 B2 | 7/2010 | Chornenky et al. |
| 7,771,401 B2 | 8/2010 | Hekmat et al. |
| RE42,016 E | 12/2010 | Chomenky et al. |
| D630,321 S | 1/2011 | Hamilton |
| D631,154 S | 1/2011 | Hamilton |
| RE42,277 E | 4/2011 | Jaafar et al. |
| 7,918,852 B2 | 4/2011 | Tullis et al. |
| 7,937,143 B2 | 5/2011 | Demarais et al. |
| 7,938,824 B2 | 5/2011 | Chornenky et al. |
| 7,951,582 B2 | 5/2011 | Gazit et al. |
| 7,955,827 B2 | 6/2011 | Rubinsky et al. |
| RE42,835 E | 10/2011 | Chomenky et al. |
| D647,628 S | 10/2011 | Helfteren |
| 8,048,067 B2 | 11/2011 | Davalos et al. |
| RE43,009 E | 12/2011 | Chomenky et al. |
| 8,109,926 B2 | 2/2012 | Azure |
| 8,114,070 B2 | 2/2012 | Rubinsky et al. |
| 8,162,918 B2 | 4/2012 | Ivorra et al. |
| 8,187,269 B2 | 5/2012 | Shadduck et al. |
| 8,221,411 B2 | 7/2012 | Francischelli et al. |
| 8,231,603 B2 | 7/2012 | Hobbs et al. |
| 8,240,468 B2 | 8/2012 | Wilkinson et al. |
| 8,251,986 B2 | 8/2012 | Chomenky et al. |
| 8,267,927 B2 | 9/2012 | Dalal et al. |
| 8,267,936 B2 | 9/2012 | Hushka et al. |
| 8,282,631 B2 | 10/2012 | Davalos et al. |
| 8,298,222 B2 | 10/2012 | Rubinsky et al. |
| 8,348,921 B2 | 1/2013 | Ivorra et al. |
| 8,361,066 B2 | 1/2013 | Long et al. |
| D677,798 S | 3/2013 | Hart et al. |
| 8,425,455 B2 | 4/2013 | Nentwick |
| 8,425,505 B2 | 4/2013 | Long |
| 8,454,594 B2 | 6/2013 | Demarais et al. |
| 8,465,464 B2 | 6/2013 | Travis et al. |
| 8,465,484 B2 | 6/2013 | Davalos et al. |
| 8,511,317 B2 | 8/2013 | Thapliyal et al. |
| 8,518,031 B2 | 8/2013 | Boyden et al. |
| 8,562,588 B2 | 10/2013 | Hobbs et al. |
| 8,603,087 B2 | 12/2013 | Rubinsky et al. |
| 8,632,534 B2 | 1/2014 | Pearson et al. |
| 8,634,929 B2 | 1/2014 | Chomenky et al. |
| 8,647,338 B2 | 2/2014 | Chomenky et al. |
| 8,715,276 B2 | 5/2014 | Thompson et al. |
| 8,753,335 B2 | 6/2014 | Moshe et al. |
| 8,814,860 B2 | 8/2014 | Davalos et al. |
| 8,835,166 B2 | 9/2014 | Phillips et al. |
| 8,845,635 B2 | 9/2014 | Daniel et al. |
| 8,880,195 B2 | 11/2014 | Azure |
| 8,903,488 B2 | 12/2014 | Callas et al. |
| 8,906,006 B2 | 12/2014 | Chomenky et al. |
| 8,926,606 B2 | 1/2015 | Davalos et al. |
| 8,958,888 B2 | 2/2015 | Chomenky et al. |
| 8,968,542 B2 | 3/2015 | Davalos et al. |
| 8,992,517 B2 | 3/2015 | Davalos et al. |
| 9,005,189 B2 | 4/2015 | Davalos et al. |
| 9,078,665 B2 | 7/2015 | Moss et al. |
| 9,149,331 B2 | 10/2015 | Deem et al. |
| 9,173,704 B2 | 11/2015 | Hobbs et al. |
| 9,198,733 B2 | 12/2015 | Neal, II et al. |

(56) References Cited

U.S. PATENT DOCUMENTS

| | | |
|---|---|---|
| 9,283,051 B2 | 3/2016 | Garcia et al. |
| 9,414,881 B2 | 8/2016 | Callas et al. |
| 9,598,691 B2 | 3/2017 | Davalos |
| 9,867,652 B2 | 1/2018 | Sano et al. |
| 10,117,701 B2 | 11/2018 | Davalos et al. |
| 10,117,707 B2 | 11/2018 | Garcia et al. |
| 10,154,874 B2 | 12/2018 | Davalos et al. |
| 10,238,447 B2 | 3/2019 | Neal et al. |
| 10,245,098 B2 | 4/2019 | Davalos et al. |
| 10,245,105 B2 | 4/2019 | Davalos et al. |
| 10,272,178 B2 | 4/2019 | Davalos et al. |
| 10,286,108 B2 | 5/2019 | Davalos et al. |
| 10,292,755 B2 | 5/2019 | Davalos et al. |
| 2001/0039393 A1 | 11/2001 | Mori et al. |
| 2001/0044596 A1 | 11/2001 | Jaafar |
| 2001/0046706 A1 | 11/2001 | Rubinsky et al. |
| 2001/0047167 A1 | 11/2001 | Heggeness |
| 2001/0051366 A1 | 12/2001 | Rubinsky et al. |
| 2002/0002393 A1 | 1/2002 | Mitchell |
| 2002/0010491 A1 | 1/2002 | Schoenbach et al. |
| 2002/0022864 A1 | 2/2002 | Mahvi et al. |
| 2002/0040204 A1 | 4/2002 | Dev et al. |
| 2002/0049370 A1 | 4/2002 | Laufer et al. |
| 2002/0052601 A1 | 5/2002 | Goldberg et al. |
| 2002/0055731 A1 | 5/2002 | Atala et al. |
| 2002/0065541 A1 | 5/2002 | Fredricks et al. |
| 2002/0072742 A1 | 6/2002 | Schaefer et al. |
| 2002/0077314 A1 | 6/2002 | Falk et al. |
| 2002/0077676 A1 | 6/2002 | Schroeppel et al. |
| 2002/0082543 A1 | 6/2002 | Park et al. |
| 2002/0099323 A1 | 7/2002 | Dev et al. |
| 2002/0104318 A1 | 8/2002 | Jaafar et al. |
| 2002/0111615 A1 | 8/2002 | Cosman et al. |
| 2002/0112729 A1 | 8/2002 | DeVore et al. |
| 2002/0115208 A1 | 8/2002 | Mitchell et al. |
| 2002/0119437 A1 | 8/2002 | Grooms et al. |
| 2002/0133324 A1 | 9/2002 | Weaver et al. |
| 2002/0137121 A1 | 9/2002 | Rubinsky et al. |
| 2002/0138075 A1 | 9/2002 | Edwards et al. |
| 2002/0138117 A1 | 9/2002 | Son |
| 2002/0143365 A1 | 10/2002 | Herbst |
| 2002/0147462 A1 | 10/2002 | Mair et al. |
| 2002/0156472 A1 | 10/2002 | Lee et al. |
| 2002/0161361 A1 | 10/2002 | Sherman et al. |
| 2002/0183684 A1 | 12/2002 | Dev et al. |
| 2002/0183735 A1 | 12/2002 | Edwards et al. |
| 2002/0183740 A1 | 12/2002 | Edwards et al. |
| 2002/0188242 A1 | 12/2002 | Wu |
| 2002/0193784 A1 | 12/2002 | McHale et al. |
| 2002/0193831 A1 | 12/2002 | Smith |
| 2003/0009110 A1 | 1/2003 | Tu et al. |
| 2003/0016168 A1 | 1/2003 | Jandrell |
| 2003/0055220 A1 | 3/2003 | Legrain |
| 2003/0055420 A1 | 3/2003 | Kadhiresan et al. |
| 2003/0059945 A1 | 3/2003 | Dzekunov et al. |
| 2003/0060856 A1 | 3/2003 | Chornenky et al. |
| 2003/0078490 A1 | 4/2003 | Damasco et al. |
| 2003/0088189 A1 | 5/2003 | Tu et al. |
| 2003/0088199 A1 | 5/2003 | Kawaji |
| 2003/0096407 A1 | 5/2003 | Atala et al. |
| 2003/0105454 A1 | 6/2003 | Cucin |
| 2003/0109871 A1 | 6/2003 | Johnson et al. |
| 2003/0127090 A1 | 7/2003 | Gifford et al. |
| 2003/0130711 A1 | 7/2003 | Pearson et al. |
| 2003/0135242 A1 | 7/2003 | Mongeon et al. |
| 2003/0149451 A1 | 8/2003 | Chomenky et al. |
| 2003/0154988 A1 | 8/2003 | DeVore et al. |
| 2003/0159700 A1 | 8/2003 | Laufer et al. |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0195385 A1 | 10/2003 | DeVore |
| 2003/0195406 A1 | 10/2003 | Jenkins et al. |
| 2003/0199050 A1 | 10/2003 | Mangano et al. |
| 2003/0208200 A1 | 11/2003 | Palanker et al. |
| 2003/0208236 A1 | 11/2003 | Heil et al. |
| 2003/0212394 A1 | 11/2003 | Pearson et al. |
| 2003/0212412 A1 | 11/2003 | Dillard et al. |
| 2003/0225360 A1 | 12/2003 | Eppstein et al. |
| 2003/0228344 A1 | 12/2003 | Fields et al. |
| 2004/0009459 A1 | 1/2004 | Anderson et al. |
| 2004/0019371 A1 | 1/2004 | Jaafar et al. |
| 2004/0055606 A1 | 3/2004 | Hendricksen et al. |
| 2004/0059328 A1 | 3/2004 | Daniel et al. |
| 2004/0059389 A1 | 3/2004 | Chomenky et al. |
| 2004/0068228 A1 | 4/2004 | Cunningham |
| 2004/0116965 A1 | 6/2004 | Falkenberg |
| 2004/0133194 A1 | 7/2004 | Eum et al. |
| 2004/0138715 A1 | 7/2004 | Groeningen et al. |
| 2004/0146877 A1 | 7/2004 | Diss et al. |
| 2004/0153057 A1 | 8/2004 | Davison |
| 2004/0176855 A1 | 9/2004 | Badylak |
| 2004/0193042 A1* | 9/2004 | Scampini ............... A61B 8/00 600/424 |
| 2004/0193097 A1 | 9/2004 | Hofmann et al. |
| 2004/0199159 A1 | 10/2004 | Lee et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0230187 A1 | 11/2004 | Lee et al. |
| 2004/0236376 A1 | 11/2004 | Miklavcic et al. |
| 2004/0243107 A1 | 12/2004 | Macoviak et al. |
| 2004/0267189 A1 | 12/2004 | Mavor et al. |
| 2004/0267340 A1 | 12/2004 | Cioanta et al. |
| 2005/0010209 A1 | 1/2005 | Lee et al. |
| 2005/0010259 A1 | 1/2005 | Gerber |
| 2005/0013870 A1 | 1/2005 | Freyman et al. |
| 2005/0020965 A1 | 1/2005 | Rioux et al. |
| 2005/0043726 A1 | 2/2005 | Mchale et al. |
| 2005/0048651 A1 | 3/2005 | Ryttsen et al. |
| 2005/0049541 A1 | 3/2005 | Behar et al. |
| 2005/0061322 A1 | 3/2005 | Freitag |
| 2005/0066974 A1 | 3/2005 | Fields et al. |
| 2005/0143817 A1 | 6/2005 | Hunter et al. |
| 2005/0165393 A1 | 7/2005 | Eppstein |
| 2005/0171522 A1 | 8/2005 | Christopherson |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0197619 A1 | 9/2005 | Rule et al. |
| 2005/0261672 A1 | 11/2005 | Deem et al. |
| 2005/0267407 A1 | 12/2005 | Goldman |
| 2005/0282284 A1 | 12/2005 | Rubinsky et al. |
| 2005/0283149 A1 | 12/2005 | Thorne et al. |
| 2005/0288684 A1 | 12/2005 | Aronson et al. |
| 2005/0288702 A1 | 12/2005 | McGurk et al. |
| 2005/0288730 A1 | 12/2005 | Deem et al. |
| 2006/0004356 A1 | 1/2006 | Bilski et al. |
| 2006/0004400 A1 | 1/2006 | McGurk et al. |
| 2006/0009748 A1 | 1/2006 | Mathis |
| 2006/0015147 A1 | 1/2006 | Persson et al. |
| 2006/0020347 A1 | 1/2006 | Barrett et al. |
| 2006/0024359 A1 | 2/2006 | Walker et al. |
| 2006/0025760 A1 | 2/2006 | Podhajsky |
| 2006/0074413 A1 | 4/2006 | Behzadian |
| 2006/0079838 A1 | 4/2006 | Walker et al. |
| 2006/0079845 A1 | 4/2006 | Howard et al. |
| 2006/0079883 A1 | 4/2006 | Elmouelhi et al. |
| 2006/0085054 A1 | 4/2006 | Zikorus et al. |
| 2006/0089635 A1 | 4/2006 | Young et al. |
| 2006/0121610 A1 | 6/2006 | Rubinsky et al. |
| 2006/0142801 A1 | 6/2006 | Demarais et al. |
| 2006/0149123 A1 | 7/2006 | Vidlund et al. |
| 2006/0173490 A1 | 8/2006 | Lafontaine et al. |
| 2006/0182684 A1 | 8/2006 | Beliveau |
| 2006/0195146 A1 | 8/2006 | Tracey et al. |
| 2006/0212032 A1 | 9/2006 | Daniel et al. |
| 2006/0212078 A1 | 9/2006 | Demarais et al. |
| 2006/0217703 A1 | 9/2006 | Chornenky et al. |
| 2006/0224188 A1 | 10/2006 | Libbus et al. |
| 2006/0235474 A1 | 10/2006 | Demarais |
| 2006/0247619 A1 | 11/2006 | Kaplan et al. |
| 2006/0264752 A1 | 11/2006 | Rubinsky et al. |
| 2006/0264807 A1 | 11/2006 | Westersten et al. |

(56) References Cited

U.S. PATENT DOCUMENTS

| | | |
|---|---|---|
| 2006/0269531 A1 | 11/2006 | Beebe et al. |
| 2006/0276710 A1 | 12/2006 | Krishnan |
| 2006/0278241 A1 | 12/2006 | Ruano |
| 2006/0283462 A1 | 12/2006 | Fields et al. |
| 2006/0293713 A1 | 12/2006 | Rubinsky et al. |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2006/0293734 A1 | 12/2006 | Scott et al. |
| 2007/0010805 A1 | 1/2007 | Fedewa et al. |
| 2007/0016183 A1 | 1/2007 | Lee et al. |
| 2007/0016185 A1 | 1/2007 | Tullis et al. |
| 2007/0021803 A1 | 1/2007 | Deem et al. |
| 2007/0025919 A1 | 2/2007 | Deem et al. |
| 2007/0043345 A1 | 2/2007 | Davalos et al. |
| 2007/0060989 A1 | 3/2007 | Deem et al. |
| 2007/0078391 A1 | 4/2007 | Wortley et al. |
| 2007/0088347 A1 | 4/2007 | Young et al. |
| 2007/0093789 A1 | 4/2007 | Smith |
| 2007/0096048 A1 | 5/2007 | Clerc |
| 2007/0118069 A1 | 5/2007 | Persson et al. |
| 2007/0129711 A1 | 6/2007 | Altshuler et al. |
| 2007/0129760 A1 | 6/2007 | Demarais et al. |
| 2007/0151848 A1 * | 7/2007 | Novak ............... G01N 27/3276 204/412 |
| 2007/0156135 A1 | 7/2007 | Rubinsky et al. |
| 2007/0191889 A1 | 8/2007 | Lang |
| 2007/0203486 A1 | 8/2007 | Young |
| 2007/0230757 A1 | 10/2007 | Trachtenberg et al. |
| 2007/0239099 A1 | 10/2007 | Goldfarb et al. |
| 2007/0244521 A1 | 10/2007 | Bomzin et al. |
| 2007/0287950 A1 | 12/2007 | Kjeken et al. |
| 2007/0295336 A1 | 12/2007 | Nelson et al. |
| 2007/0295337 A1 | 12/2007 | Nelson et al. |
| 2008/0015571 A1 | 1/2008 | Rubinsky et al. |
| 2008/0021371 A1 | 1/2008 | Rubinsky et al. |
| 2008/0027314 A1 | 1/2008 | Miyazaki et al. |
| 2008/0027343 A1 | 1/2008 | Fields et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin et al. |
| 2008/0065062 A1 * | 3/2008 | Leung ............... A61B 18/1206 606/41 |
| 2008/0071262 A1 | 3/2008 | Azure |
| 2008/0097139 A1 | 4/2008 | Clerc et al. |
| 2008/0097422 A1 | 4/2008 | Edwards et al. |
| 2008/0103529 A1 | 5/2008 | Schoenbach et al. |
| 2008/0121375 A1 | 5/2008 | Richason et al. |
| 2008/0125772 A1 | 5/2008 | Stone et al. |
| 2008/0132826 A1 | 6/2008 | Shadduck et al. |
| 2008/0132884 A1 | 6/2008 | Rubinsky et al. |
| 2008/0132885 A1 | 6/2008 | Rubinsky et al. |
| 2008/0140064 A1 | 6/2008 | Vegesna |
| 2008/0146934 A1 | 6/2008 | Czygan et al. |
| 2008/0154259 A1 | 6/2008 | Gough et al. |
| 2008/0167649 A1 | 7/2008 | Edwards et al. |
| 2008/0171985 A1 | 7/2008 | Karakoca |
| 2008/0190434 A1 | 8/2008 | Wai |
| 2008/0200911 A1 | 8/2008 | Long |
| 2008/0200912 A1 | 8/2008 | Long |
| 2008/0208052 A1 | 8/2008 | LePivert et al. |
| 2008/0210243 A1 | 9/2008 | Clayton et al. |
| 2008/0214986 A1 | 9/2008 | Ivorra et al. |
| 2008/0236593 A1 | 10/2008 | Nelson et al. |
| 2008/0249503 A1 | 10/2008 | Fields et al. |
| 2008/0262489 A1 | 10/2008 | Steinke |
| 2008/0269586 A1 | 10/2008 | Rubinsky et al. |
| 2008/0269838 A1 | 10/2008 | Brighton et al. |
| 2008/0275465 A1 | 11/2008 | Paul et al. |
| 2008/0281319 A1 | 11/2008 | Paul et al. |
| 2008/0283065 A1 | 11/2008 | Chang et al. |
| 2008/0288038 A1 | 11/2008 | Paul et al. |
| 2008/0300589 A1 | 12/2008 | Paul et al. |
| 2008/0306427 A1 | 12/2008 | Bailey |
| 2008/0312599 A1 | 12/2008 | Rosenberg |
| 2009/0018206 A1 | 1/2009 | Barkan et al. |
| 2009/0024075 A1 | 1/2009 | Schroeppel et al. |
| 2009/0029407 A1 | 1/2009 | Gazit et al. |
| 2009/0038752 A1 | 2/2009 | Weng et al. |
| 2009/0062788 A1 | 3/2009 | Long et al. |
| 2009/0062792 A1 | 3/2009 | Vakharia et al. |
| 2009/0081272 A1 | 3/2009 | Clarke et al. |
| 2009/0105703 A1 | 4/2009 | Shadduck |
| 2009/0114226 A1 | 5/2009 | Deem et al. |
| 2009/0125009 A1 | 5/2009 | Zikorus et al. |
| 2009/0138014 A1 | 5/2009 | Bonutti |
| 2009/0143705 A1 | 6/2009 | Danek et al. |
| 2009/0157166 A1 | 6/2009 | Singhal et al. |
| 2009/0163904 A1 | 6/2009 | Miller et al. |
| 2009/0171280 A1 | 7/2009 | Samuel et al. |
| 2009/0177111 A1 | 7/2009 | Miller et al. |
| 2009/0186850 A1 | 7/2009 | Kiribayashi et al. |
| 2009/0192508 A1 | 7/2009 | Laufer et al. |
| 2009/0198231 A1 | 8/2009 | Esser et al. |
| 2009/0228001 A1 | 9/2009 | Pacey |
| 2009/0247933 A1 | 10/2009 | Maor et al. |
| 2009/0248012 A1 | 10/2009 | Maor et al. |
| 2009/0269317 A1 | 10/2009 | Davalos |
| 2009/0275827 A1 | 11/2009 | Aiken et al. |
| 2009/0281477 A1 | 11/2009 | Mikus et al. |
| 2009/0292342 A1 | 11/2009 | Rubinsky et al. |
| 2009/0301480 A1 | 12/2009 | Elsakka et al. |
| 2009/0306544 A1 | 12/2009 | Ng et al. |
| 2009/0306545 A1 | 12/2009 | Elsakka et al. |
| 2009/0318905 A1 | 12/2009 | Bhargav et al. |
| 2009/0326436 A1 | 12/2009 | Rubinsky et al. |
| 2009/0326570 A1 | 12/2009 | Brown |
| 2010/0004623 A1 | 1/2010 | Hamilton, Jr. et al. |
| 2010/0006441 A1 * | 1/2010 | Renaud ............. B01L 3/502746 204/643 |
| 2010/0023004 A1 | 1/2010 | Francischelli et al. |
| 2010/0030211 A1 | 2/2010 | Davalos et al. |
| 2010/0049190 A1 | 2/2010 | Long et al. |
| 2010/0057074 A1 | 3/2010 | Roman et al. |
| 2010/0069921 A1 | 3/2010 | Miller et al. |
| 2010/0087813 A1 | 4/2010 | Long |
| 2010/0130975 A1 | 5/2010 | Long |
| 2010/0147701 A1 | 6/2010 | Field |
| 2010/0152725 A1 | 6/2010 | Pearson et al. |
| 2010/0160850 A1 | 6/2010 | Ivorra et al. |
| 2010/0168735 A1 | 7/2010 | Deno et al. |
| 2010/0174282 A1 | 7/2010 | Demarais et al. |
| 2010/0179530 A1 | 7/2010 | Long et al. |
| 2010/0196984 A1 | 8/2010 | Rubinsky et al. |
| 2010/0204560 A1 | 8/2010 | Salahieh et al. |
| 2010/0204638 A1 | 8/2010 | Hobbs et al. |
| 2010/0222677 A1 | 9/2010 | Placek et al. |
| 2010/0228234 A1 | 9/2010 | Hyde et al. |
| 2010/0228247 A1 | 9/2010 | Paul et al. |
| 2010/0241117 A1 | 9/2010 | Paul et al. |
| 2010/0249771 A1 | 9/2010 | Pearson et al. |
| 2010/0250209 A1 | 9/2010 | Pearson et al. |
| 2010/0255795 A1 | 10/2010 | Rubinsky et al. |
| 2010/0256628 A1 | 10/2010 | Pearson et al. |
| 2010/0256630 A1 | 10/2010 | Hamilton, Jr. et al. |
| 2010/0261994 A1 | 10/2010 | Davalos et al. |
| 2010/0286690 A1 | 11/2010 | Paul et al. |
| 2010/0298823 A1 | 11/2010 | Cao et al. |
| 2010/0331758 A1 | 12/2010 | Davalos et al. |
| 2011/0017207 A1 | 1/2011 | Hendricksen et al. |
| 2011/0034209 A1 | 2/2011 | Rubinsky et al. |
| 2011/0064671 A1 | 3/2011 | Bynoe |
| 2011/0106221 A1 | 5/2011 | Robert et al. |
| 2011/0112531 A1 | 5/2011 | Landis et al. |
| 2011/0118727 A1 | 5/2011 | Fish et al. |
| 2011/0118732 A1 | 5/2011 | Rubinsky et al. |
| 2011/0130834 A1 | 6/2011 | Wilson et al. |
| 2011/0144524 A1 | 6/2011 | Fish et al. |
| 2011/0144635 A1 | 6/2011 | Harper et al. |
| 2011/0144657 A1 | 6/2011 | Fish et al. |
| 2011/0152678 A1 | 6/2011 | Aljuri et al. |
| 2011/0166499 A1 | 7/2011 | Demarais et al. |

(56) References Cited

U.S. PATENT DOCUMENTS

| | | | |
|---|---|---|---|
| 2011/0176037 A1* | 7/2011 | Benkley, III | G06K 9/0002 348/294 |
| 2011/0202053 A1 | 8/2011 | Moss et al. | |
| 2011/0217730 A1 | 9/2011 | Gazit et al. | |
| 2011/0251607 A1 | 10/2011 | Kruecker et al. | |
| 2011/0301587 A1 | 12/2011 | Deem et al. | |
| 2012/0034131 A1 | 2/2012 | Rubinsky et al. | |
| 2012/0059255 A1 | 3/2012 | Paul et al. | |
| 2012/0071872 A1 | 3/2012 | Rubinsky et al. | |
| 2012/0071874 A1 | 3/2012 | Davalos et al. | |
| 2012/0085649 A1 | 4/2012 | Sane et al. | |
| 2012/0089009 A1 | 4/2012 | Omary et al. | |
| 2012/0090646 A1 | 4/2012 | Tanaka et al. | |
| 2012/0095459 A1 | 4/2012 | Callas et al. | |
| 2012/0109122 A1 | 5/2012 | Arena et al. | |
| 2012/0130289 A1 | 5/2012 | Demarais et al. | |
| 2012/0150172 A1 | 6/2012 | Ortiz et al. | |
| 2012/0165813 A1 | 6/2012 | Lee et al. | |
| 2012/0179091 A1 | 7/2012 | Ivorra et al. | |
| 2012/0226218 A1 | 9/2012 | Phillips et al. | |
| 2012/0226271 A1 | 9/2012 | Callas et al. | |
| 2012/0265186 A1 | 10/2012 | Burger et al. | |
| 2012/0277741 A1 | 11/2012 | Davalos et al. | |
| 2012/0303020 A1 | 11/2012 | Chornenky et al. | |
| 2012/0310236 A1 | 12/2012 | Placek et al. | |
| 2013/0030239 A1 | 1/2013 | Weyh et al. | |
| 2013/0090646 A1 | 4/2013 | Moss et al. | |
| 2013/0108667 A1 | 5/2013 | Soikum et al. | |
| 2013/0110106 A1 | 5/2013 | Richardson | |
| 2013/0184702 A1 | 7/2013 | Neal, II et al. | |
| 2013/0196441 A1 | 8/2013 | Rubinsky et al. | |
| 2013/0197425 A1 | 8/2013 | Golberg et al. | |
| 2013/0202766 A1 | 8/2013 | Rubinsky et al. | |
| 2013/0218157 A1 | 8/2013 | Callas et al. | |
| 2013/0253415 A1 | 9/2013 | Sane et al. | |
| 2013/0281968 A1 | 10/2013 | Davalos et al. | |
| 2013/0345697 A1 | 12/2013 | Garcia et al. | |
| 2013/0345779 A1 | 12/2013 | Maor et al. | |
| 2014/0017218 A1 | 1/2014 | Scott et al. | |
| 2014/0039489 A1 | 2/2014 | Davalos et al. | |
| 2014/0046322 A1 | 2/2014 | Callas et al. | |
| 2014/0066913 A1 | 3/2014 | Sherman | |
| 2014/0081255 A1 | 3/2014 | Johnson et al. | |
| 2014/0088578 A1 | 3/2014 | Rubinsky et al. | |
| 2014/0121663 A1 | 5/2014 | Pearson et al. | |
| 2014/0121728 A1 | 5/2014 | Dhillon et al. | |
| 2014/0163551 A1 | 6/2014 | Maor et al. | |
| 2014/0207133 A1 | 7/2014 | Model et al. | |
| 2014/0296844 A1 | 10/2014 | Kevin et al. | |
| 2014/0309579 A1 | 10/2014 | Rubinsky et al. | |
| 2014/0378964 A1 | 12/2014 | Pearson | |
| 2015/0088120 A1 | 3/2015 | Garcia et al. | |
| 2015/0088220 A1 | 3/2015 | Callas et al. | |
| 2015/0112333 A1 | 4/2015 | Chorenky et al. | |
| 2015/0126922 A1 | 5/2015 | Willis | |
| 2015/0152504 A1 | 6/2015 | Lin | |
| 2015/0164584 A1 | 6/2015 | Davalos et al. | |
| 2015/0173824 A1 | 6/2015 | Davalos et al. | |
| 2015/0201996 A1 | 7/2015 | Rubinsky et al. | |
| 2015/0265349 A1 | 9/2015 | Moss et al. | |
| 2015/0289923 A1 | 10/2015 | Davalos et al. | |
| 2015/0320488 A1 | 11/2015 | Moshe et al. | |
| 2015/0320999 A1 | 11/2015 | Nuccitelli et al. | |
| 2015/0327944 A1 | 11/2015 | Robert et al. | |
| 2016/0022957 A1 | 1/2016 | Hobbs et al. | |
| 2016/0066977 A1 | 3/2016 | Neal et al. | |
| 2016/0074114 A1 | 3/2016 | Pearson et al. | |
| 2016/0113708 A1 | 4/2016 | Moss et al. | |
| 2016/0143698 A1 | 5/2016 | Garcia et al. | |
| 2016/0235470 A1 | 8/2016 | Callas et al. | |
| 2016/0287313 A1 | 10/2016 | Rubinsky et al. | |
| 2016/0287314 A1 | 10/2016 | Arena et al. | |
| 2016/0338761 A1 | 11/2016 | Chornenky et al. | |
| 2016/0354142 A1 | 12/2016 | Pearson et al. | |
| 2016/0367310 A1 | 12/2016 | Onik et al. | |
| 2017/0035501 A1 | 2/2017 | Chornenky et al. | |
| 2017/0189579 A1 | 7/2017 | Davalos | |
| 2017/0209620 A1 | 7/2017 | Davalos et al. | |
| 2017/0266438 A1 | 9/2017 | Sano | |
| 2017/0360326 A1 | 12/2017 | Davalos | |
| 2018/0071014 A1 | 3/2018 | Neal et al. | |
| 2018/0125565 A1 | 5/2018 | Sano et al. | |
| 2018/0161086 A1 | 6/2018 | Davalos et al. | |
| 2019/0029749 A1 | 1/2019 | Garcia | |
| 2019/0046255 A1 | 2/2019 | Davalos et al. | |
| 2019/0069945 A1 | 3/2019 | Davalos et al. | |
| 2019/0083169 A1 | 3/2019 | Single et al. | |
| 2019/0133671 A1 | 5/2019 | Davalos et al. | |
| 2019/0175248 A1 | 6/2019 | Neal, II | |
| 2019/0175260 A1 | 6/2019 | Davalos | |
| 2019/0223938 A1 | 7/2019 | Arena et al. | |
| 2019/0232048 A1 | 8/2019 | Latouche et al. | |
| 2019/0233809 A1 | 8/2019 | Neal et al. | |
| 2019/0256839 A1 | 8/2019 | Neal et al. | |
| 2019/0282294 A1 | 9/2019 | Davalos et al. | |
| 2019/0328445 A1 | 10/2019 | Sano et al. | |
| 2019/0351224 A1 | 11/2019 | Sano et al. | |

FOREIGN PATENT DOCUMENTS

| | | |
|---|---|---|
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| CA | 2297846 A1 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |
| CA | 2631940 A1 | 6/2007 |
| CA | 2631946 A1 | 6/2007 |
| CA | 2632604 A1 | 6/2007 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| DE | 86311 | 1/1953 |
| DE | 4000893 | 7/1991 |
| DE | 60038026 | 2/2009 |
| EP | 0218275 A1 | 4/1987 |
| EP | 0339501 A2 | 11/1989 |
| EP | 0378132 A | 7/1990 |
| EP | 0533511 A1 | 3/1993 |
| EP | 0998235 A1 | 5/2000 |
| EP | 0528891 B1 | 7/2000 |
| EP | 1196550 A2 | 4/2002 |
| EP | 1439792 A1 | 7/2004 |
| EP | 1442765 A1 | 8/2004 |
| EP | 1462065 A2 | 9/2004 |
| EP | 1061983 B1 | 11/2004 |
| EP | 1493397 A1 | 1/2005 |
| EP | 1506039 A1 | 2/2005 |
| EP | 0935482 B1 | 5/2005 |
| EP | 1011495 B1 | 11/2005 |
| EP | 1796568 A1 | 6/2007 |
| EP | 1207797 B1 | 2/2008 |
| EP | 1406685 B1 | 6/2008 |
| EP | 1424970 B1 | 12/2008 |
| EP | 2381829 A1 | 11/2011 |
| EP | 2413833 A1 | 2/2012 |
| EP | 1791485 B1 | 12/2014 |
| EP | 2373241 B1 | 1/2015 |
| EP | 1962710 B1 | 8/2015 |
| EP | 1962708 B1 | 9/2015 |
| EP | 1962945 B1 | 4/2016 |
| ES | 2300272 | 6/2008 |
| ES | 2315493 | 4/2009 |
| JP | 2001510702 A | 8/2001 |
| JP | 2003505072 A | 2/2003 |
| JP | 2003506064 A | 2/2003 |
| JP | 2004203224 A | 7/2004 |
| JP | 2004525726 A | 8/2004 |

(56) References Cited

FOREIGN PATENT DOCUMENTS

| | | |
|---|---|---|
| JP | 2004303590 A | 10/2004 |
| JP | 2005501596 A | 1/2005 |
| JP | 2005526579 A | 9/2005 |
| JP | 2008508946 A | 3/2008 |
| JP | 4252316 B2 | 4/2009 |
| JP | 2009518130 A | 5/2009 |
| JP | 2009518150 A | 5/2009 |
| JP | 2009518151 A | 5/2009 |
| JP | 2009532077 A | 9/2009 |
| JP | 2010503496 A | 2/2010 |
| JP | 2011137025 | 7/2011 |
| JP | 2011137025 A | 7/2011 |
| JP | 2012510332 A | 5/2012 |
| JP | 2012515018 A | 7/2012 |
| JP | 2012521863 A | 9/2012 |
| KR | 101034682 A | 5/2011 |
| WO | 9104014 | 4/1991 |
| WO | 9634571 | 11/1996 |
| WO | 9639531 A | 12/1996 |
| WO | 9810745 | 3/1998 |
| WO | 9814238 A | 4/1998 |
| WO | 9901076 | 1/1999 |
| WO | 9904710 | 2/1999 |
| WO | 0020554 A | 4/2000 |
| WO | 0107583 A | 2/2001 |
| WO | 0107584 A | 2/2001 |
| WO | 0107585 A | 2/2001 |
| WO | 0110319 A | 2/2001 |
| WO | 0148153 A | 7/2001 |
| WO | 2001048153 A1 | 7/2001 |
| WO | 0170114 A1 | 9/2001 |
| WO | 0181533 A | 11/2001 |
| WO | 02078527 A | 10/2002 |
| WO | 02089686 A | 11/2002 |
| WO | 02100459 A | 12/2002 |
| WO | 2003020144 A1 | 3/2003 |
| WO | 2003047684 A2 | 6/2003 |
| WO | 03099382 A | 12/2003 |
| WO | 2004037341 A2 | 5/2004 |
| WO | 2004080347 A2 | 9/2004 |
| WO | 2005065284 A | 7/2005 |
| WO | 2006017666 A2 | 2/2006 |
| WO | 2006031541 A1 | 3/2006 |
| WO | 2006130194 A2 | 12/2006 |
| WO | 2007067628 A1 | 6/2007 |
| WO | 2007067937 A2 | 6/2007 |
| WO | 2007067938 A2 | 6/2007 |
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |
| WO | 2007100727 A2 | 9/2007 |
| WO | 2007123690 A2 | 11/2007 |
| WO | 2008063195 A1 | 5/2008 |
| WO | 2008034103 A3 | 11/2008 |
| WO | 2009046176 A1 | 4/2009 |
| WO | 2007137303 | 7/2009 |
| WO | 2009134876 A | 11/2009 |
| WO | 2009135070 A1 | 11/2009 |
| WO | 2009137800 A2 | 11/2009 |
| WO | 2010064154 A1 | 6/2010 |
| WO | 2010080974 A1 | 7/2010 |
| WO | 2010117806 A1 | 10/2010 |
| WO | 2010118387 A | 10/2010 |
| WO | 2010132472 A1 | 11/2010 |
| WO | 2010151277 A | 12/2010 |
| WO | 2011047387 A | 4/2011 |
| WO | 2011062653 A1 | 5/2011 |
| WO | 2011072221 A1 | 6/2011 |
| WO | 2012051433 A2 | 4/2012 |
| WO | 2012071526 A | 5/2012 |
| WO | 2012088149 A | 6/2012 |
| WO | 2015175570 A1 | 11/2015 |
| WO | 2016100325 A1 | 6/2016 |
| WO | 2016164930 A1 | 10/2016 |

OTHER PUBLICATIONS

Nuccitelli, R., et al., A new pulsed electric field therapy for melanoma disrupts the tumor's blood supply and causes complete remission without recurrence. Int J Cancer, 2009. 125(2): p. 438-45.

Davalos, R.V., L.M. Mir, and B. Rubinsky, Tissue Ablation with Irreversible Electroporation. Ann Biomed Eng, 2005. 33(2): p. 223-31.

Pavselj, N., V. Preat, and D. Miklavcic, A numerical model of skin electroporation as a method to enhance gene transfection in skin. 11th Mediterranean Conference on Medical and Biological Engineering and Computing 2007, vols. 1 and 2, 2007. 16(1-2): p. 597-601.

Pavselj, N., et al., The course of tissue permeabilization studied on a mathematical model of a subcutaneous tumor in small animals. Ieee Transactions on Biomedical Engineering, 2005. 52(8): p. 1373-1381.

Abidor, I.G., et al., Electric Breakdown of Bilayer Lipid-Membranes .1. Main Experimental Facts and Their Qualitative Discussion. Bioelectrochemistry and Bioenergetics, 1979. 6(1): p. 37-52.

Benz, R., F. Beckers, and U. Zimmermann, Reversible electrical breakdown of lipid bilayer membranes: a charge-pulse relaxation study. J Membr Bioi, 1979. 48(2): p. 181-204.

Neumann, E. and K. Rosenheck, Permeability changes induced by electric impulses in vesicular membranes. J Membr Bioi, 1972. 10(3): p. 279-90.

Teissie, J. and T.V. Tsang, Electric-Field Induced Transient Pores in Phospholipid-Bilayer Vesicles. Biochemistry, 1981. 20(6): p. 1548-1554.

Zimmermann, U., G. Pilwat, and F. Riemann, Dielectric breakdown of cell membranes. Biophys J, 1974. 14(11): p. 881-99.

Kinosita, K. and T.V. Tsang, Formation and Resealing of Pores of Controlled Sizes in Human Erythrocyte-Membrane. Nature, 1977. 268(5619): p. 438-441.

Davalos, R.V., et al., Electrical impedance tomography for imaging tissue electroporation. IEEE Trans Biomed Eng, 2004. 51(5): p. 761-767.

Ybarra, Gary A, et al. "Breast Imaging using Electrical Impedance Tomography." in Suri, J.S., R.M. Rangayyan, and S. Laxminarayan, Emerging Technologies in Breast Imaging and Mammography2008: American Scientific Publishers.

Gabriel, C., Dielectric properties of biological tissue: variation with age. Bioelectromagnetics, 2005. Suppl 7: p. S12-8.

Song, Z.Q., et al., Mechanisms for steep pulse irreversible electroporation technology to kill human large cell lung cancer cells L9981. International Journal of Clinical and Experimental Medicine, 2014. 7(8): p. 2386-2394.

Garcia, P.A., R.V. Davalos, and D. Miklavcic, A Numerical Investigation of the Electric and Thermal Cell Kill Distributions in Electroporation-Based Therapies in Tissue. Plos One, 2014. 9(8).

Sel, D., et al., Sequential finite element model of tissue electropermeabilization. IEEE Trans Biomed Eng, 2005. 52(5): p. 816-27.

Neal, R.E., 2nd, et al., Experimental Characterization and Numerical Modeling of Tissue Electrical Conductivity during Pulsed Electric Fields for Irreversible Electroporation Treatment Planning. IEEE Trans. Biomed Eng, 2012. 59(4): p. 1076-85.

Garcia, P.A., et al., Intracranial Nonthermal Irreversible Electroporation: In Vivo Analysis. Journal of Membrane Biology, 2010. 236(1): p. 127-136.

Hjouj, Mohammad et al., "Electroporation-Induced BBB Disruption and Tissue Damage Depicted by MRI," Abstracts From 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, p. ii114.

(56) References Cited

OTHER PUBLICATIONS

Ho, et al., Electroporation of Cell Membranes: A Review, Critical Reviews in Biotechnology, 16(4): 349-362, 1996.
Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical Bl, pp. 512-519, 1999.
Huang, et al., Micro-Electroporation: Improving the Efficiency and Understanding of Electrical Permeabilization of Cells, Biomedical Microdevices, vol. 2, pp. 145-150, 1999.
Hughes, et al., An Analysis of Studies Comparing Electrical Impedance Tomography with X-Ray Videofluoroscopy in the Assessment of Swallowing, Physiol. Meas. 15, 1994, pp. A199-A209.
Ibey et al., "Selective cytotoxicity of intense nanosecond-duration electric pulses in mammalian cells." Biochimica Et Biophysica Acta-General Subjects, vol. 1800, pp. 1210-1219 (2010).
Issa, et al., the TUNA Procedure for BPH: Review of the Technology: The TUNA Procedure for BPH: Basic Procedure and Clinical Results, Reprinted from Infections in Urology, Jul./Aug. 1998 and Sep./Oct. 1998.
Vanuša, et al., MRI Macromolecular Contrast Agents as Indicators of Changed Tumor Blood Flow, Radiol. Oncol. 2001; 35(2): 139-47.
Vorra et al., "In vivo electric impedance measurements during and after electroporation of rat live." Bioelectrochemistry, vol. 70, Pgs. 287-295 (2007).
Vorra et al., "In vivo electrical conductivity measurements during and after tumor electroporation: conductivity changes reflect the treatment outcome." Physics in Medicine and Biology, vol. 54, Pgs. 5949-5963 (2009).
Vorra, "Bioimpedance monitoring for physicians: an overview." Biomedical Applications Group, 35 pages (2002).
Jarm et al., "Antivascular effects of electrochemotherapy: implications in treatment of bleeding metastases." Expert Rev Anticancer Ther. vol. 10, pp. 729-746 (2010).
Jaroszeski, et al., In Vivo Gene Delivery by Electroporation, Advanced Drug Delivery Review, vol. 35, pp. 131-137, 1999.
Jensen et al., "Tumor volume in subcutaneous mouse xenografts measured by microCT is more accurate and reproducible than determined by 18FFDG-microPET or external caliper." BMC medical Imaging vol. 8:16, 9 Pages (2008).
Jossinet et al., Electrical Impedance Endo-Tomography: Imaging Tissue From Inside, IEEE Transactions on Medical Imaging, Vol. 21, No. 6, Jun. 2002, pp. 560-565.
Kingham et al., "Ablation of perivascular hepatic malignant tumors with irreversible electroporation." Journal of the American College of Surgeons, 2012. 215(3), p. 379-387.
Kinosita and Tsong, "Formation and resealing of pores of controlled sizes in human erythrocyte membrane." Nature, vol. 268 (1977) pp. 438-441.
Kinosita and Tsong, "Voltage-induced pore formation and hemolysis of human erythrocytes." Biochimica et Biophysica Acta (BBA)-Biomembranes, 471 (1977) pp. 227-242.
Kinosita et al.' "Electroporation of cell membrane visualized under a pulsed-laser fluorescence microscope." Biophysical Journal, vol. 53, pp. 1015-1019 (1988).
Kinosita, et al., Hemolysis of Human Erythrocytes by a Transient Electric Field, Proc. Natl. Acad. Sci. USA, vol. 74, No. 5, pp. 1923-1927, 1977.
Kirson et al., "Alternating electric fields arrest cell proliferation in animal tumor models and human brain tumors." Proceedings of the National Academy of Sciences vol. 104, pp. 10152-10157 (2007).
Kotnik and Miklavcic, "Theoretical evaluation of voltage inducement on internal membranes of biological cells exposed to electric fields." Biophysical Journal, vol. 90(2), pp. 480-491 (2006).
Kotnik et al., "Sensitivity of transmembrane voltage induced by applied electric fields—A theoretical analysis", Bioelectrochemistry and Bioenergetics,vol. 43, Issue 2, 1997, pp. 285-291.

Kotnik, T. And D. Miklavcic, "Theoretical evaluation of the distributed power dissipation in biological cells exposed to electric fields", Bioelectromagnetics, 21(5): p. 385-394 (2000).
Kotnik, T., et al., "Cell membrane electropermeabilization by symmetrical bipolar rectangular pulses. Part II. Reduced electrolytic contamination", Bioelectrochemistry, 54(1): p. 91-5 (2001).
Kotnik, T., et al., "Role of pulse shape in cell membrane electropermeabilization", Biochimica Et Biophysica Acta-Biomembranes, 1614(2): p. 193-200 (2003).
Labeed et al., "Differences in the biophysical properties of membrane and cytoplasm of apoptotic cells revealed using dielectrophoresis." Biochimica et Biophysica Acta (BBA)-General Subjects, vol. 1760, pp. 922-929 (2006).
Lackovic, I., et al., "Three-dimensional Finite-element Analysis of Joule Heating in Electrochemotherapy and in vivo Gene Electrotransfer", Ieee Transactions on Dielectrics and Electrical Insulation, 16(5): p. 1338-1347 (2009).
Laufer et al., "Electrical impedance characterization of normal and cancerous human hepatic tissue." Physiological Measurement, vol. 31, Pp. 995-1009 (2010).
Lebar et al., "Inter-pulse interval between rectangular voltage pulses affects electroporation threshold of artificial lipid bilayers." IEEE Transactions on NanoBioscience, vol. 1 (2002) pp. 116-120.
Lee E. W. et al. Advanced Hepatic Ablation Technique for Creating Complete Cell Death: Irreversible Electroporation. Radiology 255, 426-433, doi:10.1148/radiol.10090337 (2010).
Lee, E.W., et al., "Imaging guided percutaneous irreversible electroporation: ultrasound and immunohistological correlation", Technol Cancer Res Treat 6: 287-294 (2007).
Li, W., et al., "The Effects of Irreversible Electroporation (IRE) on Nerves" PloS One, Apr. 2011, 6(4), e18831.
Liu, et al. Measurement of Pharyngeal Transit Time by Electrical Impedance Tomography, Clin. Phys. Physiol. Meas., 1992, vol. 13, Suppl. A, pp. 197-200.
et al., "Targeted Tissue Ablation With Nanosecond Pulses". Ieee Transactions on Biomedical Engineering, 58(8) (2011).
Lundqvist et al. Altering the Biochemical State of Individual Cultured Cells and Organelles with Ultramicroelectrodes, Proc. Natl. Acad. Sci. USA, vol. 95, pp. 10356-10360, Sep. 1998.
Lurquin, Gene Transfer by Electroporation, Molecular Biotechnology, vol. 7, 1997.
Lynn et al., A New Method for the Generation and Use of Focused Ultrasound in Experimental Biology, The Journal Df General Physiology, vol. 26, 179-193, 1942.
Maček Lebar and Miklavčid, "Cell electropermeabilization to small molecules in vitro: control by pulse parameters." Radiology and Oncology, vol. 35(3), pp. 193-202 (2001).
Mahmood, F., et al., "Diffusion-Weighted MRI for Verification of Electroporation-Based Treatments", Journal of Membrane Biology 240: 131-138 (2011).
Mahnic-Kalamiza, S., et al., "Educational application for visualization and analysis of electric field strength in multiple electrode electroporation," BMC Med Educ, vol. 12, p. 102, 2012.
Malpica et al., "Grading ovarian serous carcinoma using a two-tier system." The American Journal of Surgical Pathology, vol. 28, pp. 496-504 (2004).
Maor et al., The Effect of Irreversible Electroporation on Blood Vessels, Tech. In Cancer Res. And Treatment, vol. 6, No. 4, Aug. 2007, pp. 307-312.
Vlaor, E., a Ivorra, and B. Rubinsky, Non Thermal Irreversible Electroporation: Novel Technology for Vascular Smooth Vluscle Cells Ablation, PLoS One, 2009, 4(3): p. e4757.
Maor, E., A Ivorra, J. Leor, and B. Rubinsky, Irreversible electroporation attenuates neointimal formation after angioplasty, IEEE Trans Biomed Eng, Sep. 2008, 55(9): p. 2268-74.
Marszalek et al., "Schwan equation and transmembrane potential induced by alternating electric field." Biophysical Journal, vol. 58, pp. 1053-1058 (1990).
Martin, n. R.C.G., et al., "Irreversible electroporation therapy in the management of locally advanced pancreatic adenocarcinoma" Journal of the American College of Surgeons, 2012. 215(3): p. 361-369.
Marty, M., et al., "Electrochemotherapy — An easy, highly effective and safe treatment of cutaneous and subcutaneous metastases:

(56) References Cited

OTHER PUBLICATIONS

Results of ESOPE (European Standard Operating Procedures of Electrochemotherapy) study," European Journal of Cancer Supplements, 4, 3-13, 2006.
Miklavčič, et al., A Validated Model of an in Vivo Electric Field Distribution in Tissues for Electrochemotherapy and for DNA Electrotransfer for Gene Therapy, Biochimica et Biophysica Acta 1523 (2000), pp. 73-83.
Miklavčič, et al., the Importance of Electric Field Distribution for Effective in Vivo Electroporation of Tissues, Biophysical Journal, vol. 74, May 1998, pp. 2152-2158.
Co-pending U.S. Appl. No. 13/550,307 Non-final office action dated Aug. 22, 2019, 19 pages.
Co-pending U.S. Appl. No. 13/550,307 Notice of panel decision from pre-appeal brief review dated May 16, 2019, 2 pages.
Co-pending U.S. Appl. No. 13/550,307 Pre-appeal brief request for review dated Apr. 4, 2019, 7 pages.
Co-Pending U.S. Appl. No. 14/558,631, Final Office Action dated Sep. 1, 2017, 9 pages.
Co-Pending U.S. Appl. No. 14/558,631, Non-Final Office Action dated Jan. 8, 2018, 5 pages.
Co-Pending U.S. Appl. No. 14/558,631, Non-Final Office Action dated Mar. 13, 2017, 10 pages.
Co-Pending U.S. Appl. No. 14/558,631, Notice of Allowance dated Jul. 17, 2018, 2 pages.
Co-Pending U.S. Appl. No. 14/558,631, Notice of Allowance dated Jun. 21, 2018, 7 pages.
Co-Pending U.S. Appl. No. 14/558,631, Response to Jan. 8, 2018 Non-Final Office Action dated Apr. 9, 2018, 8 pages.
Co-Pending U.S. Appl. No. 14/558,631, Response to Mar. 13, 2017 Non-Final Office Action dated Jul. 13, 2017, 10 pages.
Co-Pending U.S. Appl. No. 14/558,631, Response to Sep. 1, 2017 Final Office Action dated Dec. 1, 2017, 7 pages.
Co-Pending U.S. Appl. No. 14/558,631, filed Dec. 2, 2014.
Co-Pending Application U.S. Appl. No. 14/686,380, filed Apr. 14, 2015 and Published as U.S. 2015/0289923 dated Oct. 15, 2015.
Co-Pending Application U.S. Appl. No. 14/808,679, filed Jul. 24, 2015 and Published as U.S. Publication No. 2015/0327944 dated Nov. 19, 2015.
Co-Pending U.S. Appl. No. 14/940,863, Notice of Allowance dated Jan. 25, 2019, 5 pages.
Co-Pending U.S. Appl. No. 14/940,863, Notice of Allowance dated Sep. 19, 2018, 9 pages.
Co-Pending U.S. Appl. No. 14/940,863, Notice of Allowance dated Sep. 19, 2018, 5 pages.
Co-pending U.S. Appl. No. 15/011,752 Final Office Action dated Dec. 19, 2018, 6 pages.
Co-pending U.S. Appl. No. 15/011,752 Non-Final Office Action dated May 11, 2018, 11 pages.
Co-pending U.S. Appl. No. 15/011,752 Notice of Allowance dated Mar. 22, 2019, 6 pages.
Co-pending U.S. Appl. No. 15/011,752 Preliminary Amendment, filed Feb. 2, 2016, 6 pages.
Co-pending U.S. Appl. No. 15/011,752 Response to Dec. 19, 2018 Final Office Action, filed Mar. 5, 2019, 6 pages.
Co-pending U.S. Appl. No. 15/011,752 Response to May 11, 2018 Non-Final Office Action dated Oct. 11, 2018, 11 pages.
Co-pending U.S. Appl. No. 15/011,752, filed Feb. 1, 2016.
Co-Pending U.S. Appl. No. 15/186,653, filed Jun. 20, 2016.
Co-Pending U.S. Appl. No. 15/310,114, filed Nov. 10, 2016.
Co-pending U.S. Appl. No.15/423,986, filed Feb. 3, 2017.
Co-pending U.S. Appl. No.15/424,335, filed Feb. 3, 2017.
Co-pending U.S. Appl. No. 15/843,888, filed Dec. 15, 2017.
Co-pending U.S. Appl. No. 15/881,414, filed Jan. 26, 2018.
Co-pending U.S. Appl. No. 16/152,743 Preliminary Amendment filed Oct. 5, 2018, 7 pages.
Co-pending U.S. Appl. No. 16/177,745, filed Nov. 1, 2018.
Co-pending U.S. Appl. No. 16/232,962, filed Dec. 26, 2018.
Co-pending U.S. Appl. No. 16/275,429, filed Feb. 14, 2019, which published as 2019/0175260 dated Jun. 13, 2019.
Co-pending U.S. Appl. No. 16/275,429 Preliminary Amendment Filed Mar. 28, 2019, 6 pages.
Co-pending U.S. Appl. No. 16/280,511, filed Feb. 20, 2019.
Co-pending U.S. Appl. No. 16/372,520, filed Apr. 2, 2019, which published as 20190223938 on Jul. 25, 2019.
Co-Pending U.S. Appl. No. 16/375,878, filed Apr. 5, 2019, which published dated Aug. 1, 2019 as US 2019-0233809 A1.
Co-pending U.S. Appl. No. 16/404,392, filed May 6, 2019.
Co-pending U.S. Appl. No 16/443,351, filed Jun. 17, 2019 (published as 20190328445 dated Oct. 31, 2019).
Co-pending U.S. Appl. No. 16/520,901, filed Jul. 24, 2019.
Co-pending U.S. Appl. No. 16/535,451, filed Aug. 8, 2019.
Co-Pending U.S. Appl. No. 16/655,845, filed Oct. 17, 2019.
Co-Pending U.S. Appl. No. PCT/US04/43477, filed Dec. 21, 2004.
Co-Pending Application No. PCT/US09/42100, filed Apr. 29, 2009.
Coo-Pending Application No. PCT/US09/62806, filed Oct. 30, 2009.
Co-Pending Application No. PCT/US10/30629, filed Apr. 9, 2010.
Co-Pending Application No. PCT/US10/53077, filed Oct. 18, 2010.
Co-Pending Application No. PCT/US11/62067, filed Nov. 23, 2011.
Co-Pending Application No. PCT/US11/66239, filed Dec. 20, 2011.
Zimmermann, et al., Dielectric Breakdown of Cell Membranes, Biophysical Journal, vol. 14, No. 11, pp. 881-899, 1974.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA-Jun. 5, 2001.
Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp. 894-899.
Agerholm-Larsen, B., et al., "Preclinical Validation of Electrochemotherapy as an Effective Treatment for Brain Tumors", Cancer Research 71: 3753-3762 (2011).
Alberts et al., "Molecular Biology of the Cell," 3rd edition, Garland Science, New York, 1994, 1 page.
Al-Sakere, B. et al., 2007, "Tumor ablation with irreversible electroporation." PLoS One 2.
Amasha, et al., Quantitative Assessment of Impedance Tomography for Temperature Measurements in Microwave Hyperthermia, Clin. Phys. Physiol. Meas., 1998, Suppl. A, 49-53.
Andreason, Electroporation as a Technique for the Transfer of Macromolecules into Mammalian Cell Lines, J. Tiss. Cult. Meth., 15:56-62, 1993.
Appelbaum, L., et al., "U.S. Findings after Irreversible Electroporation Ablation: Radiologic-Pathologic Correlation" Radiology 262(1), 117-125 (2012).
Arena et al. "High-Frequency Irreversible Electroporation (H-FIRE) for Non-thermal Ablation without Muscle contraction." Biomed. Eng. Online, vol. 10, 20 pages. (2011).
Arena, C.B., et al., "A three-dimensional in vitro tumor platform for modeling therapeutic irreversible electroporation." Biophysical Journal, 2012103(9): p. 2033-2042.
Arena, Christopher B., et al., "Towards the development of latent heat storage electrodes for electroporation-based therapies", Applied Physics Letters, 101, 083902 (2012).
Arena, Christopher B., et al.,"Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.
Asami et al., "Dielectric properties of mouse lymphocytes and erythrocytes." Biochimica et Biophysica Acta (BBA)—Molecular Cell Research, 1010 (1989) pp. 49-55.
Bagla, S. And Papadouris, D., "Percutaneous Irreversible Electroporation of Surgically Unresectable Pancreatic cancer: A Case Report" J. Vascular Int. Radio. 23(1), 142-145 (2012).
Baker, et al., Calcium-Dependent Exocytosis in Bovine Adrenal Medullary Cells with Leaky Plasma Membranes, Nature, vol. 276, pp. 620-622, 1978.
Ball, C., K.R. Thomson, and H. Kavnoudias, "Irreversible electroporation: a new challenge in "out of-operating theater" anesthesia." Anesth Analg, 2010. 110(5): p. 1305-9.

(56) References Cited

OTHER PUBLICATIONS

Bancroft, et al., Design of a Flow Perfusion Bioreactor System for Bone Tissue-Engineering Applications, Tissue Engineering, vol. 9, No. 3, 2003, p. 549-554.
Baptista et al., "The Use of Whole Organ Decellularization for the Generation of a Vascularized Liver Organoid," Heptatology, vol. 53, No. 2, pp. 604-617 (2011).
Barber, Electrical Impedance Tomography Applied Potential Tomography, Advances in Biomedical Engineering, Beneken and Thevenin, eds., IOS Press, pp. 165-173, 1993.
Beebe, S.J., et al., "Diverse effects of nanosecond pulsed electric fields on cells and tissues", DNA and Cell Biology, 22(12): 785-796 (2003).
Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-15, vol. I, Piscataway, NJ, USA.
Ben-David, E.,et al., "Characterization of Irreversible Electroporation Ablation in In Vivo Procine Liver" Am. J. Roentgenol. 198(1), W62-W68 (2012).
Blad, et al.' Impedance Spectra of Tumour Tissue in Comparison with Normal Tissue; a Possible Clinical Application for Electrical Impedance Tomography, Physiol. Meas. 17 (1996) A105-A115.
Bolland, F., et al., "Development and characterisation of a full-thickness acellular porcine bladder matrix for tissue engineering", Biomaterials, Elsevier Science Publishers, Barking, GB, vol. 28, No. 6, 28 Nov. 2006, pp. 1061-1070.
Boone, K., Barber, D. & Brown, B. Review—Imaging with electricity: report of the European Concerted Action on impedance Tomography J. Med. Eng. Technol. 21, 201-232 (1997).
Bower et al., "Irreversible electroporation of the pancreas: definitive local therapy without systemic effects." Journal of surgical oncology, 2011. 104(1): p. 22-28.
BPH Management Strategies: Improving Patient Satisfaction, Urology Times, May 2001, vol. 29, Supplement 1.
Brown, et al., Blood Flow Imaging Using Electrical Impedance Tomography, Clin. Phys. Physiol. Meas., 1992, vol. 13, Suppl. A, 175-179.
Brown, S.G., Phototherapy of tumors. World J. Surgery, 1983. 7: p. 700-9.
Cannon et al., "Safety and early efficacy of irreversible electroporation for hepatic tumors in proximity to vital structures." Journal of Surgical Oncology, 6 pages. (2012).
Carpenter A.E. et al., "CellProfiler: image analysis software for identifying and quantifying cell phenotypes." Genome Biol. 2006; 7(10): R100. Published online Oct. 31, 2006, 11 pages.
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).
Chandrasekar, et al., Transurethral Needle Ablation of the Prostate (TUNA) —a Propsective Study, Six Year Follow Up, (Abstract), Presented at 2001 National Meeting, Anaheim, CA, Jun. 5, 2001.
Chang, D.C., "Cell Poration and Cell-Fusion Using an Oscillating Electric-Field". Biophysical Journal, 56(4): p. 541-652 (1989).
Charpentier, K.P., et al., "Irreversible electroporation of the pancreas in swine: a pilot study." HPB: the official journal of the International Hepato Pancreato Biliary Association, 2010. 12(5): p. 348-351.
Chen et al., "Classification of cell types using a microfluidic device for mechanical and electrical measurement on single cells." Lab on a Chip, vol. 11, pp. 3174-3181 (2011).
Chen, M.T. et al. "Two-dimensional nanosecond electric field mapping based on cell electropermeabilization", PMC Biophys, 2(1):9 (2009).
Clark et al., "The electrical properties of resting and secreting pancreas." The Journal of Physiology, vol. 189, pp. 247-260 (1967).

Coates, C.W.,et al., "The Electrical Discharge of the Electric Eel, Electrophorous Electricus," Zoologica, 1937, 22(1), pp. 1-32.
Cook, et al., ACT3: A High-Speed, High-Precision Electrical Impedance Tomgraph, IEEE Transactions on Biomedical Engineering, vol. 41, No. 8, Aug. 1994.
Co-Pending U.S. Appl. No. 12/432,295, filed Apr. 29, 2009.
Co-pending U.S. Appl. No. 10/571,162 filed Oct. 18, 2006 (published as 2007/0043345 dated Feb. 22, 2007).
Co-Pending U.S. Appl. No. 12/609,779, filed Oct. 30, 2009.
Co-pending U.S. Appl. No. 12/751,826, filed Mar. 31, 2010 (published as 2010/0250209 dated Sep. 30, 2010).
Co-pending U.S. Appl. No. 12/751,854, filed Mar. 31, 2010 (published as 2010/0249771 dated Sep. 30, 2010).
Co-Pending U.S. Appl. No. 12/757,901, filed Apr. 9, 2010.
Co-Pending U.S. Appl. No. 12/757,901, Issued as U.S. Pat. No. 8,926,606 dated Jan. 6, 2015, 42 pages.
Co-Pending U.S. Appl. No. 12/906,923, Office Actions and Responses dated Jul. 2017, 55 pages.
Co-Pending U.S. Appl. No. 12/906,923, filed Oct. 18, 2010.
Co-Pending U.S. Appl. No. 12/906,923, Non-Final Office Action dated Oct. 24, 2014, 11 pages.
Co-Pending U.S. Appl. No. 12/906,923, Requirement for Restriction/Election, dated Jan. 29, 2014, 9 pages.
Co-Pending U.S. Appl. No. 12/906,923, Response to Restriction Requirement, dated Mar. 19, 2014, 3 pages.
Miller, L, et al., Cancer cells ablation with irreversible electroporation, Technology in Cancer Research and Treatment 4 (2005) 699-706.
Mir et al., "Mechanisms of Electrochemotherapy" Advanced Drug Delivery Reviews 35:107-118 (1999).
Mir, et al., Effective Treatment of Cutaneous and Subcutaneous Malignant Tumours by Electrochemotherapy, British Journal of Cancer, vol. 77, No. 12, pp. 2336-2342, 1998.
Mir, et al., Electrochemotherapy Potentiation of Antitumour Effect of Bleomycin by Local Electric Pulses, European Journal of Cancer, vol. 27, No. 1, pp. 68-72, 1991.
Mir, et al., Electrochemotherapy, a Novel Antitumor Treatment: First Clinical Trial, C.R. Acad. Sci. Paris, Ser. III, vol. 313, pp. 613-618, 1991.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Mir, L.M., et al., Electric Pulse-Mediated Gene Delivery to Various Animal Tissues, in Advances in Genetics, Academic Press, 2005, p. 83-114.
Mir, Therapeutic Perspectives of in Vivo Cell Electropermeabilization, Bioelectrochemistry, vol. 53, pp. 1-10, 2000.
Mulhall et al., "Cancer, pre-cancer and normal oral cells distinguished by dielectrophoresis." Analytical and Bioanalytical Chemistry, vol. 401, pp. 2455-2463 (2011).
Narayan, et al., Establishment and Characterization of a Human Primary Prostatic Adenocarcinoma Cell Line (ND-1), The Journal of Urology, vol. 148, 1600-1604, Nov. 1992.
Naslund, Cost-Effectiveness of Minimally Invasive Treatments and Transurethral Resection (TURP) in Benign Prostatic Hyperplasia (BPH), (Abstract), Presented at 2001 AUA National Meeting Anaheim, CA, Jun. 5, 2001.
Naslund, Michael J., Transurethral Needle Ablation of the Prostate, Urology, vol. 50, No. 2, Aug. 1997.
Neal II et al., "A Case Report on the Successful Treatment of a Large Soft-Tissue Sarcoma with Irreversible Electroporation," Journal of Clinical Oncology, 29, pgs. 1-6, 2011.
Neal II, R. E., et al., "Experimental characterization and numerical modeling of tissue electrical conductivity during Dulsed electric fields for irreversible electroporation treatment planning," IEEE Trans Biomed Eng., vol. 59:4, pp. 1076-85. Epub Jan. 6, 2012.
Neal II, R. E., et al., "Successful Treatment of a Large Soft Tissue Sarcoma with Irreversible Electroporation", Journal of Clinical Oncology, 29:13, e372-e377 (2011).
Neal II, R.E. et al., "Treatment of breast cancer through the application of irreversible electroporation using a novel minimally

(56) References Cited

OTHER PUBLICATIONS invasive single needle electrode." Breast Cancer Research and Treatment, 2010. 123(1): p. 295-301.
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
Neal Re II, et al. (2013) Improved Local and Systemic Anti-Tumor Efficacy for Irreversible Electroporation in Immunocompetent versus Immunodeficient Mice. PLoS One 8(5): e64559. https://doi.org/10.1371/journal.bone.0064559.
Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801(2011).
Neumann, et al., Gene Transfer into Mouse Lyoma Cells by Electroporation in High Electric Fields, J. Embo., vol. 1, No. 7, pp. 841-845, 1982.
Neumann, et al., Permeability Changes Induced by Electric Impulses in Vesicular Membranes, J. Membrane Biol., vol. 10, pp. 279-290, 1972.
Nikolova, B., et al., "Treatment of Melanoma by Electroporation of Bacillus Calmette-Guerin". Biotechnology & Biotechnological Equipment, 25(3): p. 2522-2524 (2011).
Nuccitelli, R., et al., "A new pulsed electric field therapy for melanoma disrupts the tumor's blood supply and causes complete remission without recurrence", Int J Cancer, 125(2): p. 438-45 (2009).
O'Brien et al., "Investigation of the Alamar Blue (resazurin) fluorescent dye for the assessment of mammalian cell cytotoxicity." European Journal of Biochemistry, vol. 267, pp. 5421-5426 (2000).
Okino, et al., Effects of High-Voltage Electrical Impulse and an Anticancer Drug on in Vivo Growing Tumors, Japanese Journal of Cancer Research, vol. 78, pp. 1319-1321, 1987.
Onik, et al., Sonographic Monitoring of Hepatic Cryosurgery in an Experimental Animal Model, AJR American J. Of Roentgenology, vol. 144, pp. 1043-1047, May 1985.
Onik, et al., Ultrasonic Characteristics of Frozen Liver, Cryobiology, vol. 21, pp. 321-328, 1984.
Onik, G. And B. Rubinsky, eds. "Irreversible electroporation: first patient experience focal therapy of prostate Cancer. Irreversible Electroporation", ed. B. Rubinsky 2010, Springer Berlin Heidelberg, pgs. 235-247.
Onik, G., P. Mikus, and B. Rubinsky, "Irreversible electroporation: implications for prostate ablation." Technol Cancer Res Treat, 2007. 6(4): p. 295-300.
Organ, L.W., Electrophysiological principles of radiofrequency lesion making, Apply. Neurophysiol., 1976. 39: p. 69-76.
Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.
Paszek et al., "Tensional homeostasis and the malignant phenotype." Cancer Cell, vol. 8, pp. 241-254 (2005).
Payselj, N. et al. The course of tissue permeabilization studied on a mathematical model of a subcutaneous tumor in small animals. IEEE Trans Biomed Eng 52, 1373-1381 (2005).
PCT International Preliminary Report on Patentability of Corresponding International Application No. PCT/2011/062067, dated May 28, 2013.
PCT International Preliminary Report on Patentability of Corresponding International Application No. PCT/2011/066239, dated Jun. 25, 2013.
PCT International Search Report dated (Aug. 2, 2011), Written Opinion dated (Aug. 2, 2011), and International Preliminary Report on Patentability dated (Apr. 17, 2012) of PCT/US10/53077.
PCT International Search Report dated (Aug. 22, 2012), and Written Opinion dated (Aug. 22, 2012) of PCT/US11/66239.

PCT International Search Report dated (Aug. 26, 2005), Written Opinion dated (Aug. 26, 2005), and International Preliminary Report on Patentability dated (Jun. 26, 2006) of PCT/US2004/043477.
PCT International Search Report dated (Jan. 19, 2010), Written Opinion dated (Jan. 19, 2010), and International Preliminary Report on Patentability dated (Jan. 4, 2010) of PCT/US09/62806, 15 pgs.
PCT International Search Report dated (Jul. 15, 2010), Written Opinion dated (Jul. 15, 2010), and International Preliminary Report on Patentability dated (Oct. 11, 2011) from PCT/US2010/030629.
PCT International Search Report (Jul. 9, 2009), Written Opinion dated (Jul. 9, 2009), and International Preliminary Report on Patentability dated (Nov. 2, 2010) of PCT/US2009/042100.
PCT International Search Report and Written Opinion dated (Jul. 25, 2012) of PCT/US2011/062067.
PCT International Search Report, 4 pgs, dated (Jul. 30, 2010), Written Opinion, 7 pgs, dated (Jul. 30, 2010), and International Preliminary Report on Patentability, 8 pgs, dated (Oct. 4, 2011) from PCT/US2010/029243.
PCT IPRP for PCTIUSI5/30429 (WO2015175570), dated Nov. 15, 2016.
Phillips, M., Maor, E. & Rubinsky, B. Non-Thermal Irreversible Electroporation for Tissue Decellularization. J. Biomech. Eng, doi:10.1115/1.4001882 (2010).
Piñero, et al., Apoptotic and Necrotic Cell Death Are Both Induced by Electroporation in HL60 Human Promyeloid Leukaemia Cells, Apoptosis, vol., 2, No. 3, 330-336, Aug. 1997.
Polak et al., "On the Electroporation Thresholds of Lipid Bilayers: Molecular Dynamics Simulation Investigations." The Journal of Membrane Biology, vol. 246, pp. 843-850 (2013).
Precision Office TUNA System, When Patient Satisfaction is Your Goal, VidaMed 2001.
Pucihar et al., "Numerical determination of transmembrane voltage induced on irregularly shaped cells." Annals of Biomedical Engineering, vol. 34, pp. 642-652 (2006).
Rajagopal, V. and S.G. Rockson, Coronary restenosis: a review of mechanisms and management, The American Journal of Medicine, 2003, 115(7): p. 547-553.
Dev, et al., Sustained Local Delivery of Heparin to the Rabbit Arterial Wall with an Electroporation Catheter, Catheterization and Cardiovascular Diagnosis, Nov., 1998, vol. 45, No. 3, pp. 337-343.
Duraiswami, et al., Boundary Element Techniques for Efficient 2-D and 3-D Electrical Impedance Tomography, Chemical Engineering Science, vol. 52, No. 13, pp. 2185-2196, 1997.
Duraiswami, et al., Efficient 2D and 3D Electrical Impedance Tomography Using Dual Reciprocity Boundary Element Techniques, Engineering Analysis with Boundary Elements 22, (1998) 13-31.
Duraiswami, et al., Solution of Electrical Impedance Tomography Equations Using Boundary Element Methods, Boundary Element Technology XII, 1997, pp. 226-237.
Edd, J., et al., In-Vivo Results of a New Focal Tissue Ablation Technique: Irreversible Electroporaton, IEEE Trans. Biomed. Eng. 53 (2006) p. 1409-1415.
Edd, J.F, et al., 2007, "Mathematical modeling of irreversible electroporation fortreatment planning.", Technology in Cancer Research and Treatment, 6:275-286.
Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).
Eppich et al., "Pulsed electric fields for selection of hematopoietic cells and depletion of tumor cell contaminants." Nature Biotechnology 18, pp. 882-887 (2000).
Erez, et al, Controlled Destruction and Temperature Distributions in Biological Tissues Subjected to Monoactive Electrocoagulation, Transactions of the ASME: Journal of Mechanical Design, vol. 102, Feb. 1980.
Ermolina et al., "Study of normal and malignant white blood cells by time domain dielectric spectroscopy." IEEE Transactions on Dielectrics and Electrical Insulation, 8 (2001) pp. 253-261.

(56) References Cited

OTHER PUBLICATIONS

Esser, A.T., et al', "Towards solid tumor treatment by irreversible electroporation: intrinsic redistribution of fields and currents in tissue". Technol Cancer Res Treat, 6(4): p. 261-74 (2007).
Esser, A.T., et al., "Towards Solid Tumor Treatment by Nanosecond Pulsed Electric Fields". Technology in Cancer Research & Treatment, 8(4): p. 289-306 (2009).
Extended European Search Report. May 11, 2012. PCT/US2009042100 from EP 09739678.2.
Faroja, M., et al., "Irreversible Electroporation Ablation: Is the entire Damage Nonthermal?", Radiology, 266(2), 462-470 (2013).
=Fischbach et al., "Engineering tumors with 3D scaffolds." Nat Meth 4, pp. 855-860 (2007).
Flanagan et al., "Unique dielectric properties distinguish stem cells and their differentiated progeny." Stem Cells, vol. 26, pp. 656-665 (2008).
Fong et al., "Modeling Ewing sarcoma tumors in vitro with 3D scaffolds." Proceedings of the National Academy of Sciences vol. 110, pp. 6500-6505 (2013).
Foster RS, "High-intensity focused ultrasound in the treatment of prostatic disease", European Urology, 1993, vol. 23 Suppl 1, pp. 29-33.
Foster, R.S., et al., Production of Prostatic Lesions in Canines Using Transrectally Administered High-Intensity Focused Ultrasound. Eur. Urol., 1993; 23: 330-336.
Fox, et al., Sampling Conductivity Images via MCMC, Mathematics Department, Auckland University, New Zealand, May 1997.
Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).
Garcia et al., "Irreversible electroporation (IRE) to treat brain cancer." ASME Summer Bioengineering Conference, Marco Island, FL, Jun. 25-29, 2008.
Garcia P.A., et al., "7.0-T Magnetic Resonance Imaging Characterization of Acute Blood-Brain-Barrier Disruption Achieved with Intracranial Irreversible Electroporation", PLOS One, Nov. 2012, 7:11, e50482.
Garcia Pa., et al., "Pilot study of irreversible electroporation for intracranial surgery", Conf Proc IEEE Eng Med Biol Soc, 2009:6513-6516, 2009.
Garcia PA, Rossmeisl JH, Jr., Neal RE, 2nd, Ellis TL, Davalos RV, "A Parametric Study Delineating Irreversible Electroporation from Thermal Damage Based on a Minimally Invasive Intracranial Procedure", Biomed Eng Online 10: 34 (2011).
Garcia, P. A., et al., "Towards a predictive model of electroporation-based therapies using pre-pulse electrical measurements," Conf Proc IEEE Eng Med Biol Soc, vol. 1 2012, pp. 2575-8, 2012.
Garcia, P. A., et al., "Non-thermal Irreversible Electroporation (N-TIRE) and Adjuvant Fractioned Radiotherapeutic Vlultimodal Therapy for Intracranial Malignant Glioma in a Canine Patient" Technol. Cancer Res. Treatment 10(1), 7333 (2011).
Garcia, P. et al. Intracranial nonthermal irreversible electroporation: in vivo analysis. J Membr Biol 236, 127-136 :2010).
Garcia, Paulo A., Robert E. Neal II and Rafael V. Davalos, Chapter 3, Non-Thermal Irreversible Electroporation for Tissue Ablation, in: Electroporation in Laboratory and Clinical Investigations ISBN 378-1-61668-327-6 Editors: Enrico P. Spugnini and Alfonso Baldi, 2010, 22 pp.
Gascoyne et al., "Membrane changes accompanying the induced differentiation of Friend murine erythroleukemia cells studied by dielectrophoresis." Biochimica et Biophysica Acta (BBA)-Biomembranes, vol. 1149, pp. 119-126 (1993).
Gauger, et al., a Study of Dielectric Membrane Breakdown in the Fucus Egg, J. Membrane Biol., vol. 48, No. 3, pp. 249-264, 1979.
Gehl, et al.' in Vivo Electroporation of Skeletal Muscle: Threshold, Efficacy and Relation to Electric Field Distribution, . Thochimica et Biphysica Acta 1428, 1999, pp. 233-240.

Gençer, et al., Electrical Impedance Tomography: Induced-Current Imaging Achieved with a Multiple Coil System, Eee Transactions on Biomedical Engineering, vol. 43, No. 2, Feb. 1996.
Gilbert, et al., Novel Electrode Designs for Electrochemotherapy, Biochimica et Biophysica Acta 1334, 1997, pp. 9-14.
Gilbert, et al., the Use of Ultrasound Imaging for Monitoring Cryosurgery, Proceedings fith Annual Conference, IEEE Engineering in Medicine and Biology, 107-111, 1984.
Gilbert, T. W., et al., "Decellularization of tissues and organs", Biomaterials, Elsevier Science Publishers, Barking, GB, vol. 27, No. 19, 1 Jul. 2006, pp. 3675-3683.
Gimsa et al., "Dielectric spectroscopy of single human erythrocytes at physiological ionic strength: dispersion of the aytoplasm." Biophysical Journal, vol. 71, pp. 495-506 (1996).
Glidewell, et al., The Use of Magnetic Resonance Imaging Data and the Inclusion of Anisotropic Regions in Electrical Impedance Tomography, Biomed, Sci. Instrum. 1993; 29: 251-7.
Golberg, A. And Rubinsky, B., "A statistical model for multidimensional irreversible electroporation cell death in tissue." Biomed Eng Online, 9, 13 pages, 2010.
Gothelf, et al., Electrochemotherapy: Results of Cancer Treatment Using Enhanced Delivery of Bleomycin by Electroporation, Cancer Treatment Reviews 2003: 29: 371-387.
Gowrishankar T.R., et al., "Microdosimetry for conventional and supra-electroporation in cells with organelles". Biochem Biophys Res Commun, 341(4): p. 1266-76 (2006).
Griffiths, et al., a Dual-Frequency Electrical Impedance Tomography System, Phys. Met Biol., 1989, vol. 34, No. 10, pp. 1465-1476.
Griffiths, The Importance of Phase Measurement in Electrical Impedance Tomography, Phys. Med. Biol., 1987, vol. 32, No. 11, pp. 1435-1444.
Griffiths, Tissue Spectroscopy with Electrical Impedance Tomography: Computer Simulations, IEEE Transactions pn Biomedical Engineering, vol. 42, No. 9, Sep. 1995.
Gumerov, et al., the Dipole Approximation Method and Its Coupling with the Regular Boundary Element Method for Efficient Electrical Impedance Tomography, Boundary Element Technology XIII, 1999.
Hapala, Breaking the Barrier: Methods for Reversible Permeabilization of Cellular Membranes, Critical Reviews in Biotechnology, 17(2): 105-122, 1997.
Helczynska et al., "Hypoxia promotes a dedifferentiated phenotype in ductal breast carcinoma in situ." Cancer Research, vol. 63, pp. 1441-1444 (2003).
Heller, et al., Clinical Applications of Electrochemotherapy, Advanced Drug Delivery Reviews, vol. 35, pp. 119-129, 1999.
Hjouj, M., et al., "Electroporation-Induced Bbb Disruption and Tissue Damage Depicted by MRI", Neuro-Oncology 13: Issue suppl 3, abstract ET-32 (2011).
Hjouj, M., et al., "MRI Study on Reversible and Irreversible Electroporation Induced Blood Brain Barrier Disruption", PLOS One, Aug. 2012, 7:8, e42817.
Co-Pending Application No. PCT/US15/30429, filed May 12, 2015.
Co-pending Application No. PCT/US19/51731, filed Sep. 18, 2019.
Co-pending application No. PCT/US19/51731 Invitation to Pay Additional Search Fees dated Oct. 14, 2010.
Co-Pending Application No. PCT/US2015/030429, Published on Nov. 19, 2015 as WO 2015/175570.
Co-Pending Application No. PCT/US2015/030429, Published Nov. 19, 2015 as WO 2015/175570.
Co-Pending U.S. Appl. No. 12/491,151, filed Jun. 24, 2009.
Co-Pending U.S. Appl. No. 13/332,133, filed Dec. 20, 2011.
Co-Pending U.S. Appl. No. 13/550,307, Aug. 13, 2018 Applicant-Initiated Interview Summary, 3 pages.
Co-Pending U.S. Appl. No. 13/550,307, Final Office Action dated Dec. 5, 2018, 17 pages.
Co-Pending U.S. Appl. No. 13/550,307, Office Actions and Responses through Mar. 2018, 133 pages.
Co-Pending U.S. Appl. No. 13/550,307, Response to Mar. 14, 2018 Non-Final Office Action dated Jul. 16, 2018, 12 pages.
Co-Pending U.S. Appl. No. 13/550,307, filed Jul. 16, 2012.
Co-Pending U.S. Appl. No. 13/919,640, filed Jun. 17, 2013.
Co-Pending U.S. Appl. No. 13/958,152, filed Aug. 2, 2013.
Co-Pending U.S. Appl. No. 13/989,175, filed May 3, 2013.

(56) References Cited

OTHER PUBLICATIONS

Co-Pending U.S. Appl. No. 14/012,832, Ex Parte Quayle Office Action dated Aug. 28, 2015, 6 pages.
Co-Pending U.S. Appl. No. 14/012,832, Notice of Allowance dated Nov. 4, 2015, 5 pages.
Co-Pending U.S. Appl. No. 14/012,832 , Ex Parte Quayle Office Action dated Aug. 28, 2013, 6 pages.
Co-Pending U.S. Appl. No. 14/017,210, filed Sep. 3, 2013.
Co-Pending U.S. Appl. No. 14/627,046, filed Feb. 20, 2015.
Co-Pending U.S. Appl. No. 14/686,380, Final Office Action dated May 9, 2018, 14 pages.
Co-Pending U.S. Appl. No. US 14/686,380, Final Office Action dated Sep. 3, 2019, 28 pages.
Co-Pending U.S. Appl. No. 14/686,380, Non-Final Office Action dated May 1, 2019, 18 pages.
Co-Pending U.S. Appl. No. 14/686,380, Non-Final Office Action dated Nov. 22, 2017, 11 pages.
Co-Pending U.S. Appl. No. 14/686,380, Response to Jul. 19, 2017 Restriction Requirement, dated Sep. 15, 2017, 2 pages.
Co-Pending U.S. Appl. Co. 14/686,380, Response to May 9, 2018 Final Office Action with RCE, dated Aug. 30, 2018, 14 pages.
Co-Pending U.S. Appl. No. 14/686,380, Response to Non-Final Office Action Filed Aug. 1, 2019, 11 pages.
Co-Pending U.S. Appl. No. 14/686,380, Response to Nov. 22, 2017 Non-Final Office Action dated Mar. 28, 2018, 11 pages.
Co-Pending U.S. Appl. No. 14/686,380, Restriction Requirement Jul. 19, 2017, 7 pages.
Co-Pending U.S. Appl. No. 14/686,380 filed Apr. 14, 2015.
Co-Pending U.S. Appl. No. 14/940,863, filed on Nov. 13, 2015 and Published as US 2016/0066977 dated Mar. 10, 2016.
Co-pending U.S. Appl. No. 16/152,743, filed Oct. 5, 2018.
Corovic, S., et a ., "Analytical and numerical quantification and comparison of the local electric field in the tissue for different electrode configurations," Biomed Eng Online, 6, 2007.
Cowley, Good News for Boomers, Newsweek, Dec. 30, 1996/Jan. 6, 1997.
Cox, et al., Surgical Treatment of Atrial Fibrillation: A Review, Europace (2004) 5, S20-S-29.
Crowley, Electrical Breakdown of Biomolecular Lipid Membranes as an Electromechanical Instability, Biophysical Journal, vol. 13, pp. 711-724, 1973.
Dahl et al., "Nuclear shape, mechanics, and mechanotransduction." Circulation Research vol. 102, pp. 1307-1318 :2008).
Daud, Al., et al., "Phase I Trial of Interleukin-12 Plasmid Electroporation in Patients With Metastatic Melanoma," Journal of Clinical Oncology, 26, 5896-5903, Dec 20, 2008.
Davalos, et al., Theoretical Analysis of the Thermal Effects During in Vivo Tissue Electroporation, Bioelectrochemistry, vol. 61, pp. 99-107, 2003.
Davalos, et al., a Feasibility Study for Electrical Impedance Tomography as a Means to Monitor T issue Electroporation for Molecular Medicine, IEEE Transactions on Biomedical Engineering, vol. 49, No. 4, Apr. 2002.
Davalos, et al., Tissue Ablation with Irreversible Electroporation, Annals of Biomedical Engineering, vol. 33, No. 2, pg. 223-231, Feb. 2005.
Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).
Davalos, R.V. et al., "Electrical impedance tomography for imaging tissue electroporation," IEEE Transactions on Biomedical Engineering, 51, 761-767, 2004.
Davalos, Real-Time Imaging for Molecular Medicine through Electrical Impedance Tomography of Electroporation, Dissertation for Ph.D. In Engineering-Mechanical Engineering, Graduate Division of University of California, Berkeley, 2002.
De Vuyst, E, et al., "In situ bipolar Electroporation for localized cell loading with reporter dyes and investigating gap unctional coupling", Biophysical Journal, 94(2): p. 469-479 (2008).

Dean, Nonviral Gene Transfer to Skeletal, Smooth, and Cardiac Muscle in Living Animals, Am J. Physiol Cell Physiol 289: 233-245, 2005.
Demirbas, M. F., "Thermal Energy Storage and Phase Change Materials: An Overview" Energy Sources Part B 1(1), 5-95 (2006).
Dev, et al., Medical Applications of Electroporation, IEEE Transactions of Plasma Science, vol. 28, No. 1, pp. 206-223, Feb. 2000.
Reberšek, M. And D. Miklavčič, "Advantages and Disadvantages of Different Concepts of Electroporation Pulse Generation," Automatika 52(2011) 1, 12-19.
Rols, M.P., et al., Highly Efficient Transfection of Mammalian Cells by Electric Field Pulses: Application to Large Volumes Of Cell Culture by Using a Flow System, Eur. J. Biochem. 1992, 206, pp. 115-121.
Ron et al., "Cell-based screening for membranal and cytoplasmatic markers using dielectric spectroscopy." Biophysical ahemistry, 135 (2008) pp. 59-68.
Rossmeisl et al., "Pathology of non-thermal irreversible electroporation (N-Tire)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rubinsky et al., "Optimal Parameters for the Destruction of Prostate Cancer Using Irreversible Electroporation." the Journal of Urology, 180 (2008) pp. 2668-2674.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. vol. 2 2000. 157-187.
Rubinsky, B., et al., "Irreversible Electroporation: A New Ablation Modality —Clinical Implications" Technol. Cancer Res. Treatment 6(1), 37-48 (2007).
Sabuncu et al., "Dielectrophoretic separation of mouse melanoma clones." Biomicrofluidics, vol. 4, 7 pages (2010).
Salford, L.G., et al. "A new brain tumour therapy combining bleomycin with in vivo electropermeabilization", Biochem. . Biophys. Res. Commun., 194(2): 938-943 (1993).
Salmanzadeh et al., "Investigating dielectric properties of different stages of syngeneic murine ovarian cancer cells" Biomicrofiuidics 7, 011809 (2013), 12 pages.
Salmanzadeh et al., "Dielectrophoretic differentiation of mouse ovarian surface epithelial cells, macrophages, and Fibroblasts using contactless dielectrophoresis." Biomicrofluidics, vol. 6, 13 Pages. (2012).
Salmanzadeh et al., "Sphingolipid Metabolites Modulate Dielectric Characteristics of Cells in a Mouse Ovarian Cancer Progression Model." Integr. Biol., 5(6), pp. 843-852 (2013).
Sano et al., "Contactless Dielectrophoretic Spectroscopy: Examination of the Dielectric Properties of Cells Found in Blood." Electrophoresis, 32, pp. 3164-3171, 2011.
Sano et al., "In-vitro bipolar nano- and microsecond electro-pulse bursts for irreversible electroporation therapies." Bioelectrochemistry vol. 100, pp. 69-79 (2014).
Sano et al., "Modeling and Development of a Low Frequency Contactless Bioelectrophoresis (cDEP) Plafform to Sort cancer Cells from Dilute Whole Blood Samples_" Biosensors & Bioelectronics, 8 pages. (2011).
Sano, M. B., et al., "Towards the creation of decellularized organ constructs using irreversible electroporation and active mechanical perfusion", Biomedical Engineering Online, Biomed Central Ltd, London, GB, vol. 9, No. 1, 10 Dec. 2010, page 83.
Saur et al., "CXCR4 expression increases liver and lung metastasis in a mouse model of pancreatic cancer." Gastroenterology, vol. 129, pp. 1237-1250 (2005).
Schmukler, Impedance Spectroscopy of Biological Cells, Engineering in Medicine and Biology Society, Engineering Advances: New Opportunities for Biomedical Engineers, Proceedings of the 16th Annual Internal Conference of the IEEE, vol. 1, p. A74, downloaded from IEEE Xplore website, 1994.
Schoenbach et al., "Intracellular effect of ultrashort electrical pulses." Bioelectromagnetics, 22 (2001) pp. 440-448.

(56) References Cited

OTHER PUBLICATIONS

Seibert et al., "Clonal variation of MCF-7 breast cancer cells in vitro and in athymic nude mice." Cancer Research, vol. 13, pp. 2223-2239 (1983).
Seidler et al., "A Cre-loxP-based mouse model for conditional somatic gene expression and knockdown in vivo by using avian retroviral vectors." Proceedings of the National Academy of Sciences, vol. 105, pp. 10137-10142 '2008).
Sel, D. et al. Sequential finite element model of tissue electropermeabilization. IEEE Transactions on Biomedical Engineering 52, 816-827, doi:10.1109/tbme.2005.845212 (2005).
Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).
Sersa, et al., Reduced Blood Flow and Oxygenation in SA-1 Tumours after Electrochemotherapy with Cisplatin, British Journal of Cancer, 87, 1047-1054, 2002.
Sersa, et al., Tumour Blood Flow Modifying Effects of Electrochemotherapy: a Potential Vascular Targeted Mechanism, Radio!. Oncol., 37(1): 43-8, 2003.
Sharma, A. , et al., "Review on Thermal Energy Storage with Phase Change Materials and Applications", Renewable Sustainable Energy Rev. 13(2), 318-345 (2009).
Sharma, et al., Poloxamer 188 Decreases Susceptibility of Artificial Lipid Membranes to Electroporation, Biophysical Journal, vol. 71, No. 6, pp. 3229-3241, Dec. 1996.
Shiina, S., et al, Percutaneous ethanol injection therapy for hepatocellular carcinoma: results in 146 patients. AJR, 1993, 160: p. 1023-8.
Szot et al., "3D in vitro bioengineered tumors based on collagen I hydrogels." Biomaterials vol. 32, pp. 7905-7912 (2011).
Talele, S., et al., "Modelling single cell electroporation with bipolar pulse parameters and dynamic pore radii". Journal of Electrostatics, 68(3): p. 261-274 (2010).
Tekle, Ephrem, R. Dean Astumian, and R Boon Chock, Electroporation by using bipolar oscillating electric field: An Improved method for DNA transfection of NIH 3T3 cells, Proc. Natl. Acad. Sci., vol. 88, pp. 4230-4234, May 1991, Biochemistry.
Thompson, et al., To determine whether the temperature of 2% lignocaine gel affects the initial discomfort which may be associated with its instillation into the male urethra, BJU International (1999), 84, 1035-1037.
Thomson, K. R., et al., "Investigation of the Safety of Irreversible Electroporation in Humans" J. Vascular Int. Radio. 22 (5), 611-621 (2011).
TUNA—Suggested Local Anesthesia Guidelines, no. date available.
Verbridge et al., "Oxygen-Controlled Three-Dimensional Cultures to Analyze Tumor Angiogenesis." Tissue Engineering, Part A vol. 16, pp. 2133-2141 (2010).
Vernier, P.T., et al., "Nanoelectropulse-driven membrane perturbation and small molecule permeabilization", Bmc Cell Biology, 7 (2006).
Vidamed, Inc., Transurethral Needle Ablation (Tuna): Highlights from Worldwide Clinical Studies, Vidamed's Office TUNA System, 2001.
Wasson, Elisa M. et al. The Feasibility of Enhancing Susceptibility of Glioblastoma Cells to IRE Using a Calcium Adjuvant. Annals of Biomedical Engineering, vol. 45, No. 11, Nov. 2017 pp. 2535-2547.
Weaver et al., "A brief overview of electroporation pulse strength-duration space: A region where additional Intracellular effects are expected." Bioelectrochemistry vol. 87, pp. 236-243 (2012).
Weaver, Electroporation: A General Phenomenon for Manipulating Cells and Tissues, Journal of Cellular Biochemistry, 51: 426-435, 1993.
Weaver, et al., Theory of Electroporation: A Review, Bioelectrochemistry and Bioenergetics, vol. 41, pp. 136-160, 1996.
Weaver, J. C., Electroporation of biological membranes from multicellular to nano scales, IEEE Tms. Dielectr. Electr. Insul 10, 754-768 (2003).
Weaver, J.C., "Electroporation of cells and tissues", IEEE Transactions on Plasma Science, 28(1): p. 24-33 (2000).
Weisstein: Cassini Ovals. From MathWorld—A. Wolfram Web Resource; Apr. 30, 2010; http://mathworld.wolfram.com/ (updated May 18, 2011).
Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radio. Feb. 2015; 38(1): 182-190. doi:10.1007/s00270-014-0905-2.
Yang et al., "Dielectric properties of human leukocyte subpopulations determined by electrorotation as a cell separation criterion." Biophysical Journal, vol. 76, pp. 3307-3314 (1999).
Yao et al., "Study of transmembrane potentials of inner and outer membranes induced by pulsed-electric-field model and simulation." IEEE Trans Plasma Sci, 2007. 35(5): p. 1541-1549.
Zhang, Y., et al., MR imaging to assess immediate response to irreversible electroporation for targeted ablation of liver tissues: preclinical feasibility studies in a rodent model. Radiology, 2010. 256(2): p. 424-32.
Co-pending application No. PCT/US19/51731 International Search Report and Written Opinion dated Feb. 20, 2020, 19 pgs.

\* cited by examiner

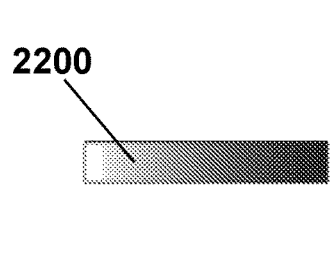 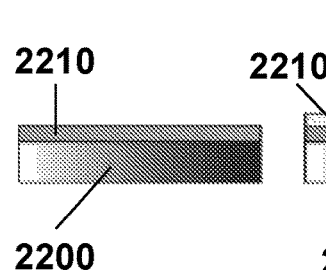 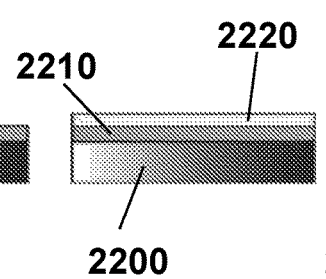 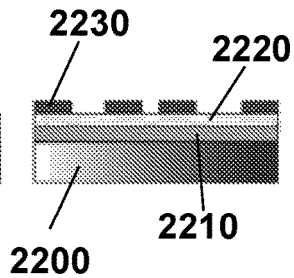
FIG. 22A  FIG. 22B  FIG. 22C  FIG. 22D
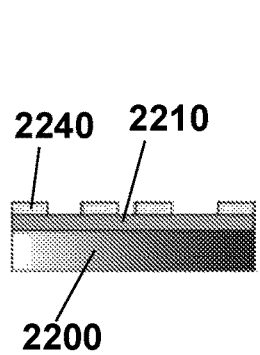 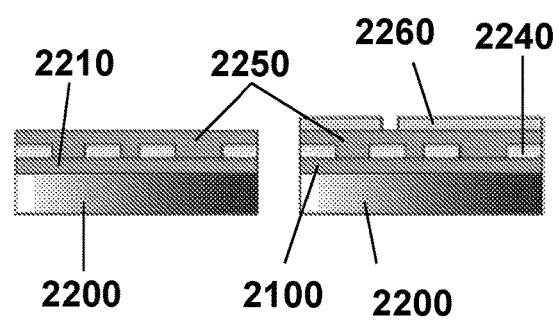 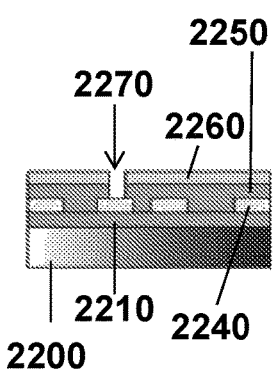
FIG. 22E  FIG. 22F  FIG. 22G  FIG. 22H
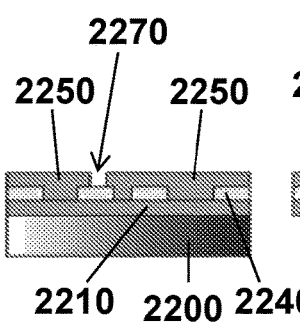 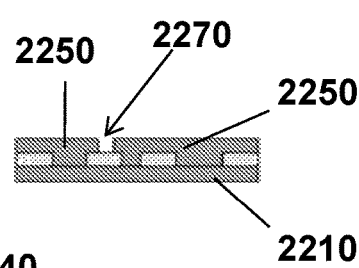
FIG. 22I  FIG. 22J FIG. 26
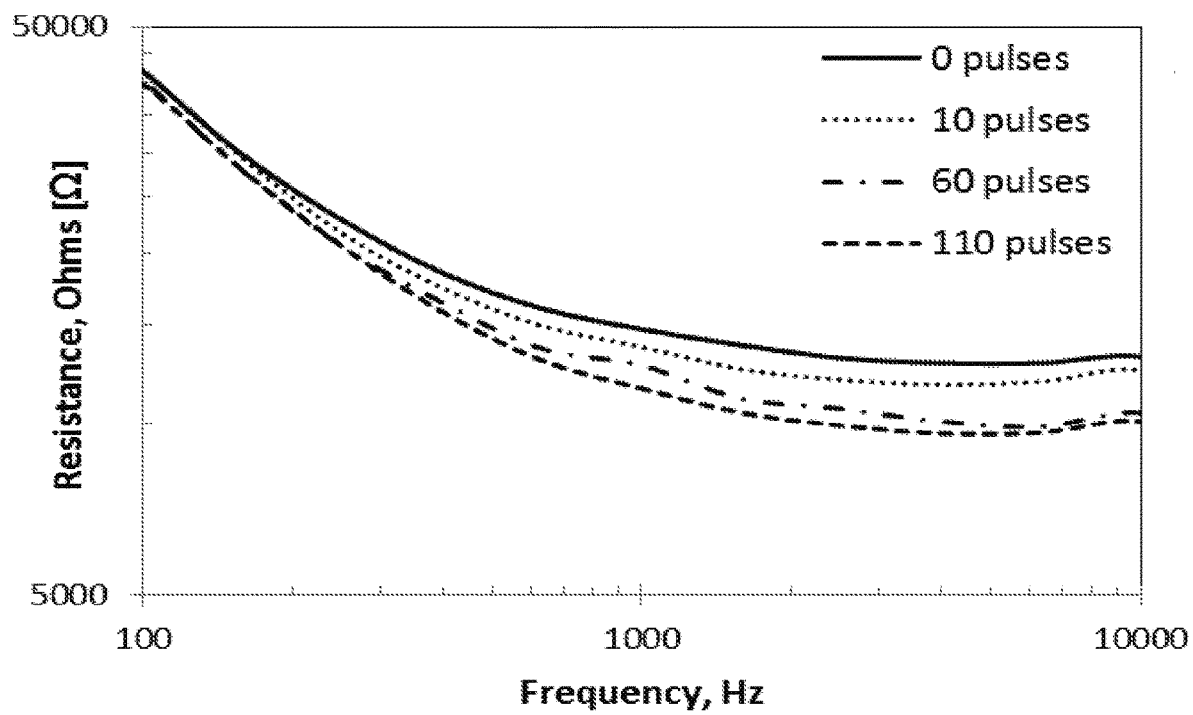
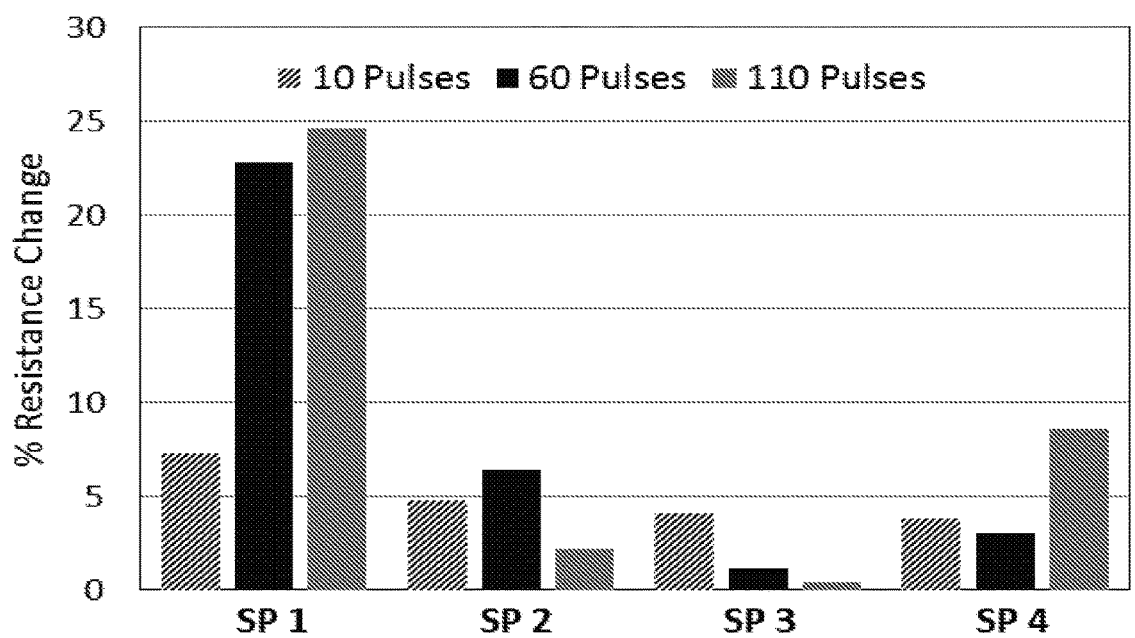
FIG. 27

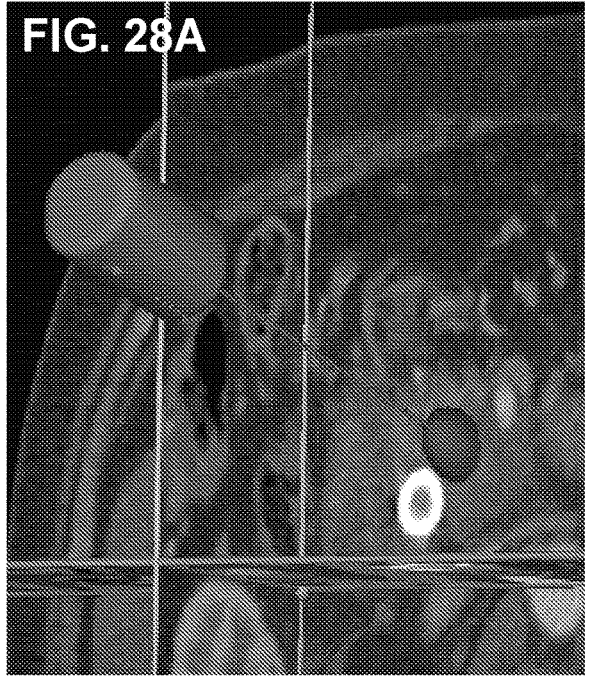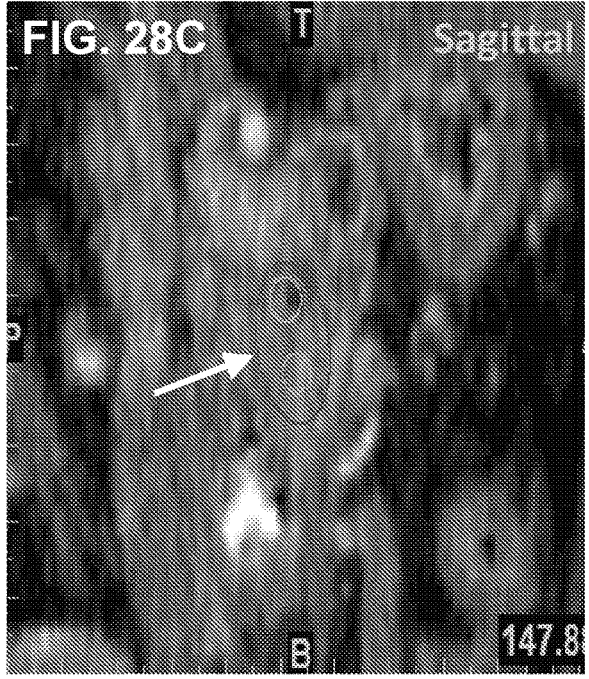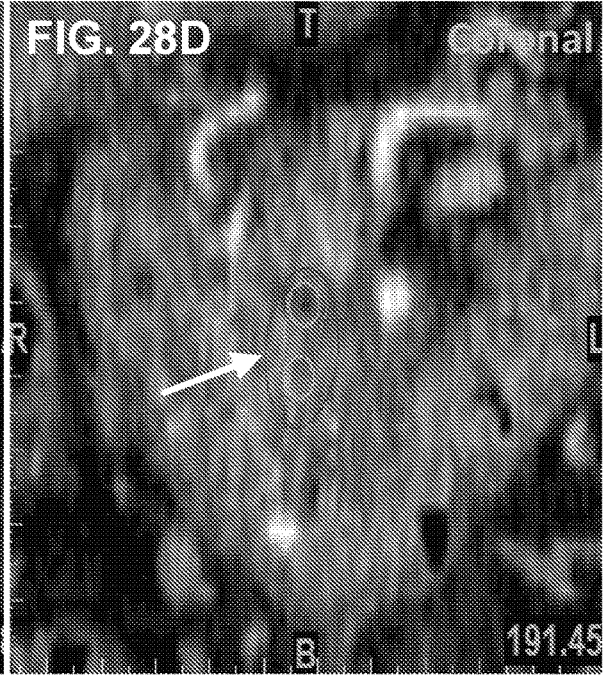

DEVICES, SYSTEMS, AND METHODS FOR REAL-TIME MONITORING OF ELECTROPHYSICAL EFFECTS DURING TISSUE TREATMENT

CROSS-REFERENCE TO RELATED APPLICATIONS

This application is the 35 U.S.C. § 371 national stage application of PCT Application No. PCT/US2015/065792, filed Dec. 15, 2015, where the PCT claims the benefit of U.S. Provisional Application Ser. No. 62/091,703 filed on Dec. 15, 2014 having the title "Real-Time Monitoring of Electrophysical Effects During Tissue Focal Ablation", both of which are herein incorporated by reference in their entireties.

STATEMENT REGARDING FEDERALLY SPONSORED RESEARCH OR DEVELOPMENT

This invention was made with government support under grant number IIP-1026421 awarded by the National Science Foundation. The government has certain rights in the invention.

BACKGROUND

Focal ablation and other cell membrane disruption therapies and molecule delivery mechanisms are used in many clinical and research applications. As such, monitoring techniques for lesion/treatment area are desirable. As such, there exists a need for improved monitoring techniques for use, inter alia, focal ablation and other cell membrane disruption therapies.

SUMMARY

Provided herein are embodiments of an electrical conductivity sensor having an impedance sensor, where the impedance sensor can be configured to measure a low-frequency and a high-frequency impedance and a substrate, where the impedance sensor is coupled to the substrate. The substrate can be flexible. In embodiments, the impedance sensor can contain two or more electrical conductors. The electrical conductors can be in a bipolar configuration. The electrical conductors can be in a tetrapolar configuration. In embodiments, the electrical conductivity sensor can have two impedance sensors that can be coupled to the substrate such that they are orthogonal to each other.

In embodiments, the electrical conductivity sensor can have more than one impedance sensor. In some embodiments, the impedance sensors can be configured in an array. In embodiments having more than one impedance sensor, the electrical conductivity sensor can further contain a common ground, where each impedance sensor is coupled to the common ground. In embodiments having more than one impedance sensor, the electrical conductivity sensor can further contain a common counter electrode, wherein the common counter electrode can be coupled to the substrate.

In embodiments, the impedance sensor(s) can have interdigitated electrodes. In embodiments, the impedance sensor(s) can further contain a receptor molecule configured to specifically bind a target molecule, wherein the receptor molecule is coupled to the sensor(s).

In embodiments, the electrical conductivity sensor can contain one or more sensors configured to detect a tissue characteristic selected from the group of: pH, temperature, a chemical concentration, a nucleic acid concentration, a gas amount, or combinations thereof.

Also provided herein are embodiments of an electrical conductivity probe having an elongated member and an electrical conductivity sensor as described herein where the electrical conductivity sensor can be coupled to the elongated member. In embodiments, the electrical conductivity sensor can be removably coupled to the elongated member.

Also provided herein are embodiments of a system having an electrical conductivity probe as described herein, a treatment probe configured to deliver an energy to a tissue, where the energy can be sufficient to disrupt a cell membrane, an impedance analyzer, where the impedance analyzer can be coupled to the electrical conductivity probe, a low voltage power supply, where the low voltage power supply can be coupled to the electrical conductivity probe and can be configured to deliver a low voltage energy to the electrical conductivity probe, a waveform generator, where the waveform generator can be coupled to the low voltage power supply, a gate driver, where the gate driver can be coupled to the waveform generator and the low voltage power supply, a high voltage switch, where the high voltage switch can be coupled to the treatment probe and the impedance analyzer; and a high voltage power supply, where the high voltage power supply can be coupled to the high voltage switch.

In embodiments, the system can further contain a computer. The computer can be coupled to the impedance analyzer and the computer can contain processing logic that can be configured to determine the position of lesion or treated area front within a tissue undergoing focal ablation/cell membrane disruption therapy. The processing logic can be further configured to generate a signal to a user when the position of lesion or treated area front has reached a predetermined position within the tissue. The processing logic can be configured to automatically manipulate the system to adjust or stop treatment of a tissue by the treatment probe when the position of lesion or treated area front has reached a predetermined position within the tissue.

In embodiments, the treatment probe and the electrical conductivity probe can be the same probe. In embodiments, the treatment probe and the electrical conductivity probe are separate probes. The treatment probe can be coupled to a grounding pad located elsewhere relative to the treatment probe in or on the body of a subject being treated.

Also provided herein are embodiments of a method of monitoring the lesion or treated area front or size during focal ablation or cell membrane disruption therapy, the method have the steps of inserting an electrical conductivity probe as described herein into a tissue, inserting a treatment probe into the tissue, applying a treatment to the tissue, wherein the treatment comprises applying an energy to the tissue via the treatment probe, and measuring a characteristic of the tissue continuously during treatment, determining if there is a change in the tissue characteristic. The characteristic can be impedance. In some embodiments, the step of measuring can include measuring both low-frequency impedance and high-frequency impedance and further comprising the step of stopping or adjusting treatment when low-frequency impedance is equal to high-frequency impedance. In embodiments, the characteristic can be pH, temperature, a gas concentration, a chemical concentration, a nucleic acid concentration, or a combination thereof. In some embodiments, the method can contain the step of stopping or adjusting a treatment when a change in the tissue characteristic is detected. In embodiments, the method can contain the step of alerting a user when a change in the tissue characteristic is detected.

In some embodiments, where the electrical conductivity probe includes an impedance sensor array, the method can include the step of determining the location of the lesion or treated area front or size by comparing impedance data between two or more impedance sensors of the impedance sensor array. In embodiments, the method can include the step of comparing the lesion or treated area front or size to a threshold value and stopping treatment when lesion or treated area front or size is greater than or equal to the threshold value. In embodiments, the method can include the step of comparing the lesion or treated area front or size to a threshold value and alerting a user when lesion or treated area front or size is greater than or equal to the threshold value.

The method can include the steps of comparing measured changes in impedance to a solution for the electric field distribution during focal ablation or cell membrane disruption and determining the 2D/3D lesion or treated area geometry of the lesion or treated area volume. In embodiments, the method can include the step of overlaying the 2D/3D lesion or treated area geometry on one or more medical images of a subject to generate an image overlay. The method can include the step of visualizing lesion or treatment area front migration or lesion or treatment area growth from the image overlay.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 22A-22J shows steps in a process for manufacturing an electrical conductivity sensor.

FIG. 26 shows a graph demonstrating tissue resistance (ohms) after delivery of a series of high-frequency irreversible electroporation (HFIRE) pulses to the porcine liver of FIG. 25B as measured by the probe of FIG. 25A.

FIG. 27 shows a graph demonstrating % change in tissue resistance between varying sensors after delivery of a series of high-frequency irreversible electroporation (HFIRE) pulses to the porcine liver of FIG. 25B as measured by the probe of FIG. 25A.

FIGS. 28A-28D show images of a 3D isometric view of the probe onto ortho-planes from stacked CT images of patient anatomy.

DETAILED DESCRIPTION

Figure 1:
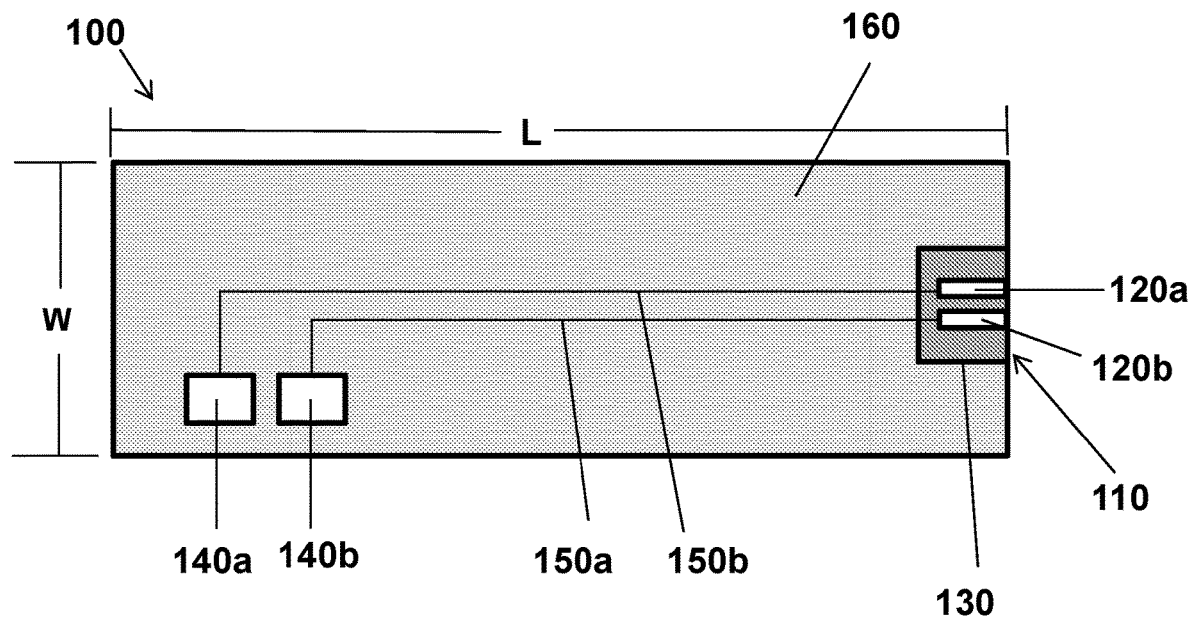
FIG. 1 shows embodiments of an electrical conductivity sensor.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of mechanical engineering, electrical engineering, physiology, medical science, veterinary science, bioengineering, biomechanical engineering, physics, and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within .+-.10% of the indicated value, whichever is greater.

As used herein, "control" is an alternative subject or sample used in an experiment for comparison purposes and included to minimize or distinguish the effect of variables other than an independent variable. A "control" can be a positive control, a negative control, or an assay or reaction control (an internal control to an assay or reaction included to confirm that the assay was functional). In some instances, the positive or negative control can also be the assay or reaction control.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "biocompatible" or "biocompatibility" refers to the ability of a material to be used by a patient without eliciting an adverse or otherwise inappropriate host response in the patient to the material or an active derivative thereof, such as a metabolite, as compared to the host response in a normal or control patient.

As used herein, "therapeutic" can refer to curing and/or treating a symptom of a disease or condition.

The term "treating", as used herein, can include inhibiting and/or resolving the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

The term "preventing", as used herein includes preventing a disease, disorder or condition from occurring in a subject, which can be predisposed to the disease, disorder and/or condition but has not yet been diagnosed as having it. As used herein, "preventative" can refer to hindering or stopping a disease or condition before it occurs or while the disease or condition is still in the sub-clinical phase.

The term "target molecule" can refer to any specific desired molecule including, but not limited to, a nucleic acid, oligonucleotide, polynucleotide, peptide, polypeptide, chemical compound, or other molecule that can specifically bind to a receptor molecule. Typically, the target molecule refers to a molecule that can be located in a sample or tissue whose presence and/or amount can be determined by detecting its binding to known receptor molecule.

The term "receptor molecule" can refer to a molecule that can specifically bind to a target molecule. A receptor molecule can be a nucleic acid, oligonucleotide, polynucleotide, peptide, polypeptide, chemical compound, or other molecule. Receptor molecules can be, for example, antibodies or fragments thereof or aptamers. The receptor molecule can be bound, fixed, or otherwise attached to a surface, sometimes in known location (e.g. as in an array), and can be exposed to a sample such that if a target molecule is present, the target molecule can interact and specifically bind with the receptor molecule. The specific binding can, in some cases, trigger a signal that can provide quantitative and/or qualitative information regarding the target molecule.

As used herein, "specific binding," "specifically bound," and the like, refer to binding that occurs between such paired species as nucleotide/nucleotide, enzyme/substrate, receptor/agonist, antibody/antigen, and lectin/carbohydrate that can be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

Discussion

Focal cell ablation and focal cell membrane disruption techniques can be used to selectively destroy undesired tissue, deliver drugs to cells and tissues, and deliver nucleic acids to cells. Focal ablation and membrane disruption techniques can be thermally or non-thermally based. Thermally based techniques use heat to ablate cells or disrupt cell membranes and include, but are not limited to, radiofrequency (RF) ablation, laser ablation, cryo-ablation, and ultrasound. Other thermal focal ablation/membrane disruption techniques will be appreciated by those of ordinary skill in the art. Non-thermal techniques can rely on the generation or application of an electric field to cells to disrupt (reversibly or irreversibly) the cell membrane, which increases the permeability or kills the cells. Non-thermal focal ablation/membrane disruption techniques include, but are not limited to electroporation. Other Non-thermal focal ablation/membrane disruption techniques will be appreciated by those of ordinary skill in the art. During these techniques, it is difficult to determine the extent of treatment within a tissue being treated. As such, current procedures relying on focal ablation and membrane disruption techniques are imprecise, which can result in undesirable side effects, destruction of, or gene/transcript/protein modification in normal or otherwise healthy cells.

Membrane permeability changes induced by focal ablation/cell membrane disruption techniques at the cell level can translate into changes in impedance at the tissue level. Known devices and methods of monitoring tissue impedance, such as during electroporation, have several drawbacks. Primarily, they rely on bulk tissue properties as opposed to measurements at well-defined points within the tissue being treated. Bulk changes can be useful in describing how the dielectric properties of the tissue change as a whole during treatment. However, there is no specificity in terms of the location where treatment is occurring. In known devices and methods, this information is usually inferred from correlations with predications of the electric field distribution in the tissue. In other words, the treatment zone is defined as the area above a pre-determined threshold that is based on the inferred correlations and predications. The bulk measurements can be made either through the treatment electrodes or with a separate set of electrodes, where the electrodes located in proximity to each other.

As an alternative, electrical impedance tomography (EIT) can be used to map the tissue dielectric potential throughout the entire treatment region based on solutions to a nonlinear inverse that accounts for surface electrical measurements. However, this imaging technique is complicated by the required placement of an electrode array around the periphery of the target tissue. Placement of the electrode array can be difficult to implement clinically because some tumors and other target tissues do not accommodate the placement of such an array due to geometrical/anatomical constraints or the presence of highly insulating anatomical structures such as the skull or skin. Further, EIT suffers from the limitations associated with the resolution of reconstructed images, which relies heavily on the accurate placement and number of external electrodes. Moreover, none of the existing technologies and methods can achieve active, real-time monitoring of the lesion or treated area front during focal ablation and cell membrane disruption procedures.

With these shortcomings in mind, described herein are devices and systems that can be configured to monitor a lesion or treated area front in real-time during focal ablation/membrane disruption therapy. The devices and systems can be configured with a sensor array to detect a lesion or treated area front. The devices and systems provided herein can be used to actively monitor focal ablation/cell membrane disruption therapy in real-time and thus can allow a practitioner to control, adjust, and/or discontinue treatment in response to front migration to minimize treatment side effects.

Also described herein are methods of monitoring a lesion or treated area front in real-time in tissue during focal ablation/membrane disruption. The methods can include alerting a user when the front has reached a desired location. The methods can utilize both low- and high-frequency electrical impedance measurements to determine if the tissue area surrounding a sensor has been ablated or treated. The devices, systems and methods described herein can provide for focal ablation/membrane disruption techniques and therapies with improved specificity than current techniques and devices. Other devices, systems, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Systems and Devices for Real-Time Impedance Monitoring

During focal ablation or cell membrane disruption procedures, as the procedure continues the treated area or lesion expands out from the treatment source. A feature common to these types of therapies is a change in the membrane permeability of the cell membranes that have been stimulated during focal ablation or cell membrane disruption. Focal ablation and other membrane disruption techniques can result in a change in impedance in due to a change in the permeability of the cells that have been sufficiently stimulated during focal ablation or cell membrane disruption.

As the lesion or treated area forms as treatment continues, an increasing number of cells in the tissue surrounding the treatment source undergo a membrane disruption and thus a change in the impedance of the cells in that area. As the lesion/treated area grows, a front can be formed that forms a boundary between treated and untreated cells. The treated cells and the untreated cells can have different impedances or other characteristics (e.g. pH and temperature). By measuring the impedance or other characteristic between two or more points in the tissue during treatment, it can be possible to determine if the front lies between those two points. The position of the lesion/treated area front within a tissue being treated can also be made by measuring impedance or other tissue characteristic at a single point and comparing that to a base line or prior measurement from that point.

Provided herein are systems and devices that can be configured to detect and determine the location of a lesion/treated area front in real-time during a focal ablation or cell membrane disruption therapy. The systems and devices can also be configured to generate 3D images and models from lesion/treated area front measurements that can provide the volume of a lesion/treated area. The systems and devices can be configured to provide automatic control of a treatment in response to detection of the migration of the lesion/treated area front. The systems and devices can be configured to provide a signal to a user in response to detection of the migration of the lesion/treated area front.

Biological tissue is a combination of extracellular space, cellular membranes, and subcellular structures, each of which contains organic molecules and ions in different structural arrangements. This can result in a broad spectrum of dielectric properties across multiple frequencies. In other words, the dielectric properties of tissue are frequency dependent. From around 0.1 Hz to 10 MHz, there exist two main dispersive regions: (1) the $\alpha$, or low frequency, dispersion region and (2) the $\beta$, or high frequency, region. The $\alpha$ region ranges from about 0.1 Hz to about 10 Hz and the $\beta$ region ranges from about 0.1 MHz to about 10 MHz. The $\alpha$ region is due to counter ion polarization effects along cell membranes. The $\beta$ region is due to the Maxwell-Wagner effects. This describes the charging and relaxation effects along cell membranes, which act as barriers to the movement of ions.

Above the $\beta$ dispersion, cell membranes have negligible impedance and current can pass freely through the cell membrane. This is similar to what happens during, for example, electroporation, when pore formation reduces the membrane impedance and permits current to enter the cell. As a result, low frequency ($\alpha$ region) electrical measurements at a location in a tissue before and after focal ablation or cell membrane disruption can be compared to determine if the focal ablation or cell membrane disruption has reached its endpoint at that position in the tissue. At the endpoint, the low frequency ($\alpha$ region) impedance is about equal to the high-frequency ($\beta$ region) impedance, which is due to the focal ablation or cell membrane disruption in that region of the tissue. Stated differently, in a formed lesion or treated area, the low frequency ($\alpha$ region) impedance is about equal to the high-frequency ($\beta$ region) impedance. Thus, comparison of the low frequency ($\alpha$ region) impedance and the high-frequency ($\beta$ region) impedance can be used to determine lesion formation in that area of tissue due to focal ablation/cell membrane disruption treatment.

In some embodiments, the systems and devices can be configured to detect a focal ablation or cell membrane disruption in treatment area by simultaneously measuring both a region and $\beta$ region impedance in a tissue. The systems and devices described herein can be configured to monitor, in real-time, the size of a treated area during a focal ablation or cell membrane disruption procedure. The devices and systems can contain an electrical conductivity sensor, which can contain an impedance sensor or impedance sensor array. The electrical conductivity sensor can be configured to measure both low-frequency ($\alpha$ region) impedance and high-frequency ($\beta$ region) impedance. The electrical conductivity sensor can be integrated with or operatively coupled to an electrical conductivity probe and/or be integrated with or operatively coupled to a treatment probe.

Electrical Conductivity Sensors

With a general description in mind, attention is directed to FIGS. 1-8, which show embodiments of electrical conductivity sensors that can be configured to measure tissue impedance, a change in tissue impedance between points in a tissue, migration of a lesion/treated area front, and/or both low-frequency ($\alpha$ region) impedance and high-frequency ($\beta$ region) impedance.

Discussion begins with FIG. 1, which shows one embodiment of an electrical conductivity sensor 100 that can be configured to measure a change in tissue impedance between points in a of tissue, and/or both low-frequency ($\alpha$ region) impedance and high-frequency ($\beta$ region) impedance. The electrical conductivity sensor 100 can have an impedance sensor 110 at least two electrical conductors 120 $a,b$ (collectively 110). In some embodiments, the impedance sensor 110 can have an even number of electrical conductors 120. In some embodiments the impedance sensor 110 can have 2, 3, 4, 5, 6, 7, 8, 9, 10 or more electrical conductors 120. In some embodiments, the impedance sensor 110 can be configured to measure impedance using a bipolar configuration of electrodes 120 (see e.g. FIG. 1). In other embodiments, the impedance sensor 110 can be configured to measure impedance using a tetrapolar configuration (see e.g. FIG. 3). It will be appreciated that the sensor electrodes, in any given configuration, can be separate from any source and sink electrodes that can be used for delivering the focal ablation/cell membrane disruption therapy.

The electrical conductors 120 can be coupled to bonding pads 140 $a,b$ (collectively 140). In some embodiments, each electrical conductor 120 is coupled to an individual bonding pad 140. The electrical conductors 120 can be coupled to the bonding pad(s) 140 via electrical leads 150 $a,b$ (collectively 150). The electrical conductor 120, the bonding pad(s) 140, and the lead(s) 150 can be coupled to a substrate 160. In some embodiments, the electrical conductors 120 can be coupled to an impedance sensor substrate 130. The impedance sensor substrate 130 can be coupled to the substrate 160. In some embodiments, the electrical conductors 120 can be attached directly to the substrate 160. The electrical conductivity sensor 100 can be configured such that at least a portion of one or more of the electrodes is exposed to the tissue when in use.

The electrical conductivity sensor 100 can have a length (l), a width (w), and a thickness. The length can range from about 1 mm to 1000 mm or more. The width can range from about 0.1 mm to about 50 mm or more. The thickness can range from about 0.1 micron to about 1000 microns or more.

Figure 2:
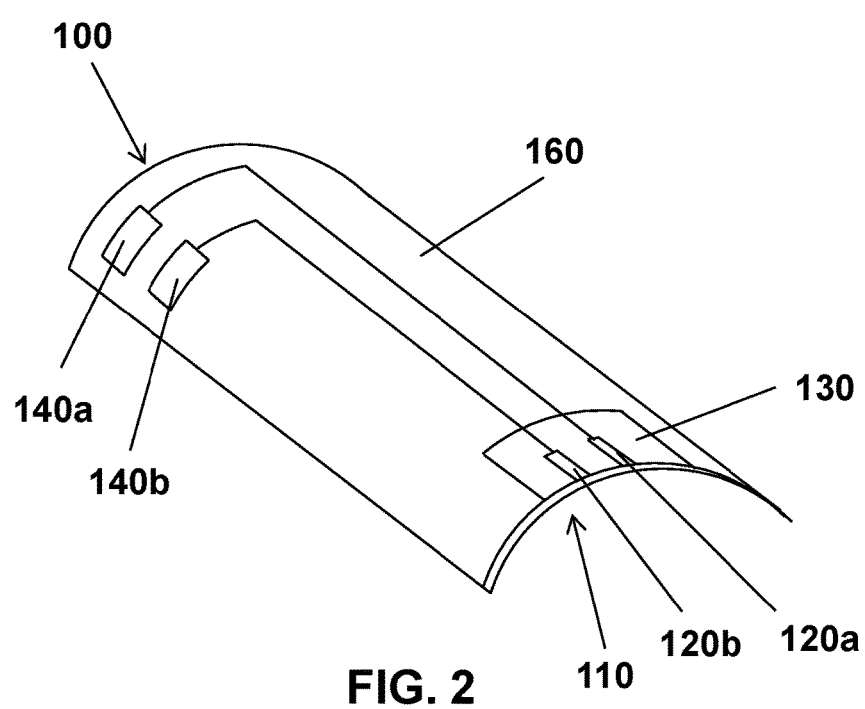
FIG. 2 shows embodiments of an electrical conductivity sensor.

As shown in FIG. 2, the electrical conductivity sensor 100 can be flexible. The substrate 160 and the optional impedance sensor substrate 130 can be made out of any suitable material. The material can be biocompatible. Suitable materials include, but are not limited to ceramics (porcelain, alumina, hydroxyapatite, zirconia), polymers (e.g. thermoplastic elastomers (e.g. silicone elastomers, styrene block copolymers, thermoplastic copolyesters, thermoplastic polyesters, thermoplastic polyamides, thermoplastic polyolefins, thermoplastic polyurethanes, thermoplastic vulcanizates), polyvinyl chloride, fluoropolymers (PTFE, modified PTFE, FEP, ETE, PFA, MFA), polyurethane, polycarbonate, silicone, acrylics, polypropylene, low density polyethylenes, nylon, sulfone resins, high density polyethylenes, natural polymers (cellulose, rubber, alginates, carrageenan), polyimide, polyether ether ketone), metals (e.g. gold, silver, titanium, platinum), metal alloys (e.g. stainless steel, cobalt alloys, titanium alloys), glass, and combinations thereof.

The leads 150, bonding pads 140 and electrical conductors 120 can be made of a suitable conductive or semi-conductive material. The material can be flexible. The materials can be biocompatible. Suitable conductive and semi-conductive materials include, without limitation, gold, silver, copper, aluminum, nickel, platinum, palladium, zinc, molybdenum, tungsten, graphite, Indium tin oxide, conductive organic polymers (e.g. polyacetylene, polyphenylene vinylene, polypyrrole, polythiophene, polyaniline, and polyphenylene sulfide), silicon, germanium, cadmium, indium, and combinations thereof.

Figure 3:
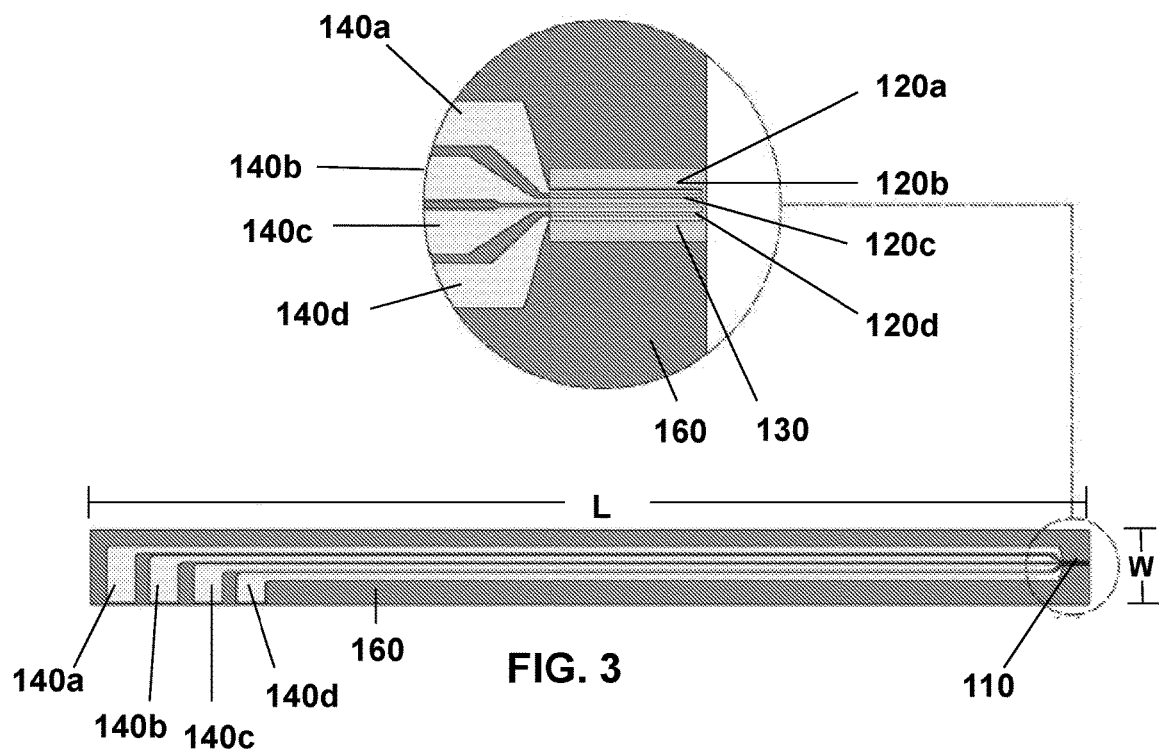
FIG. 3 shows embodiments of an electrical conductivity sensor.

In operation, a known electrical current can be passed through at least one of the electrical conductors 120. A voltage is then induced in at least one of the other electrical conductors 120 As such, in embodiments, where there are only two electrical conductors 120 (a bipolar configuration) (see e.g. FIG. 1), a known current can be passed through one electrical conductor (120a) and a voltage is then induced in the other electrical conductor (120b). As shown in FIG. 3, where there are more than two electrical conductors 120 a-d (e.g. a tetrapolar configuration), a current can be passed through the outer most electrical conductors 120 a,d and the induced voltage across the inner electrical conductors 120 b,c can be measured. Other suitable configurations will be appreciated by those of skill in the art. In any embodiment, the high-frequency and low frequency impedance can be measured from the induced voltages. As described elsewhere herein, the high-frequency and low-frequency impedance can be used to determine if a particular region of tissue has been treated and/or the area and/or volume of tissue that has been effectively treated.

Some tissues have anisotropic electrical properties, which can be due to the directional growth of the cell. As such, in some instances it is desirable to measure the electrical conductivities in two orthogonal directions. With this in mind, attention is directed to FIG. 4, which shows an embodiment of an electrical conductivity sensor configured to measure both high- and low-frequency impedance in two orthogonal directions.

Figure 4:
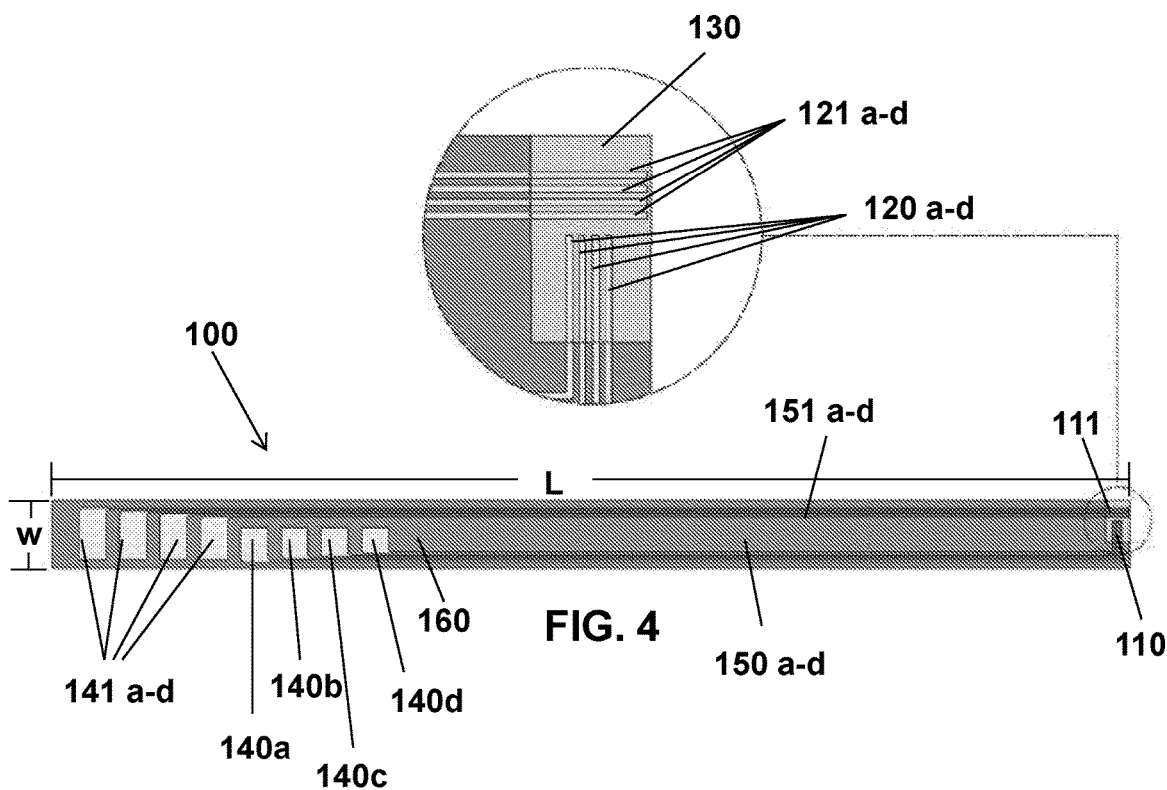
FIG. 4 shows embodiments of an electrical conductivity sensor.

As shown in FIG. 4, the electrical conductivity sensor can have at least two impedance sensors 110 and 111. The first impedance sensor 110 can have a first set of electrical conductors 120 a-d. The second impedance sensor 111 can have a second set of electrical conductors 121 a-d. The first 120 and second 121 sets of electrical conductors can be coupled to a substrate 160 and/or impedance sensor substrate 130 such that the first set of electrical conductors 120 and the second set of electrical conductors 121 are orthogonal to each other. In this way, the first 110 and the second 111 impedance sensors can be said to be orthogonal to each other in these embodiments.

While FIG. 4 shows the impedance sensors 110, 111 in a tetrapolar configuration it will be appreciated by those of skill in the art that they can be configured in any suitable manner, for example, as previously described with respect to FIGS. 1-3. Likewise, each impedance sensor 110, 111 can have at least two electrical conductors 120, 121. In some embodiments, each impedance sensor 110,111 can have 3, 4, 5, 6, 7, 8, 9, 10 or more electrical conductors. The impedance sensors 110, 111 can have the same number or a different number of electrical conductors 120, 121 as each other. The dimensions of these embodiments of the electrical conductivity sensor 100 can be as described with respect to FIGS. 1-3 above. The electrical conductivity sensor 100 and components thereof can be made from suitable materials as previously described with respect to FIGS. 1-3. As previously described, each electrical conductor 120, 121, can be coupled to a bonding pad 140 a-d and 141 a-d via an electrical leads 150 a-d and 151 a-d. The operation of each set of electrodes 120, 121 to measure impedance can be as described with respect to FIGS. 1-3 above.

FIGS. 1-4 demonstrate embodiments of an electrical conductivity sensor 100 that contain electrical conductors at a single location on the electrical conductivity sensor 100. As described elsewhere herein it can be desirable to measure the size of a treatment area in a tissue during focal ablation/cell membrane disruption therapy. During therapy, the lesion formed will grow in size, and as such, it can be desirable to measure this growth without the need for repositioning the electrical conductivity sensor, or probe that it can be coupled to, during treatment.

With this in mind, attention is directed to FIGS. 5-8 which show embodiments of an electrical conductivity sensor 100 that has a sensor array. The electrical conductivity sensor 100 having a sensor array can be configured to measure impedance. In some embodiments, the electrical conductivity sensor 100 having a sensor array 200 can be configured to detect both high- and low-frequency impedance having an impedance sensor array 200. In some embodiments the sensor array 200 can be configured to detect another tissue characteristic, including but not limited to, pH, temperature, drug concentration, chemical concentration, gas concentration and combinations thereof. As such, in some embodiments, the lesion/treated area front can be determined by measuring these characteristics.

Figure 5:
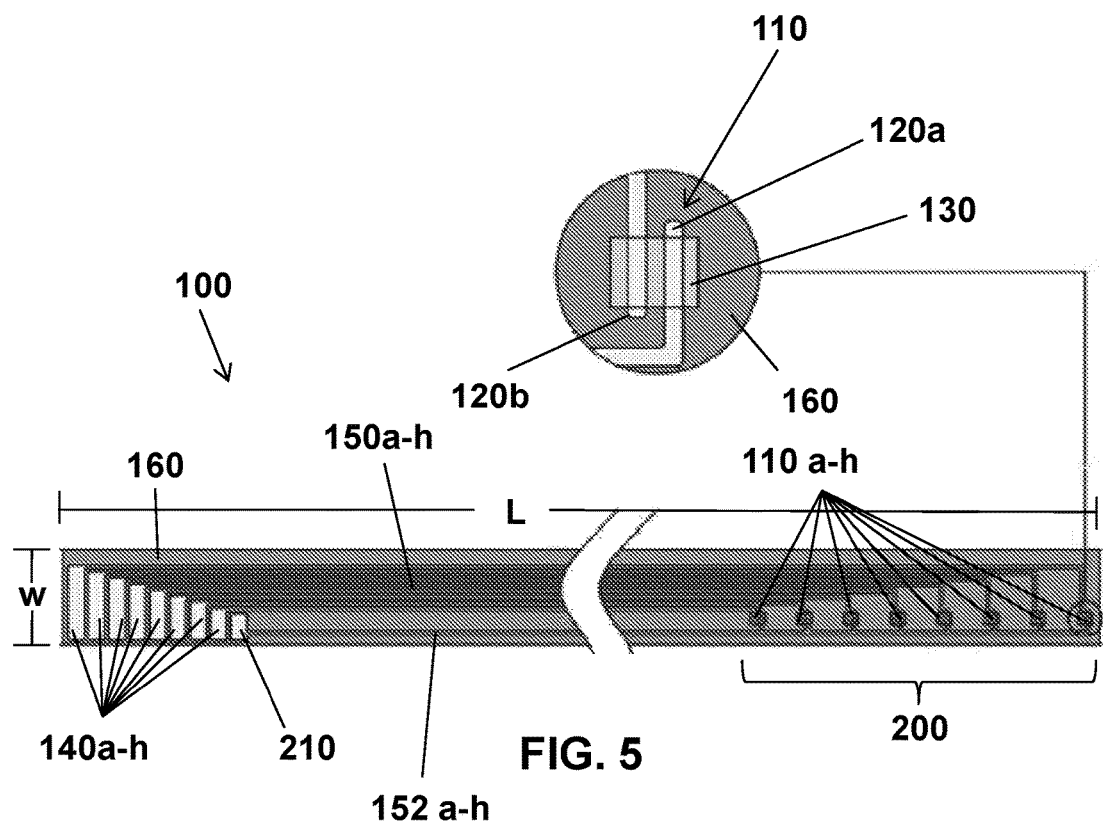
FIG. 5 shows embodiments of an electrical conductivity sensor.

Discussion continues with FIG. 5 which shows one embodiment of an electrical conductivity sensor 100 having an impedance sensor array 200. In the embodiments depicted by FIG. 5, the impedance sensor array 200 has at least two impedance sensors 110 a-h. While FIG. 5 shows an impedance sensor array 200 having eight (8) impedance sensors 110, it will be appreciated that the impedance sensor array 200 can have 2, 3, 4, 5, 6, 7, 8, 9, 10, 11, 12, 13, 14, 14, 16, 17, 18, 19, 20 or more impedance sensors 110. Each impedance sensor 110 can be coupled to a bonding pad 140 a-h and a common ground 210 via electrical leads 150 a-h and 152 a-h. While FIG. 5 shows an impedance sensor array 200 having eight (8) bonding pads 140, it will be appreciated that the impedance sensor array 200 can have 2, 3, 4, 5, 6, 7, 8, 9, 10, 11, 12, 13, 14, 14, 16, 17, 18, 19, 20 or more bonding pads 140. The dimensions of these embodiments of the electrical conductivity sensor 100 can be as described with respect to FIGS. 1-3 above. The electrical conductivity sensor 100 and components thereof can be made from suitable materials as previously described with respect to FIGS. 1-3. In some embodiments, the electrical conductivity sensor 100 having an impedance sensor array 200 can contain include two current injection electrodes on either end of the electrode array.

Measurement of low-frequency and/or high-frequency impedance of each impedance sensor 110 of the impedance sensor array 200 can be as previously described with respect to FIGS. 1-3. Further, differences in impedance measurements between two or more different impedance sensors 110 of the impedance sensor array 200 can be determined. In this way it is possible to determine the extent of the lesion formed by focal ablation/cell membrane disruption therapy. Stated differently, the change in the electrical impedance of different combinations of impedance sensors 110 of the impedance sensor array 200 can be evaluated and the lesion size, and/or lesion/treated area front can be determined based on the impedance or other tissue characteristic measurements evaluated. This is discussed in greater detail elsewhere herein.

In some embodiments, the sensors 110 can be functionalized with one or more receptor molecules configured to specifically bind a target molecule. This can make the impedance measurement more selective toward identification of certain intracellular substances, including proteins and ions that are released during electroporation. This modification can enhance the capability of the sensor to detect the lesion front.

Figure 6:
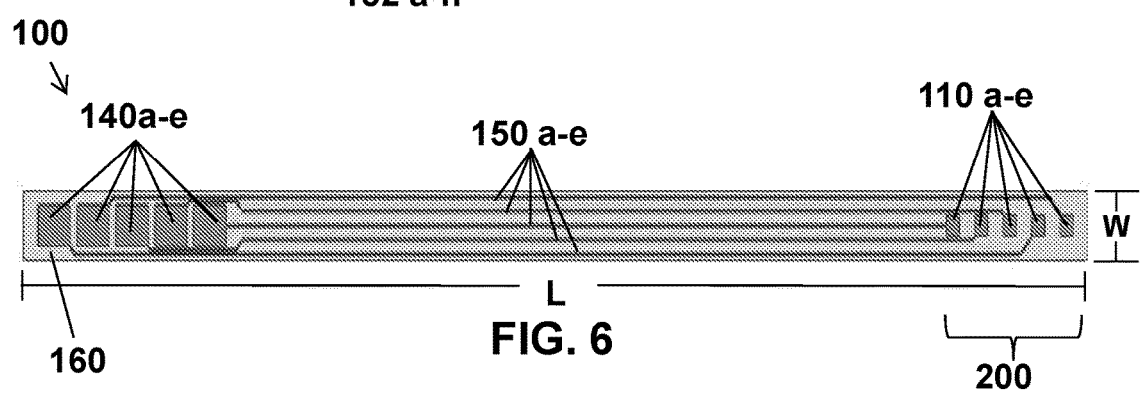
FIG. 6 shows embodiments of an electrical conductivity sensor.

FIG. 6 shows another embodiment of an electrical conductivity sensor 100 having an impedance sensor array 200. The impedance sensor array 200 has at least two impedance sensors 110 *a-e*. While FIG. 6 shows an impedance sensor array 200 having five (5) impedance sensors 110, it will be appreciated that the impedance sensor array 200 can have 2, 3, 4, 5, 6, 7, 8, 9, 10, 11, 12, 13, 14, 14, 16, 17, 18, 19, 20 or more impedance sensors 110. Each impedance sensor 110 can be coupled to a bonding pad 140 *a-e* via electrical leads 150 *a-e*. While FIG. 6 shows an impedance sensor array 200 having five (5) bonding pads 140, it will be appreciated that the impedance sensor array 200 can have 2, 3, 4, 5, 6, 7, 8, 9, 10, 11, 12, 13, 14, 14, 16, 17, 18, 19, 20 or more bonding pads 140. The electrical impedance measured by any combination of impedance sensors can be determined and correlated to the lesion size. The dimensions of these embodiments of the electrical conductivity sensor 100 can be as described with respect to FIGS. 1-3 above. The electrical conductivity sensor 100 and components thereof can be made from suitable materials as previously described with respect to FIGS. 1-3.

Figure 7:
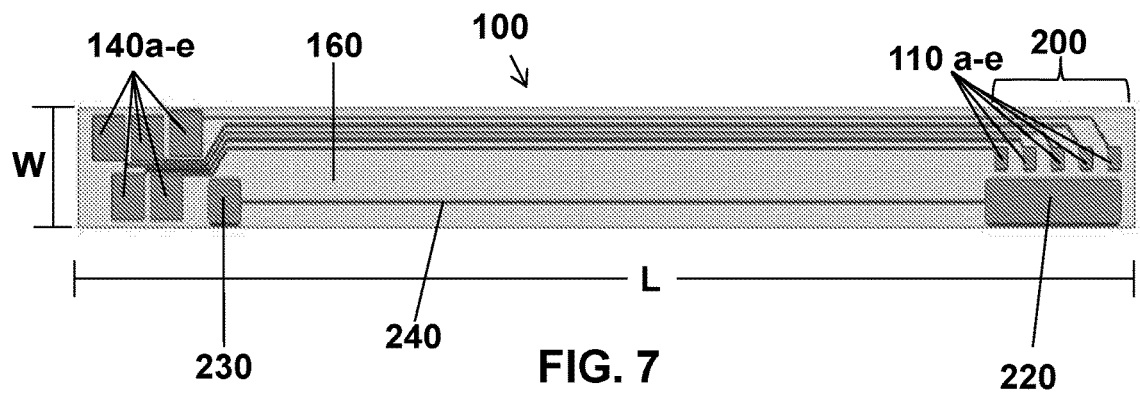
FIG. 7 shows embodiments of an electrical conductivity sensor.

FIG. 7 shows further embodiments of an electrical conductivity sensor 100 having an impedance sensor array 200. These embodiments are the same as those described in relation to FIG. 6 except that they further contain a common counter electrode 220. The common counter electrode 220 can be coupled to the substrate 160. The common counter electrode 220 can be coupled to a bonding pad 230 via an electrical lead 240, which both can also be coupled to the substrate 160. In operation, all impedances measured by the impedance sensors 110 of the impedance sensor array 220 can be measured with respect to the common counter electrode 220. It will be appreciated that a common counter electrode can also be used in embodiments described in FIG. 5. The dimensions of these embodiments of the electrical conductivity sensor 100 can be as described with respect to FIGS. 1-3 above. The electrical conductivity sensor 100 and components thereof can be made from suitable materials as previously described with respect to FIGS. 1-3.

Figure 8:
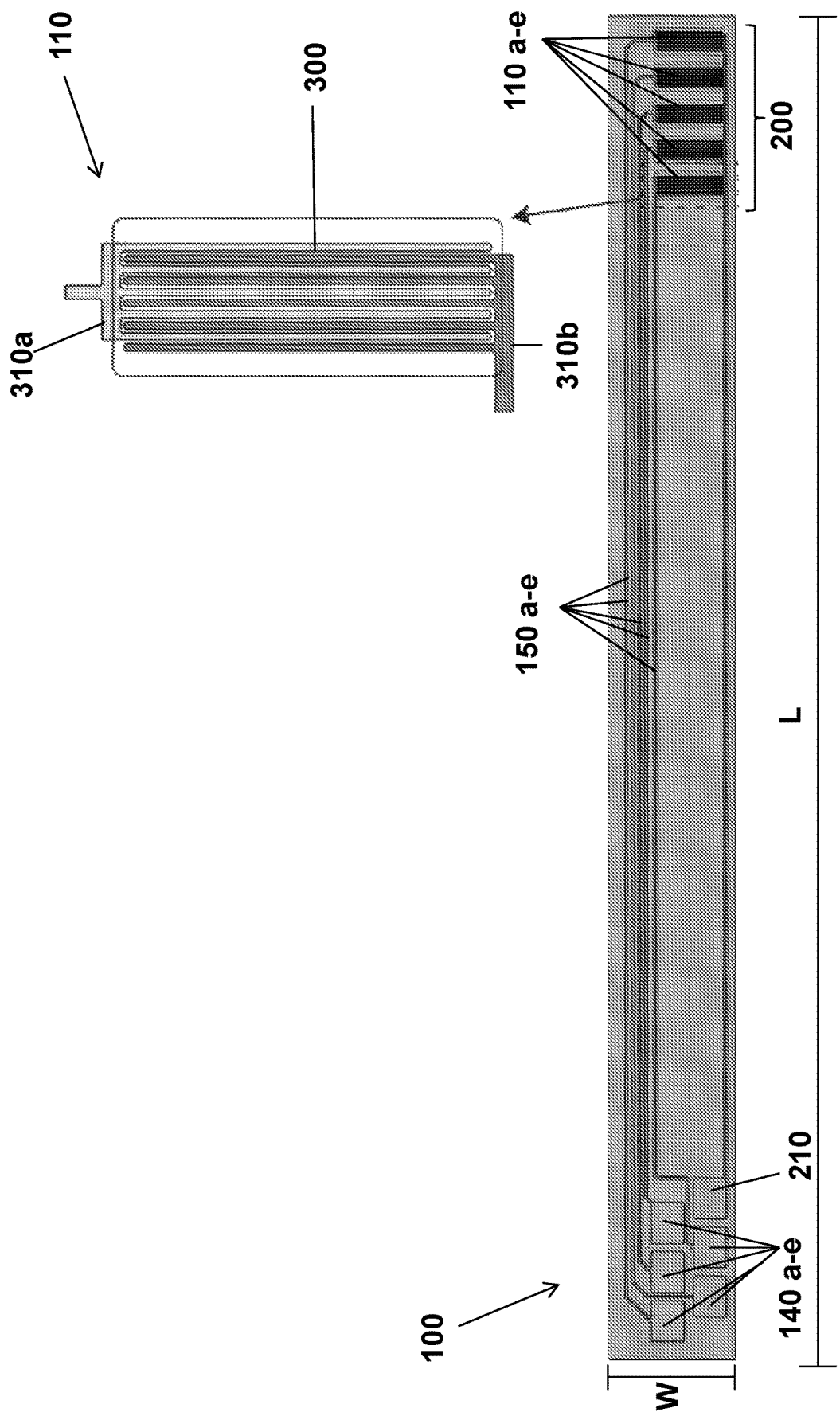
FIG. 8 shows embodiments of an electrical conductivity sensor.

FIG. 8 shows further embodiments of an electrical conductivity sensor 100 having an impedance sensor array 200. The impedance sensor array 200 can contain impedance sensors 110 having interdigitated electrodes 300. In embodiments, the impedance sensor can have a pair of electrode sets 310 *a,b* (collectively 310), where each electrode set has an even number of electrodes (e.g. 2, 4, 6, 8, 10 etc.) and can be interdigitated with each other as shown in FIG. 8. This interdigitated configuration can increase the sensitivity of the impedance sensor 110. While not being bound to theory, it is believed that the increase in sensitivity can be attributed to the increased current density across the interdigitated pair of electrode sets 310 relative to a non-interdigitated electrode set.

While FIG. 8 shows an impedance sensor array 200 having five (5) impedance sensors 110, it will be appreciated that the impedance sensor array 200 can have 2, 3, 4, 5, 6, 7, 8, 9, 10, 11, 12, 13, 14, 14, 16, 17, 18, 19, 20 or more impedance sensors 110. The impedance sensors 110 can be coupled to a substrate 160 as previously described in relation to e.g. FIGS. 5-7. Each impedance sensor 110 can be coupled to a bonding pad 140 via electrical leads 150 *a-e*. While FIG. 8 shows an impedance sensor array 200 having five (5) bonding pads 140, it will be appreciated that the impedance sensor array 200 can have 2, 3, 4, 5, 6, 7, 8, 9, 10, 11, 12, 13, 14, 14, 16, 17, 18, 19, 20 or more bonding pads 140. In some embodiments, the impedance sensors can all be coupled to a common ground 210 as previously described with respect to FIG. 5. In further embodiments, the electrical conductivity sensor 100 having an impedance sensors 110 with interdigitated electrodes 300 can further contain a common counter electrode 230, which can be configured as shown and described with respect to FIG. 7 The dimensions of these embodiments of the electrical conductivity sensor 100 can be as described with respect to FIGS. 1-3 above. The electrical conductivity sensor 100 and components thereof can be made from suitable materials as previously described with respect to FIGS. 1-3.

In some embodiments, the electrical conductivity sensor 100 as described in relation to any of FIGS. 1-8 can further contain one or more additional sensors to measure additional tissue characteristics. Additional sensors include, but are not limited to, pH sensors, temperature sensors, chemical sensors, and gas (e.g. $CO_2$, NO, $O_2$) sensors. There can be 1, 2, 3, 4, 5, 6, 7, 8, 9, 10 or more additional sensors. The additional sensors can also be configured as an array akin to the impedance sensor array on the electrical conductivity sensor 100. The additional sensor(s) can be coupled to the substrate 160. The additional sensors can be coupled to one or more additional bonding pads via leads as will be appreciated by those of skill in the art.

The electrical conductivity sensor 100 and/or any component(s) thereof as described in relation to any of FIGS. 1-8 can be disposable, reusable, recyclable, biocompatible, sterile, and/or sterilizable.

The electrical conductivity sensor 100 and components thereof described herein can be manufactured by any suitable method and in any suitable way. Suitable methods include, but are not limited to, injection molding, 3-D printing, glass/plastic molding processes, optical fiber production process, casting, chemical deposition, electrospinning, machining, die casting, evaporative-pattern casting, resin casting, sand casting, shell molding, vacuum molding, thermoforming, laminating, dip molding, embossing, drawing, stamping, electroforming, laser cutting, welding, soldering, sintering, bonding, composite material winding, direct metal laser sintering, fused deposition molding, photolithography, spinning, metal evaporation, chemical etching and sterolithography. Other techniques will be appreciated by those of skill in the art.

Electrical Conductivity Probes

Figure 9:
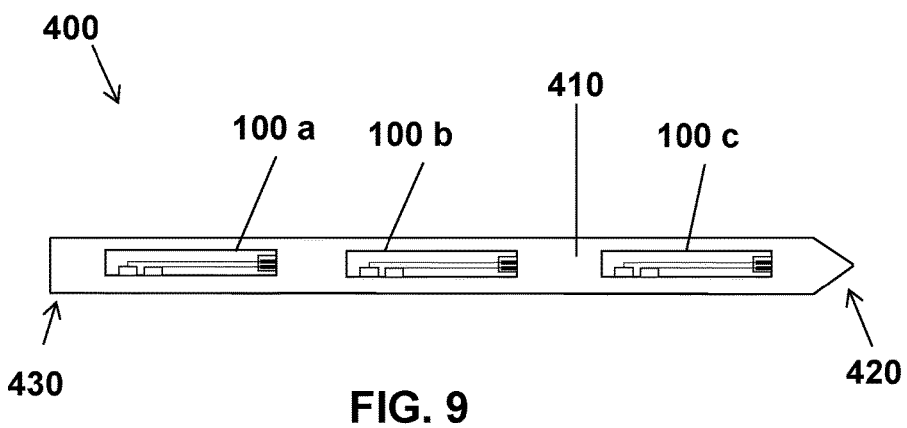
FIG. 9 shows embodiments of an electrical conductivity probe.
Figure 10:
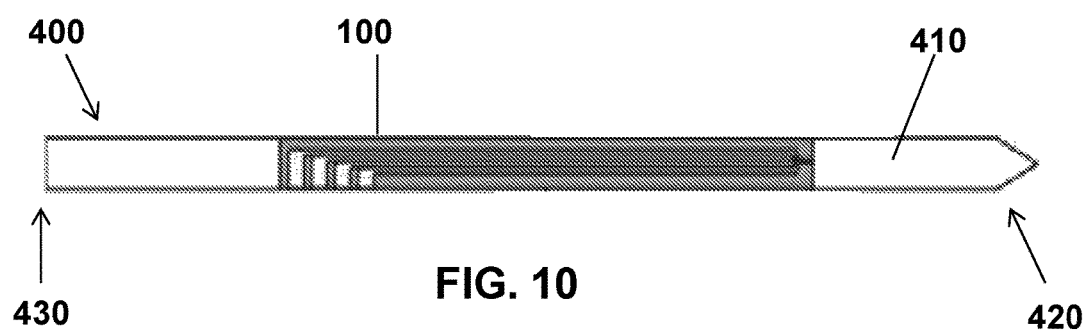
FIG. 10 shows embodiments of an electrical conductivity probe.
Figure 11:
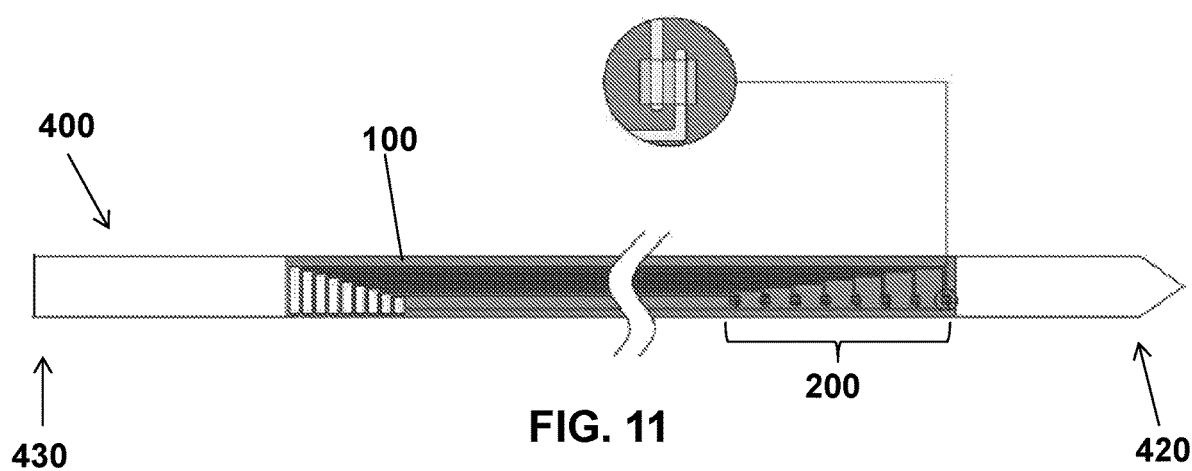
FIG. 11 shows embodiments of an electrical conductivity probe.

The electrical conductivity sensors 100 described in relation to FIGS. 1-8 can be coupled to or integrated with a probe. In some embodiments, the probe can be a treatment probe (i.e. the probe delivering the focal ablation/cell membrane disruption therapy). The probe that contains the electrical conductivity sensor 100 can be separate from the treatment probe. With the general concept in mind, attention is directed to FIGS. 9-11, which show various embodiments of probes including electrical conductivity sensors 100 as described in relation to FIGS. 1-8. As shown in FIGS. 9-11, which show embodiments of an electrical conductivity probe 400 having one or more electrical conductivity sensor 100 *a,b,c* (collectively 100). The electrical conductivity sensor(s) 100 can be any electrical conductivity sensor described in relation to FIGS. 1-8.

The electrical conductivity probe 400 can have an elongated member 410 having a distal portion 420 and a proximal portion 430. The elongated member 400 can be any three dimensional shape, including but not limited to, an irregular shape, a cylinder, a cannula, a cuboid, and a triangular prism. The elongated member 400 can have a width. The width can range from about 0.1 mm to about 10 mm or more. The elongated member can have a length. The length can range from about 5 mm to about 50 cm or more.

The elongated member can have a diameter. The diameter can range from about 10 microns to about 10 mm or more. The distal portion can have a tapered, beveled, pointed, blunt, sharp, rounded, or flat end. Other configurations for the elongated member will be appreciated by those of skill in the ar. At least one electrical conductivity sensor 100 a,b,c (collectively 100) coupled to or otherwise integrated with an outer surface of the elongated member. In some embodiments, 1, 2, 3, 4, 5, 6, 7, 8, 9, 10 or more electrical conductivity sensors 100 can be coupled to the elongated member 410. In some embodiments the electrical conductivity sensor(s) 100 can be removably coupled to the elongated member 410. The electrical conductivity sensor(s) 100 can be electrically coupled to the elongated member 410. The electrical conductivity sensor(s) 100 can be coupled to the elongated member in any desired configuration, e.g. linearly, radially, and the like, as will be appreciated by those of skill in the art.

The electrical conductivity probe 400 can include sensors configured to detect tissue characteristics (e.g. pH, temperature, chemical, gas sensors) and circuitry as needed. In some embodiments, the electrical conductivity probe 400 can be configured to deliver an energy to result in focal ablation/cell membrane disruption in a tissue. Stated differently, the electrical conductivity probe 400 can also be a treatment probe in some embodiments. In other embodiments, the electrical conductivity probe 400 can be separate from a treatment probe. The electrical conductivity probe 400 and/or components thereof can be disposable, reusable, recyclable, biocompatible, sterile, and/or sterilizable.

Figure 12:
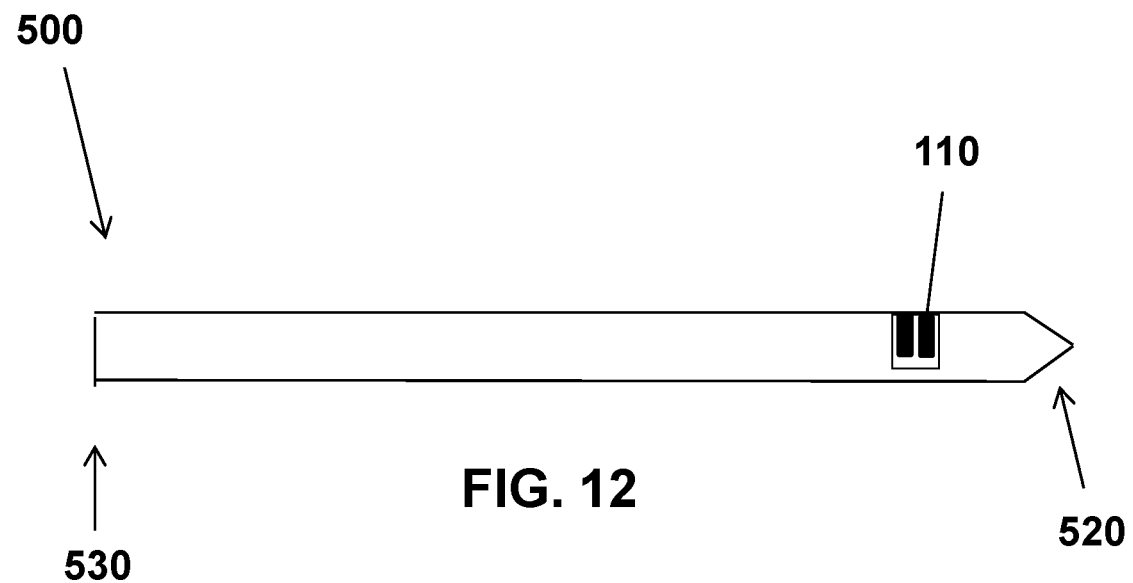
FIG. 12 shows embodiments of an electrical conductivity probe.
Figure 13:
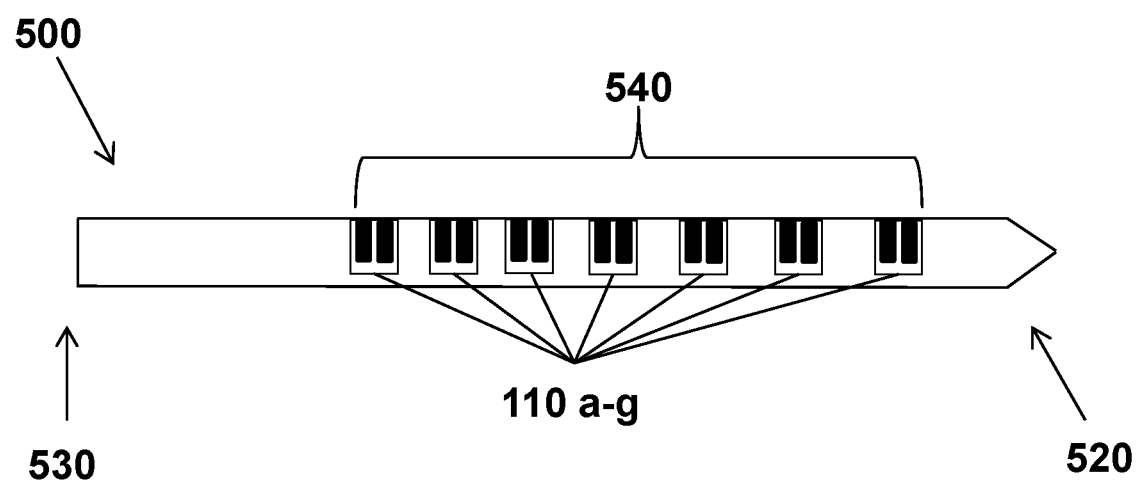
FIG. 13 shows embodiments of an electrical conductivity probe.
Figure 14:
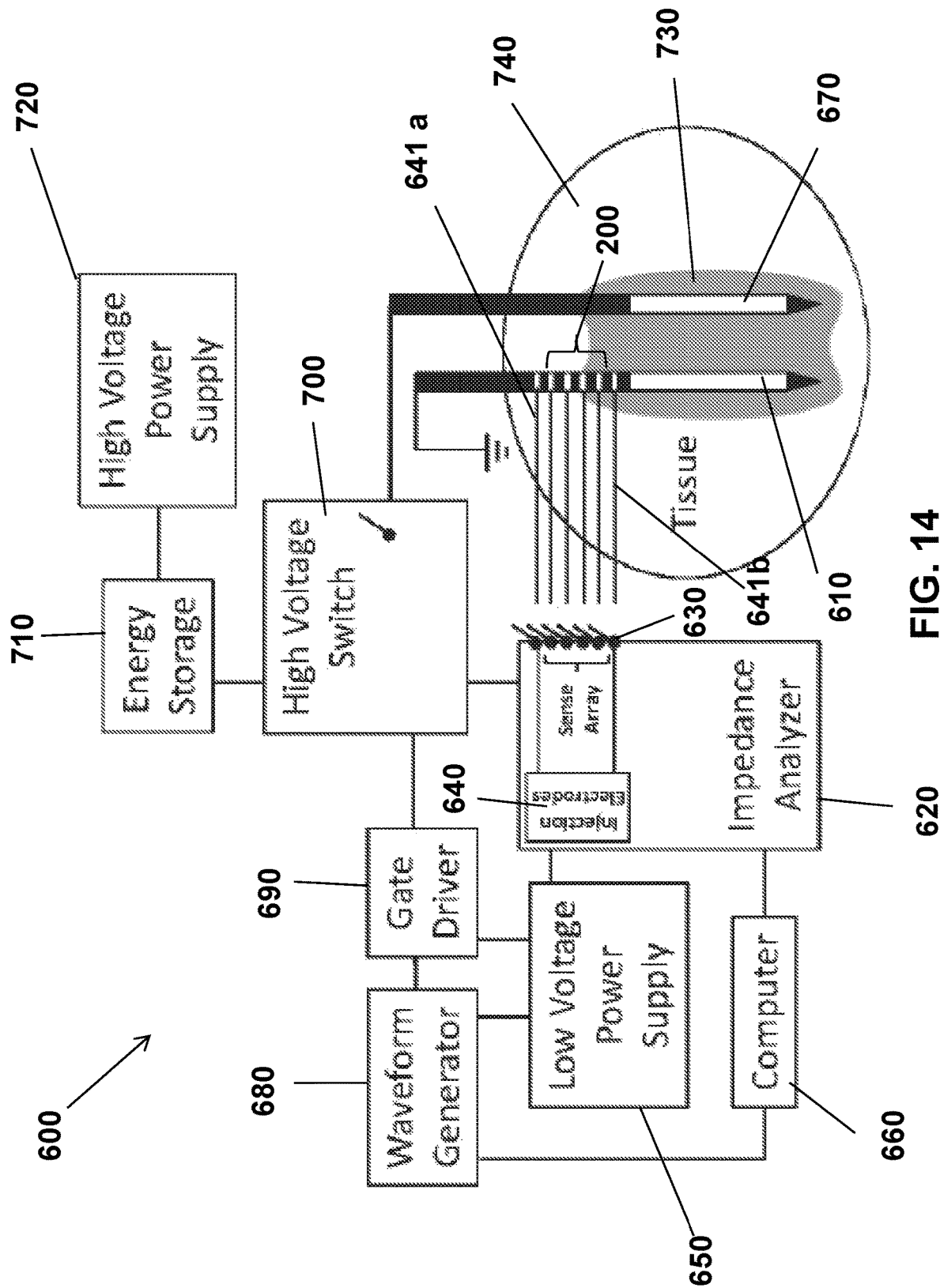
FIG. 14 shows embodiments of a system configured to monitor lesion/treated area formation in real-time.

In some embodiments, the impedance sensors and impedance sensor arrays can be integrated directly with an elongated member 510 of an electrical conductivity probe 500. In other words, the impedance sensor and impedance sensor arrays and associated circuitry are not coupled to a substrate (e.g. 160, FIGS. 1-8), but rather directly integrated with an elongated member 510 of a probe. With this in mind attention is directed to FIGS. 12-13, which show embodiments of an electrical conductivity probe 500 having one (FIG. 12) or more (FIG. 13) impedance sensors 110, which can be configured to measure tissue impedance, a change in tissue impedance across regions of tissue, and/or both low-frequency ($\alpha$ region) impedance and high-frequency ($\beta$ region) impedance. The impedance sensor(s) can be as described in relation to any of FIGS. 1-8. As shown in FIG. 13, the impedance sensor(s) can be positioned on the elongated member such that they can form an impedance sensor array 540. The elongated member can be as described in relation to FIGS. 9-11.

The impedance sensor(s) 110 can be electrically coupled to the elongated member 410. The electrical conductivity probe 500 can include additional sensors (e.g. pH, temperature, chemical, gas sensors) and additional circuitry as needed. In some embodiments, the electrical conductivity probe 500 can be configured to deliver an energy to result in focal ablation/cell membrane disruption in a tissue. Stated differently, the electrical conductivity probe 500 can also be a treatment probe in some embodiments. In other embodiments, the electrical conductivity probe 500 can be separate from a treatment probe. The electrical conductivity probe 500 and/or components thereof can be disposable, reusable, recyclable, biocompatible, sterile, and/or sterilizable.

The electrical conductivity probes 400,500 described herein can be manufactured by any suitable method and in any suitable way. Suitable methods include, but are not limited to, injection molding, 3-D printing, glass/plastic molding processes, optical fiber production process, casting, chemical deposition, electrospinning, machining, die casting, evaporative-pattern casting, resin casting, sand casting, shell molding, vacuum molding, thermoforming, laminating, dip molding, embossing, drawing, stamping, electroforming, laser cutting, welding, soldering, sintering, bonding, composite material winding, direct metal laser sintering, fused deposition molding, photolithography, spinning, metal evaporation, chemical etching and sterolithography. Other techniques will be appreciated by those of skill in the art.

Real-Time Lesion/Treated Area Monitoring Systems

Also provided herein are lesion and treated area monitoring systems that can include one or more electrical conductivity probes and components thereof described in relation to FIGS. 1-13 that can monitor lesion formation during focal ablation/cell membrane disruption therapy. Discussion of the various systems begins with FIG. 13, which shows embodiments of a real-time lesion monitoring system 600. An electrical conductivity probe 610 can be coupled to an impedance analyzer 620. The electrical conductivity probe 610 can be any electrical conductivity probe as described in relation to FIGS. 9-13. The impedance analyzer 620 can be electrically coupled to the impedance sensor(s) 110 of the electrical conductivity probe 610. In some embodiments, the impedance analyzer can contain one or more switches 630, where each switch can be coupled to a single impedance sensor on the electrical conductivity probe 610.

The impedance analyzer 620 can include or be coupled to one or more current injection electrodes 640 configured to inject a low voltage (0.1-1000 mV or more) signal into the impedance sensor(s) 110 of the electrical conductivity probe 610. The injection electrode(s) 640 can each be coupled to an impedance sensor 110 via a switch. Not all of the impedance sensors need be coupled to an injection electrode 640. Stated differently, in some embodiments, only some of the impedance sensors are coupled to an injection electrode via a switch. In some embodiments, the injection electrodes 641 a,b are separate from the impedance sensor(s) 110 and can be placed on the outside of an impedance sensor array 200. (see e.g. FIG. 13). The impedance analyzer and/or injection electrodes can be coupled to a low voltage power supply 650.

The impedance analyzer 620 can be coupled to and/or in communication with a computer or other data storage/processing device 660. The impedance analyzer 620 can be wirelessly coupled to the computer 660. The impedance analyzer can be hard wired to the computer 660. The computer 660 can contain processing logic configured to analyze data from the impedance analyzer 620 or other sensor information received from the electrical conductivity probe 610 and determine the size of the lesion or treated area 730 in the tissue 740. The computer 660 can contain processing logic configured to generate or initiate a signal (visual, audible, digital or otherwise) to alert a user that the lesion or treated are has reached a threshold size. The computer 660 can contain processing logic that can be configured to analyze data received from the impedance analyzer 620 and/or electrical conductivity probe 610 can contain processing logic configured to analyze data from the impedance analyzer 620 or other sensor information received from the electrical conductivity probe 610 and generate an electrical tomographic image of the treatment area. In some embodiments, the processing logic can be configured to determine the ratio of low-frequency impedance to high frequency impedance at a given impedance sensor 110 from impedance sensor data received from the impedance analyzer 620 and/or electrical conductivity probe 610. The computer 660 can contain processing logic configured to determine the amount of high voltage that should be applied to the treatment area via a treatment probe 670 in response to the impedance data and/or other sensory information received.

The computer 660 can be coupled to a waveform generator 680. The waveform generator 680 can be coupled to a gate driver 690. The gate driver 690 and/or impedance analyzer 620 can be coupled to a high voltage switch 700. The high voltage switch can be coupled to an energy storage device 710. The energy storage device can be coupled to a high voltage power supply 720, configured to deliver a high voltage that can range from 50 to 10000 V or more. A treatment probe 670 can be coupled to the high voltage switch 700. The high voltage switch 700 can be controlled by and/or responsive to the waveform generator 680 and/or gate driver 690. Insofar as the waveform generator 680 and/or gate driver 690 can be controlled by the computer 660, treatment can be, in some embodiments, autonomously controlled in response to impedance and other sensory data obtained by the electrical conductivity probe 610 during treatment. The operation of the system is discussed in further detail below.

Figure 15:
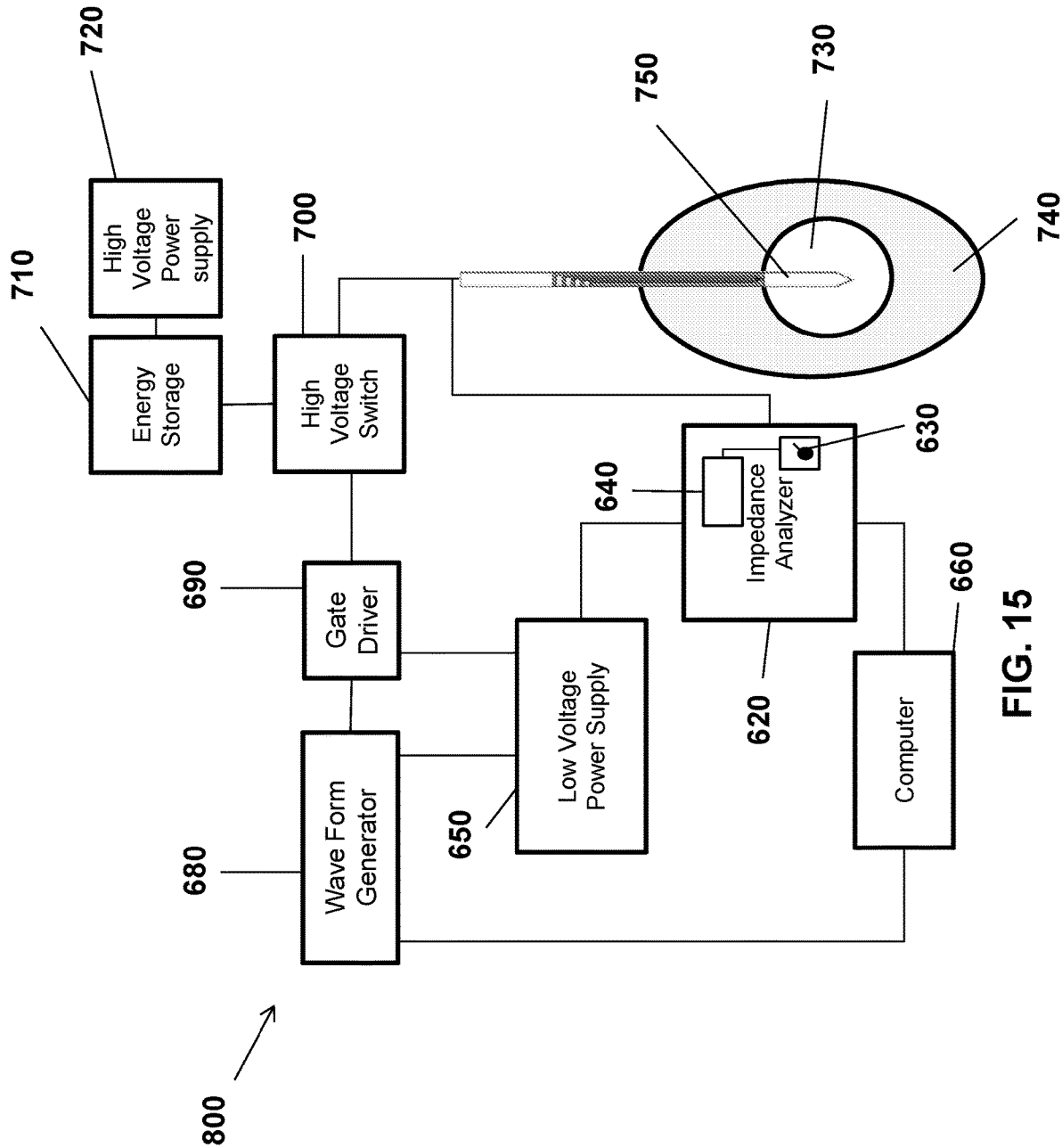
FIG. 15 shows embodiments of a system configured to monitor lesion/treated area formation in real-time.

In some embodiments, such as those shown in FIG. 15, the electrical conductivity sensor only includes one sensing area as opposed to an array of sensors which provides ease of fabrication and could be used to tell if the lesion front has reached a certain point rather than monitoring its location. The system 800 can be configured the same as that described in relation to FIG. 13, except that a single probe 750, which can contains one or more impedance sensor or an impedance sensor array, is coupled to both the high voltage switch 700 and the low voltage power supply 650.

Real-Time Lesion Front/Treated Area Monitoring

The devices and systems described herein can be used to monitor the lesion formation/front and/or treated area during focal ablation/cell membrane disruption therapies, which include, but are not limited to radiofrequency (RF) ablation, microwave ablation, laser ablation, cryo-ablation, ultrasound, electroporation (reversible and irreversible), supraporation, and radiation therapy. Thus, these devices and systems have application for tumor and undesired ablation, drug delivery, and gene therapy and nucleic acid and other molecule delivery. In principle, an electrical conductivity probe as described in relation to FIGS. 1-13 can be inserted into a tissue. During focal ablation or cell membrane disruption, the treated portion of the tissue undergoes changes due to changes in the permeability of the cell membrane. This results in the formation of a lesion or treated area (e.g. area of tissue to which a drug or other molecule has been delivered). As treatment continues the size of the lesion or treated area can grow. Impedance and other sensors on the electrical conductivity probe can measure electrical conductivity, pH, temperature, chemicals, and/or gasses at locations in the tissue. The systems and devices described herein can then determine the lesion size based upon the electrical conductivity data and other sensory information determined by the probe. In some embodiments, the system can be configured to autonomously control the treatment probe such that when the lesion has reach a desired size, the system can stop treatment in the tissue. In embodiments, the system can be configured to alert a user that the lesion/treated are has reached a desired size. In some embodiments, a user can alter treatment in response to the determined lesion/treated area size. The operation of the systems and devices is discussed in greater detail with respect to FIGS. 16A-17C.

Figure 16A:
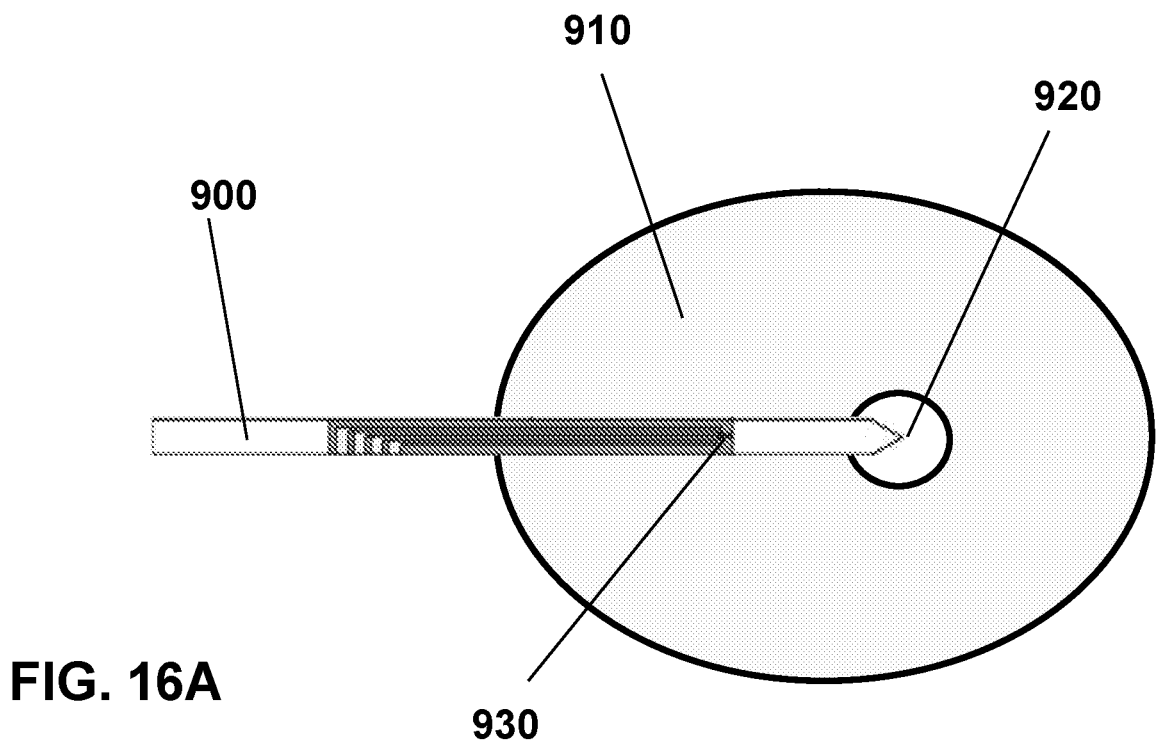
FIGS. 16A-16B show embodiments of operation of an electrical conductivity probe during treatment to monitor lesion/treated area formation in real-time.
Figure 16B:
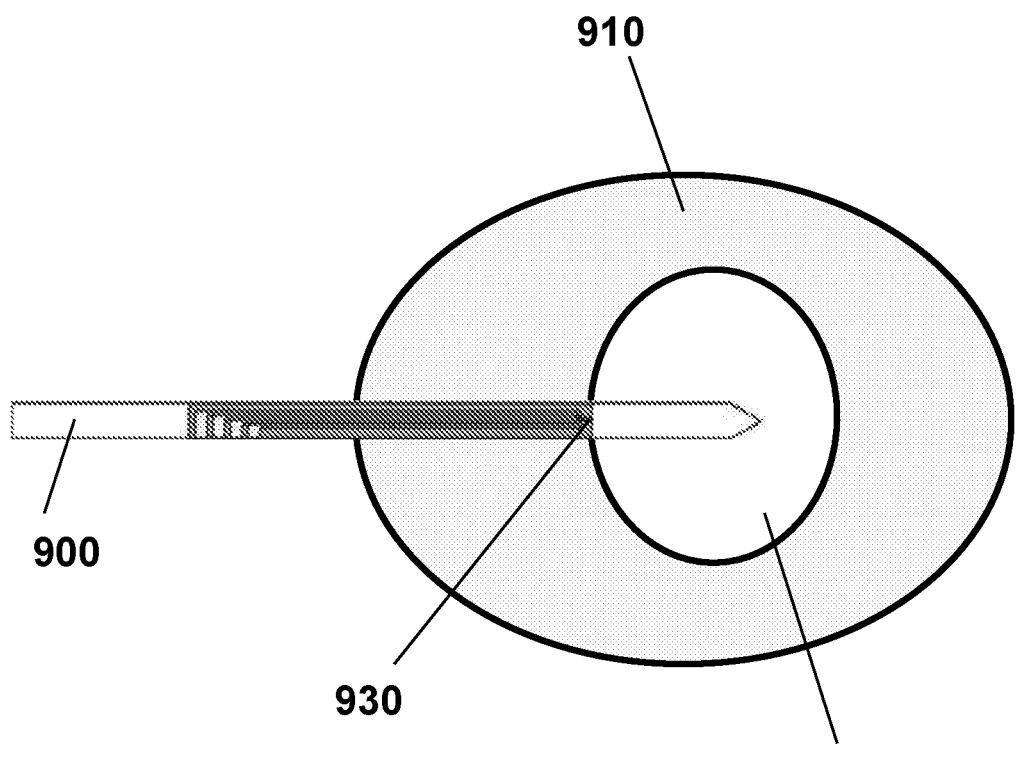

Discussion of the operation of the systems and devices begins with FIGS. 16A-16B, which show monitoring of a lesion/treated area formation and front using an electrical conductivity probe having an impedance sensor during treatment (FIG. 16A) and at the treatment endpoint (FIG. 16B). The treatment probe is not shown in FIGS. 16A and 16B for clarity. However, it will be appreciated that treatment may be provided by a separate treatment probe or be provided by the electrical conductivity probe, which can be configured to deliver high voltage treatment as well as measure tissue characteristics. FIGS. 16A-16B demonstrate monitoring of lesion/treated area formation and front during treatment when using a single impedance sensor (or other sensor) or multiple impedance sensors (or other sensors) placed radially about the surface of the probe such that the sensors are all at the same point along the length of the probe.

As shown in FIG. 16A, the electrical conductivity probe 900 can be inserted into the tissue 910. The electrical conductivity probe 900 can be inserted into the tissue such that the impedance or other sensor is at the outer edge of the desired treatment area. As treatment begins, a lesion or treated area 920 begins to form as the permeability of the cell membranes change. During this time impedance and/or other tissue characteristics are being measured by the sensor(s) 930 on the electrical conductivity probe. The sensors (impedance or other types) can be as described in relation to FIGS. 1-8. As such, during treatment, the impedance and/or other tissue characteristics can be continually determined during treatment and compared to prior measurements, including any baseline measurements taken prior to the start of treatment, to determine if the lesion/treated area has reached the desired size. As shown in FIG. 16B, when the lesion/treated area has grown such that it reaches the point in the tissue where the impedance or other sensor(s) 930 is located, the sensor(s) will measure a change in electrical conductivity and/or pH, chemical concentration, gas concentration, or other molecule concentration and the system can alert a user that the size of the lesion/treated area has reached the desired size. For example, in some embodiments, when the lesion/treated area reaches the sensor(s) 930 on the electrical conductivity probe 900, the low-frequency impedance is equal to the high-frequency impedance. In other embodiments, the system can automatically stop treatment via the treatment probe in response to a detected change in the impedance or other tissue characteristic.

While systems and devices employing sensor(s) at a single point along the length of the probe can be suitable for some applications, they can only determine the size of a lesion/treated area when it reaches a single point. With that in mind attention is directed to FIGS. 17A-17C, which show the operation of an electrical conductivity probe having a sensor array (e.g. an electrical impedance sensor array) during treatment. The treatment probe is not shown in FIGS. 17A-17B for clarity. However, it will be appreciated that treatment may be provided by a separate treatment probe or be provided by the electrical conductivity probe, which can be configured to deliver high voltage treatment as well as measure tissue characteristics.

Figure 17A:
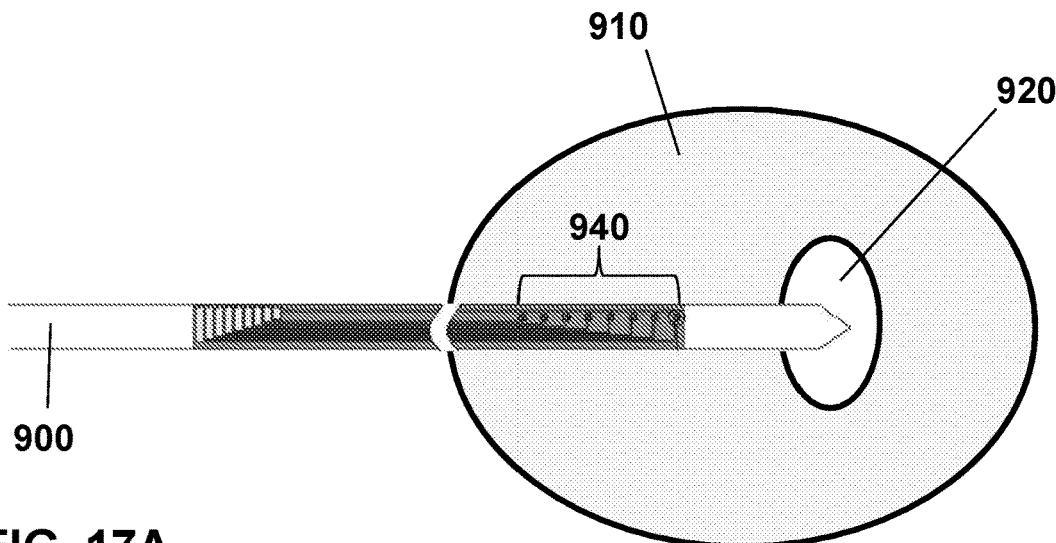
FIGS. 17A-17C show embodiments of operation of an electrical conductivity probe during treatment to monitor lesion/treated area formation in real-time.
Figure 17B:
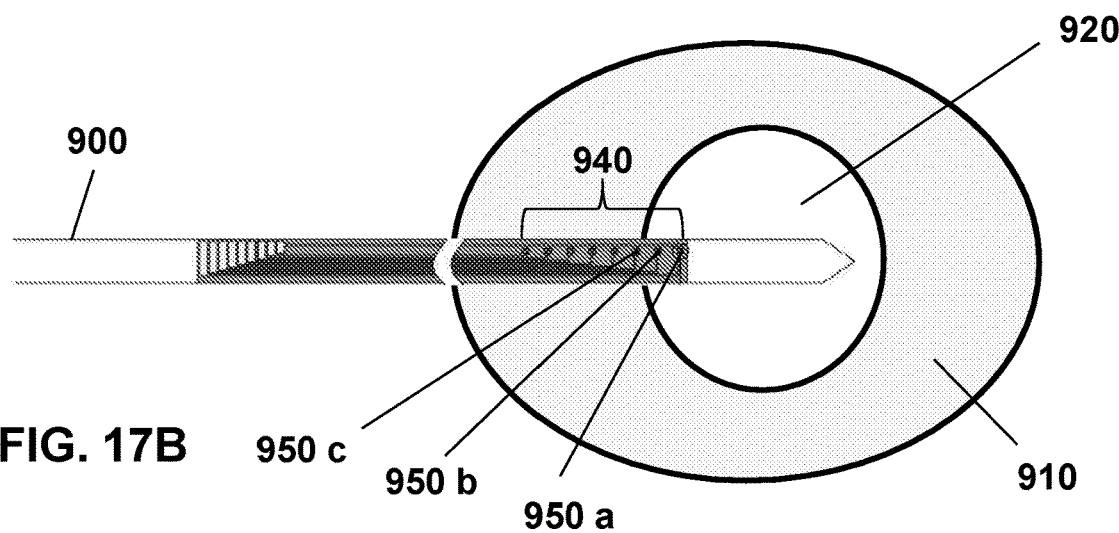
Figure 17C:
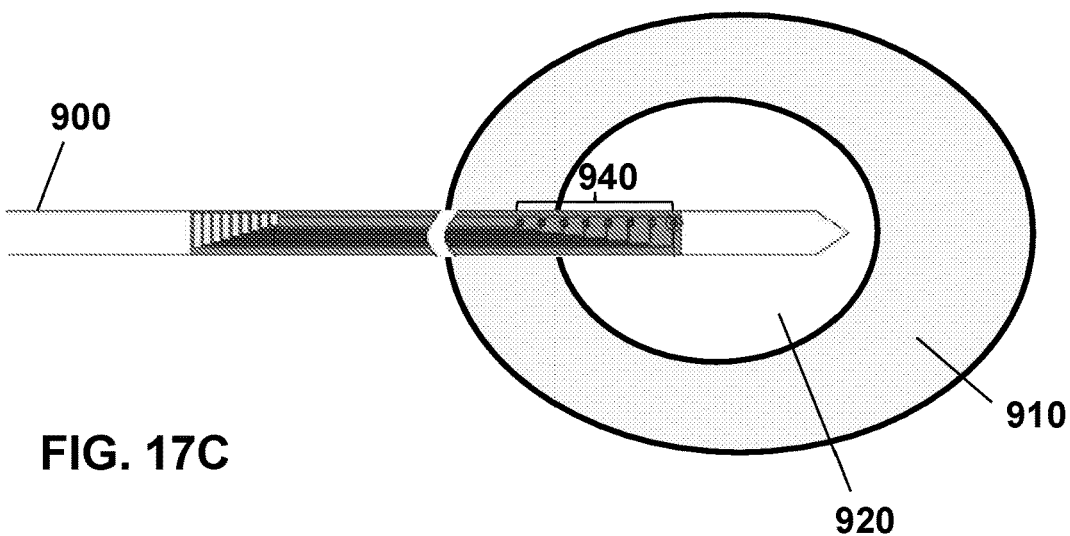

As shown in FIG. 17A, the electrical conductivity probe 900 can be inserted in a tissue 910 to be treated. Baseline impedance and other tissue characteristic measurements can be obtained prior to the start of treatment. As treatment begins a lesion/treated area 920 can form in the tissue 910. During treatment the sensors of the sensor array 940 can be measuring impedance and/or other tissue characteristics (e.g. pH, chemical concentration, gas concentration, temperature, other molecule concentration, and the system (not shown for clarity) can be determining if there is a change in the impedance and/or other tissue characteristics at any given sensor along the sensor array 940 or between any combination of sensors along the sensor array 940. As the lesion front/treatment area 920 grows (see FIG. 17B), the system will determine that there is a change relative to base line and/or that of another sensor in the impedance and/or other tissue characteristic between certain sensors within the array. From that data the system can determine the size of the lesion and/or determine the position of the lesion front as the lesion grows during treatment. For example, as shown in FIG. 17B the lesion/treated area 920 has grown such that the lesion front is between the second 950b and third sensor 950c of the sensor array 940. As such, the system can determine that there is a change in the impedance (or other tissue characteristic) at the second sensor 950b relative to baseline. The system can determine that there is no change in the impedance (or other tissue characteristic) at the third sensor 950c relative to baseline. From this, the system can determine that the lesion front/treated area has reached the position on the probe that lies between the second 950b and third 950c sensor on the electrical conductivity probe 900. The process of continually measuring impedance (other tissue characteristic) by the sensors of the sensor array 940 and comparing them to baseline/and or other data from other sensors of the sensor array 940 can continue until the lesion/treated area 920 has reached a desired size. The desired size can be predetermined and the system can be configured to alert a user via a signal when the system calculates that the desired size has been reached. In other embodiments, the system can be configured to automatically stop treatment when the system calculates that the desired size has been reached.

It will be appreciated that any number of electrical conductivity probes 900 can be used at the same time. By placing electrical conductivity probes 900 at different locations and depths into the tissue, the data provided can be used by the system to determine a volume of the lesion/treated area and/or generate a three dimensional image of the treated area.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Figure 18:
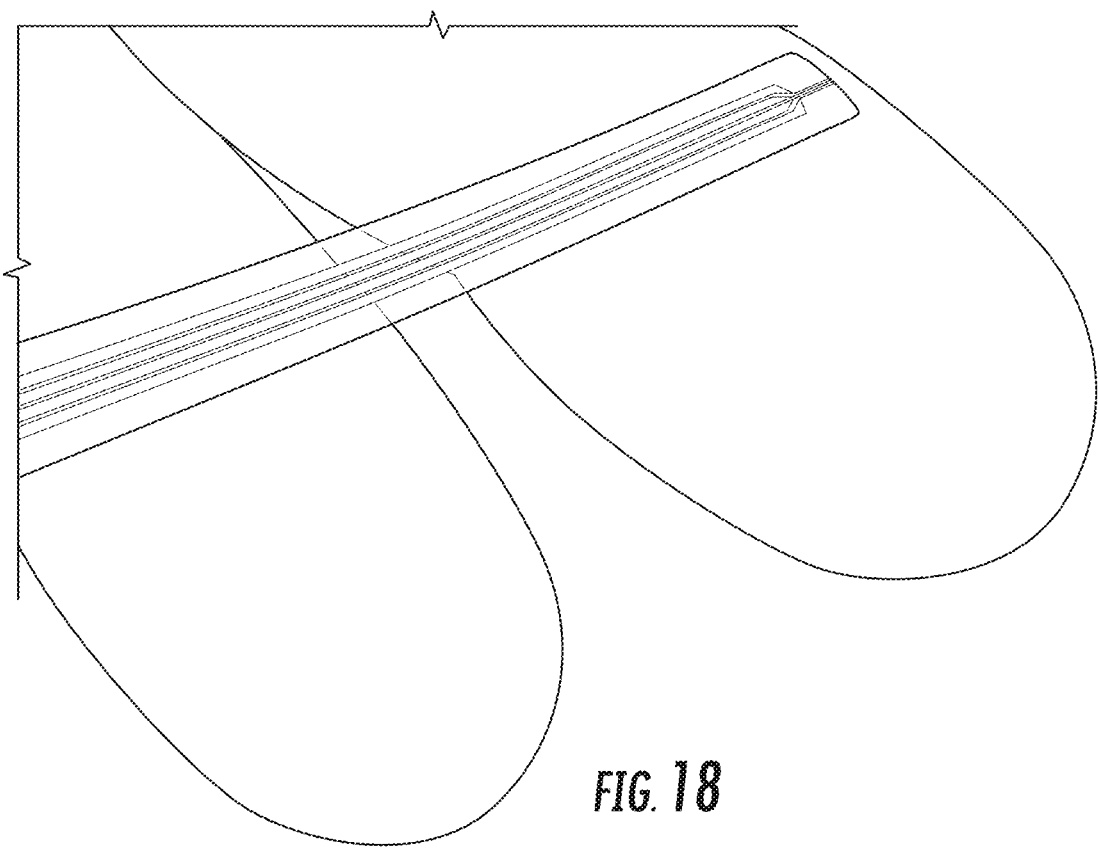
FIG. 18 shows an image of an embodiment of an electrical conductivity sensor.
Figure 19:
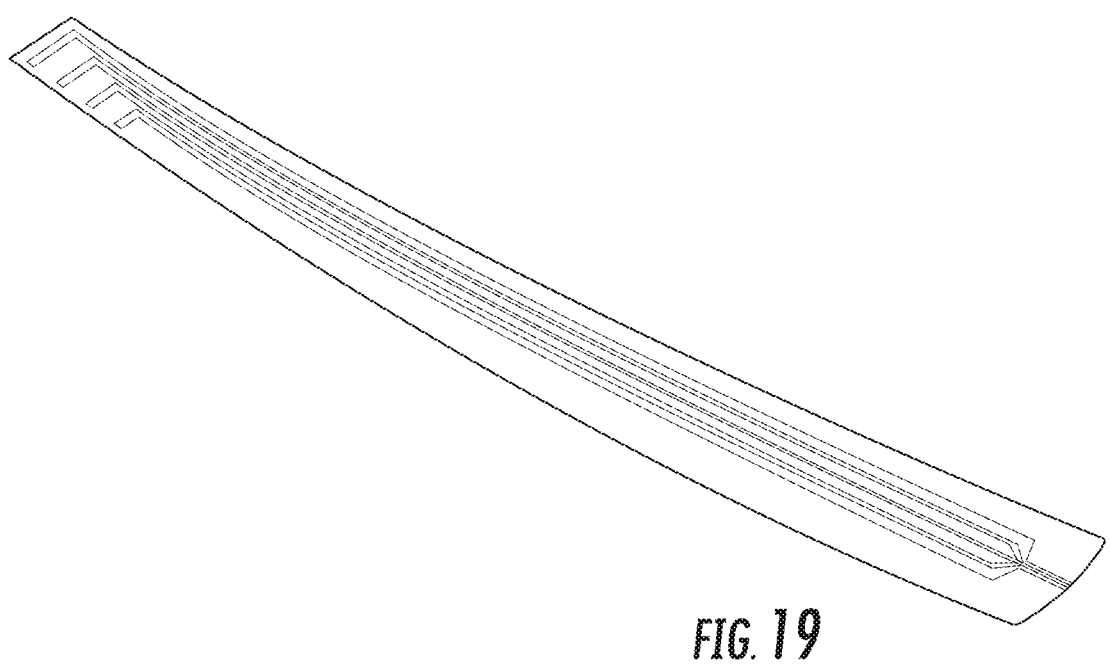
FIG. 19 shows an image of an embodiment of an electrical conductivity sensor.
Figure 20:
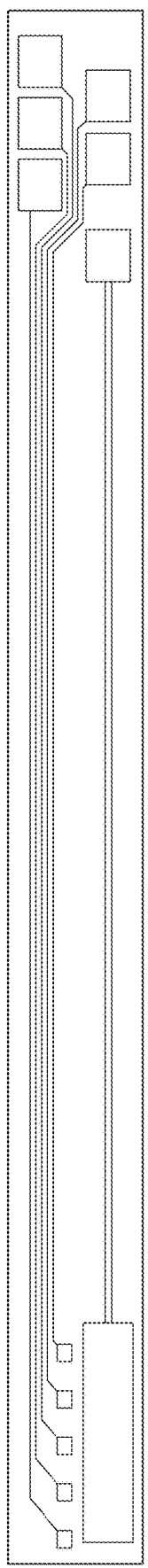
FIG. 20 shows an image of an embodiment of an electrical conductivity sensor.
Figure 21:
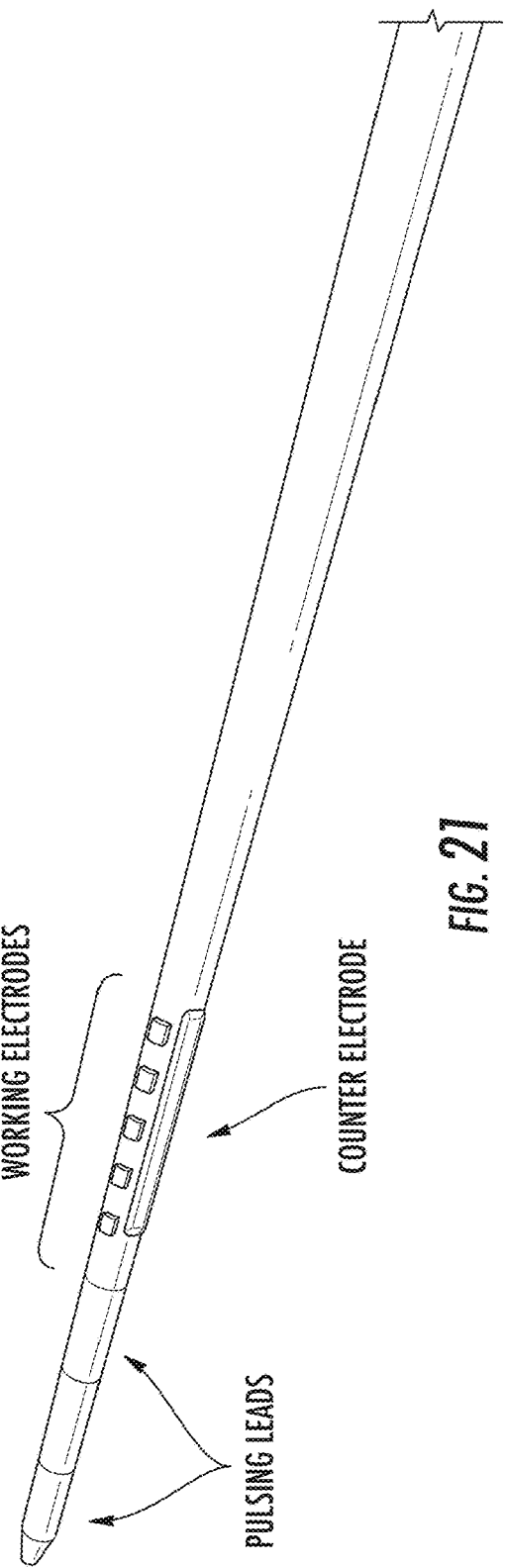
FIG. 21 shows an image of an embodiment of an electrical conductivity probe.

FIGS. 18-20 show images demonstrating an electrical conductivity sensor as described in relation to any of FIGS. 1-8. The fabricated probe is about 15 micron thick, 8 cm long and 8 mm wide. The gold wires are sandwiched between two polyimide layers. The polyimide layer over the bonding pads and the sensor area is removed to expose these parts. The small dimensions of the sensor can enable conductivity measurement with a high spatial resolution. The electrical conductivity sensor can be wrapped around a probe, such as an irreversible electroporation probe (IRE) or other treatment probe to create a device capable of both treating tissue with electroporation and monitoring the extent of the treatment in real-time. In this probe, the conductivity measurement can be conducted at one point next to the beginning of the exposed area of the IRE probe. The electrode can be flexible enough to be easily wrapped around IRE probes with a small diameter of 1 mm. FIG. 21 shows an image of an electrical conductivity sensor that has been coupled to an IRE probe.

Example 2

FIGS. 22A-22J demonstrate a fabrication process for the construction of the electrical conductivity sensor of Example 1. A 4" Si wafer 2200 was used as the fabrication substrate. The wafer edge was treated with a solution of adhesion promoter (HD Microsystems, Parlin, N.J.) to provide adhesion between the wafer 2200 and the polyimide layer 2210 (FIG. 22B). The adhesion should be enough to keep the construct on the wafer 2200 during the fabrication steps. (FIG. 22B) Polyimide (HD Microsystems, Parlin, N.J.) substrate 2210 was spun and cured over the Si wafer 2200. The spin speed was adjusted to achieve a thickness of about 15 microns. The spin step could be repeated if a greater film thickness is desired. (FIG. 22C) A layer of about 300 nm of gold was deposited on the polyimide layer by PVD. For a better adhesion of gold to the polyimide substrate a Cr layer 2200 was deposited first. (FIG. 22C) A photoresist layer 2230 was spun and patterned as the desired gold electrodes using the photolithography techniques. FIG. 22D The patterned photoresist was used as a mask for wet etching of gold in the next step. Gold and Cr layers were etched 2240 (FIG. 22E) using appropriate wet etching solutions and the photoresist layer 2230 was washed away. Another layer of polyimide 2250 was spun and cured to act as an insulator over the electrode FIG. 22F. The insulator should cover the wires of the electrode and leave the sensor and bond pads exposed. A Ti mask 2260 was deposited by PVD and patterned by photolithography techniques followed by wet etching (FIG. 22G). The Ti mask was used to etch the upper polyimide layer in RIE (Reactive Ion Etching) to expose 2270 the sensing areas and bond pads (FIG. 22H). The Ti mask was washed away using wet etching (FIG. 22I). The whole electrode structure was peeled off the Si wafer 2200 (FIG. 22J). To protect the impedance electrodes from high voltage electric discharge of the pulsing leads, a thin passivation layer such as silicon dioxide or silicon nitride can be coated on the sensor area. This passivation layer acts as a capacitor which protects the sensor from high voltage of the DC pulses however has a minimal impact on the AC impedance readings. Functionalization of the sensors with receptor molecules configured to specifically bind a target molecule can performed after metal patterning as an option using techniques known in the art.

Example 3

Figures 23A, 23B:
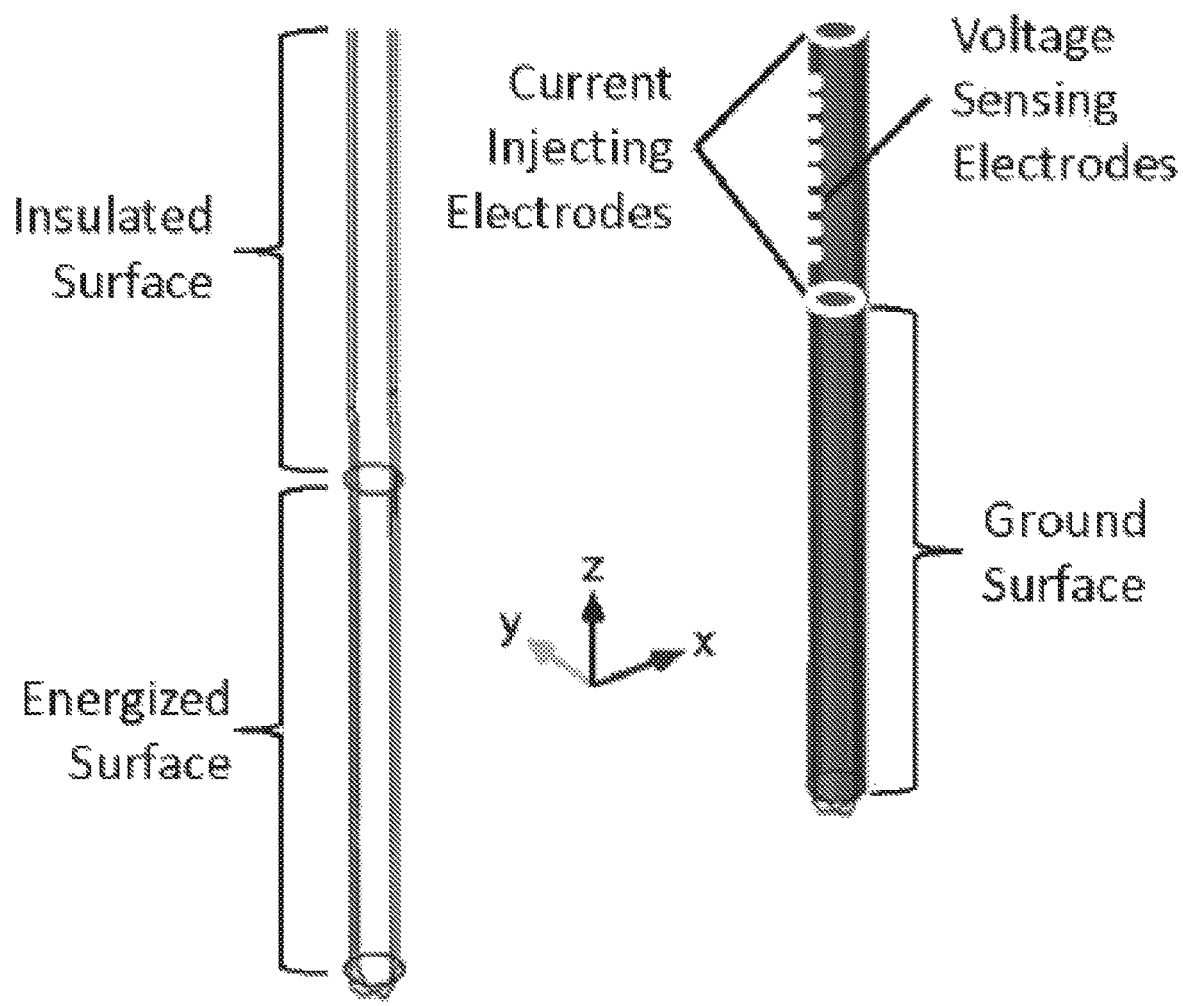
FIGS. 23A-23B show a three dimensional finite element model to simulate IRE treatment of liver tissue with two needle electrodes.

A three dimensional finite element model was constructed in Comsol 4.2a (Burlington, Mass.) to simulate IRE treatment of liver tissue with two needle electrodes (FIGS. 23A-23B). The electric potential distribution within the tissue was obtained by transiently solving:

$$0 = -\nabla \cdot (\sigma(|E|)\nabla\phi) \quad \text{(Equation 1)}$$

Where $\phi$ is the electric potential, E is the electric field, and $\sigma$ is the electric conductivity. Equation 1 is obtained from Maxwell's equations assuming no external current density ($J=\sigma E$), no remnant displacement ($D=\varepsilon_0\varepsilon_r E$), and the quasi-static approximation. This approximation implies a negligible coupling between the electric and magnetic fields ($\nabla \times E=0$), which allows for the expression of electric field only in terms of electric potential:

$$E=-\nabla\phi \quad \text{(Equation 2)}$$

As depicted in Equation 1, the electric conductivity is a function of the electric field magnitude. This equation is used to describe the nonlinear of effects of pore formation in the cell membrane at the tissue scale. Specifically, this can be described by a step function with a certain degree of smoothing, or by other functions that follow similar relationships between the electric conductivity and electric field, such as sigmoid or Gompertz functions. The step function chosen here increased from a baseline conductivity of 0.3 S/m to a plateau of 1.05 S/m across a transition zone of 500 V/cm centered at 500 V/cm. Therefore, regions of tissue subject to an electric field above 750 V/cm were maximally electroporated.

An electric potential boundary condition of 1500 V was applied along the energized surface of one of the electrodes, with the corresponding ground portion of the alternate electrode set to 0 V. The dielectric properties of the exposed portion of the electrodes for performing IRE and the insulative portion for protecting healthy tissue can be found in Garcia, P. A., et al., *Intracranial Nonthermal Irreversible Electroporation: In Vivo Analysis*. Journal of Membrane Biology, 2010. 236(1): 127-136. All remaining interior boundaries were treated as continuity, and all remaining outer boundary conditions were treated as electrical insulation. The stationary problem consisting of 100,497 mesh elements was solved using an iterative, conjugate gradient solver.

Figure 24A:
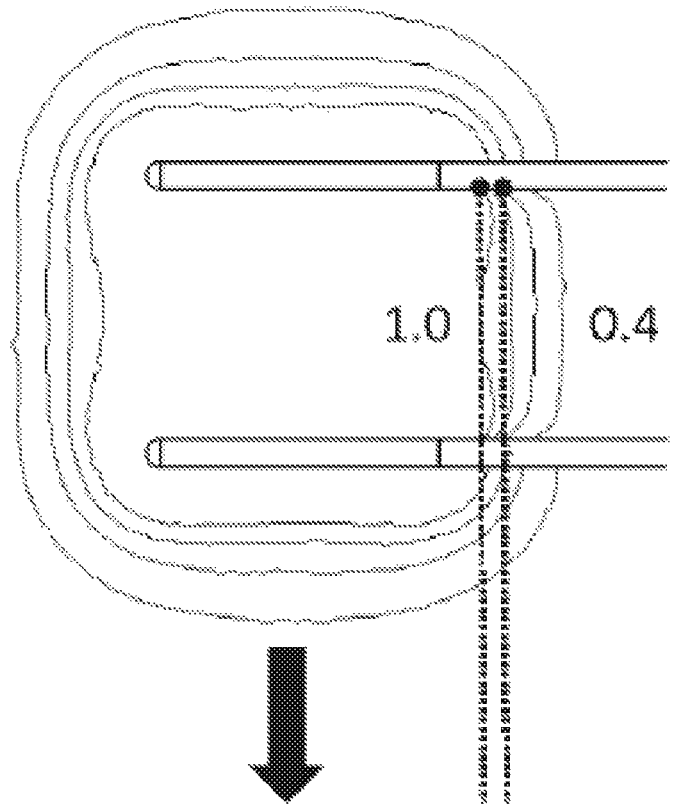
FIGS. 24A-24B show the simulated electrical conductivity in the tissue resulted from IRE (FIG. 24A) and simulated extrapolation of point specific measurements in three dimensions to determine the spatial-temporal conductivity map and electric field distribution (FIG. 24B).
Figure 24B:
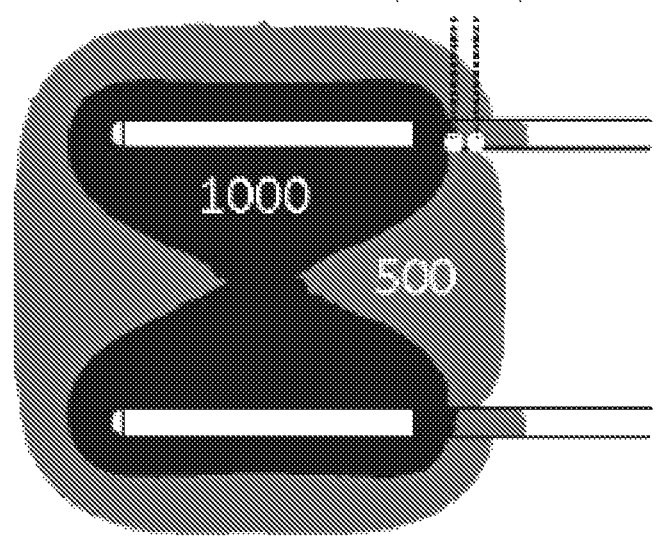

The electrical conductivity in the tissue resulting from IRE is shown in FIG. 24A. Experimentally, voltage drop measurements made between any combination of sensing electrodes can be used to determine this conductivity. Through comparisons to electrical measurements made prior to treatment, it is then possible to determine the extent to which tissue adjacent to each of the sensors has undergone electroporation. If impedance measurements are obtained between electroporative pulses of a multiple pulse protocol, then a real-time, dynamic representation of how the treated tissue expands along the length of the electrode can be obtained. Point specific measurements can also be extrapolated in three dimensions to determine the spatial-temporal conductivity map and electric field distribution (FIG. 24B).

Example 4

Figure 25A:
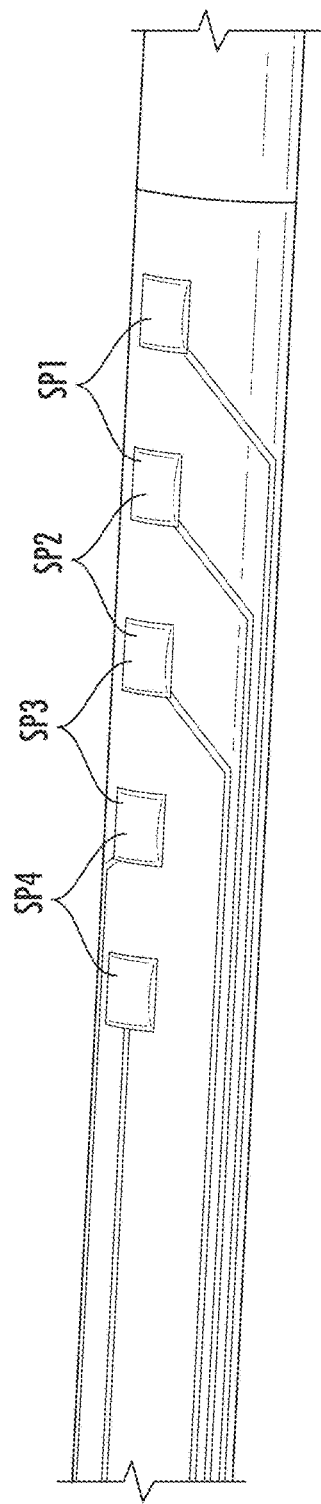
FIGS. 25A and 25B show images of a probe FIG. 25A and placement within a sample of porcine liver. The dashed circle in FIG. 2B indicates the treated area. The black dots indicate location of the sensors of the probe within the tissue.
Figure 25B:
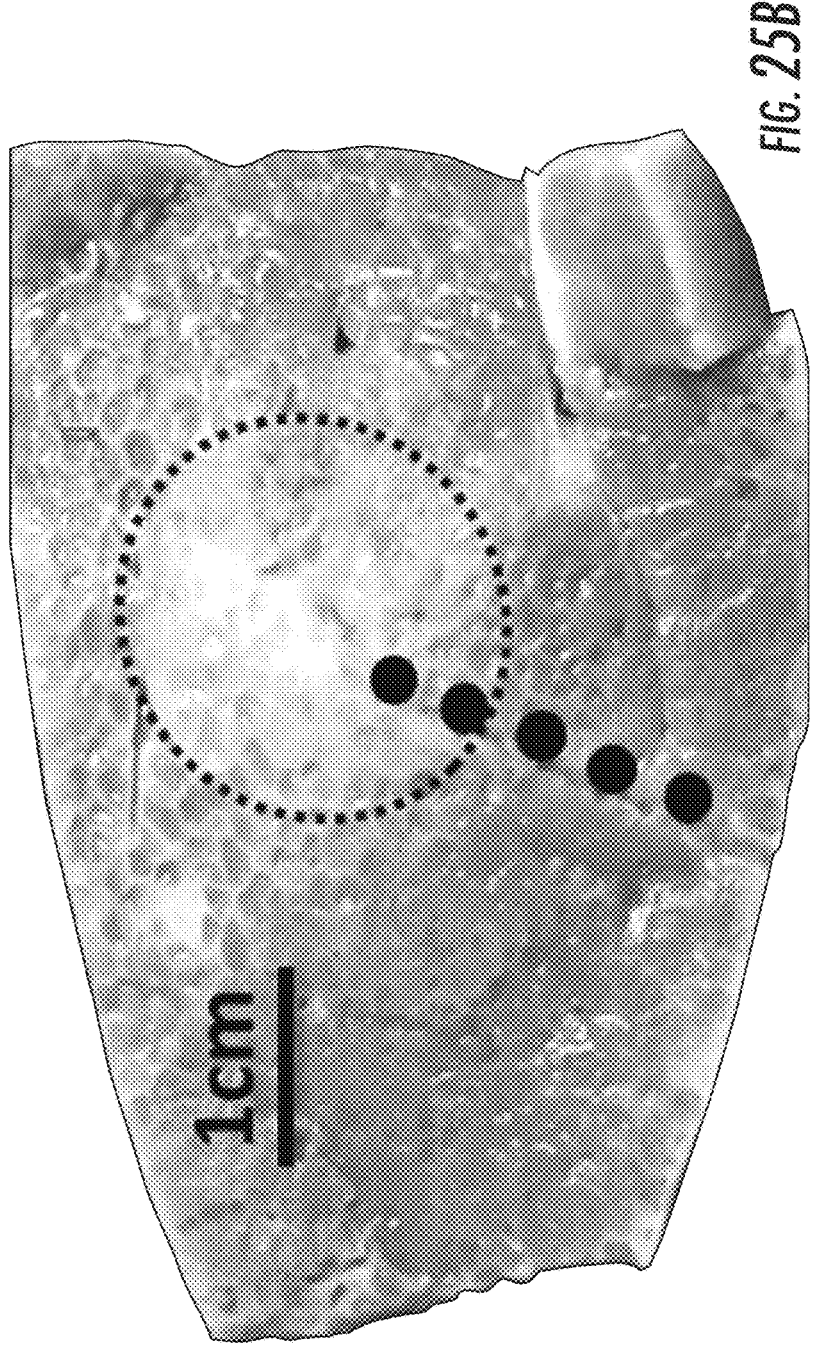

FIGS. 25A-27 describe results of delivering a series of high-frequency irreversible electroporation (HFIRE) pulses to porcine liver through the high voltage portion of a probe that also contains an impedance sensor array. FIG. 25A shows an experimental probe model with 5 microelectrodes and 4 sensing pairs (SP). In FIG. 25B, TTC Stained HFIRE ablation in liver (2000 V) can be observed in which viable tissue was stained red while dead tissue whitened. Ablation (marked by dotted line) reached only SP1. The impedance signature throughout delivery of HFIRE pulses as measured by SP1 is shown in FIG. 26). The largest change in impedance was observed at 5 khz, which indicated current was no longer confined to extracellular pathways and its flowing through the cell membrane—indicating electroporation of tissue. This progressive decline in resistance can be used to monitor ablation growth throughout the therapy. FIG. 27 presents the resulting changes in tissue impedance during HFIRE therapy at 5 khz. Major changes in impedance were only observed on probe pair in contact with treated tissue (FIG. 25B). FEM results for electric field distribution along the length of the probe for different pulse parameters can be correlated to these spatio-temporal changes in electrical conductivity during IRE procedures to indicate the electric field threshold for cell death in a tissue of interest.

Example 5

A real-time visualization tool for monitoring of reversible and irreversible electroporation treatments. Once the threshold for cell death in terms of bulk tissue conductivity has been characterized this information can be used to reconstruct the ablation in 3D. The volume of the ablation geometry can be described in 2D with a Cassini oval plot that has the results from one axis extrapolated into a third dimension.

The Cassini oval is a curve that derives its values based on the distance of any given point, a, from the fixed location of two foci, $q_1$ and $q_2$, located at $(x_1, y_1)$ and $(x_2, y_2)$. The equation is similar to that of an ellipse, except that it is based on the product of distances from the foci, rather than the sum. This makes the equation for such an oval:

$$\lfloor (x_2-a)^2+(y_2-a)^2 \rfloor=b^4 \quad \text{(Equation 3)}$$

where $b^4$ is a scaling factor to determine the value at any given point. For incorporation of this equation into shapes that represent the electric field distribution, it is assumed that the two foci are located at the center of the pulsing electrodes along the length of the probe (e.g., x-axis) at ($\pm$x,0).

Here, the parameter a represents the location of the ablation front along the length of an IRE needle. This is used to solve for b giving a complete equation to describe the ablation volume. After the probe is placed, software can record baseline values for impedance along a micro-sensor array. After treatment begins, impedance measurements can be recorded in real-time. The location of the ablation (lesion) front can be determined according to the characteristic conductivity of the tissue of interested after it has been irreversibly electroporated. Finally, this data can be used to calculate the ablation geometry, which can be projected as a 3D isometric view of SMART probe onto ortho-planes from stacked CT images of patient anatomy (FIG. 28A). Similarly, the ablation progression can be observed during treatment at 10 (green), 50 (red), and 100 (blue) pulses in axial (FIG. 28B), sagittal (FIG. 28C), and coronal planes (FIG. 28D). Ultimately this system can provide healthcare professions and other practitioners with real-time feedback of any IRE therapy, by displaying the ablation volume relative to a targeted tumor in medical scans such as MRI, PET, or CT.

Example 6

Figure 29A:
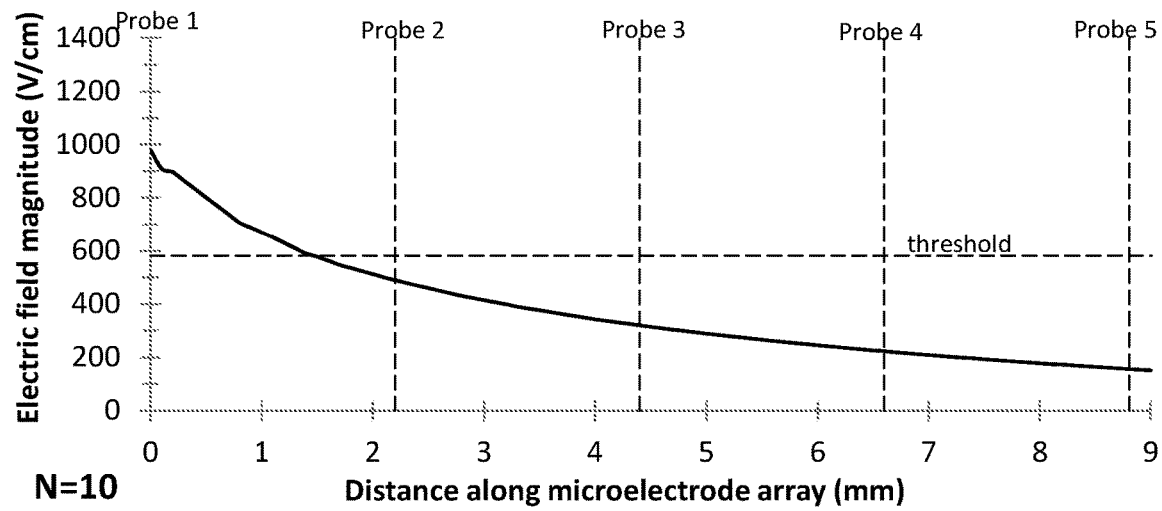
FIGS. 29A-29C show graphs demonstrating finite element modeling (FEM) of electric field magnitude along the length of the probe in a potato model, where N=10 (FIG. 29A), N=30 (FIG. 29B), and N=100 (FIG. 29C).
Figure 29B:
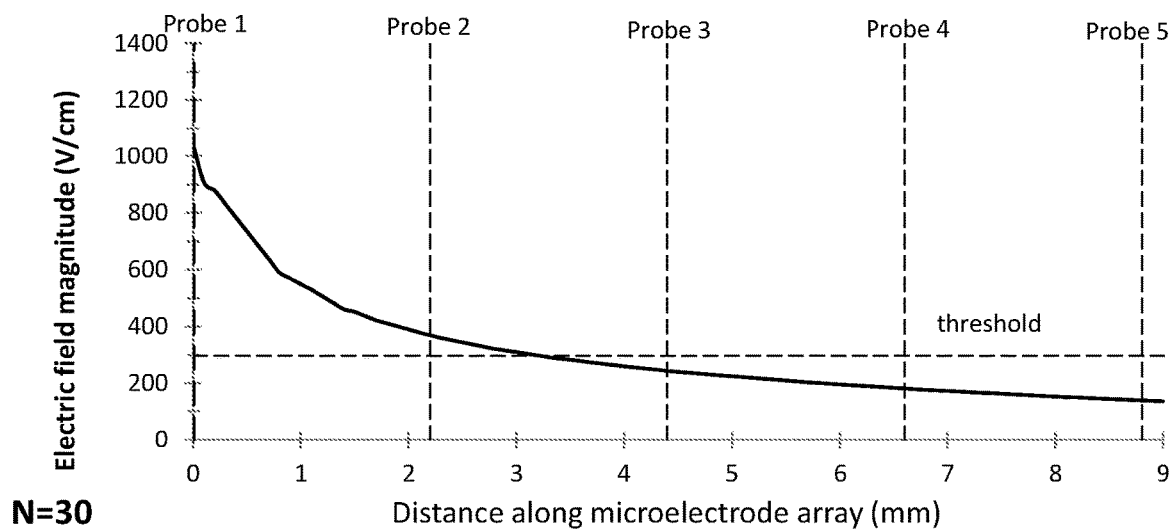
Figure 29C:
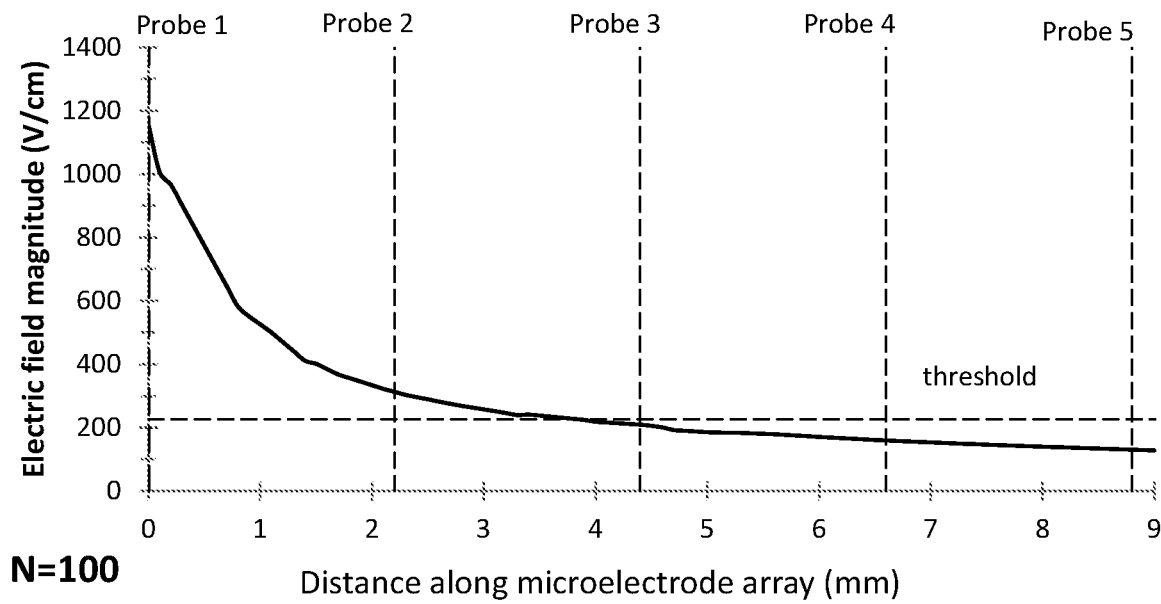
Figure 30A:
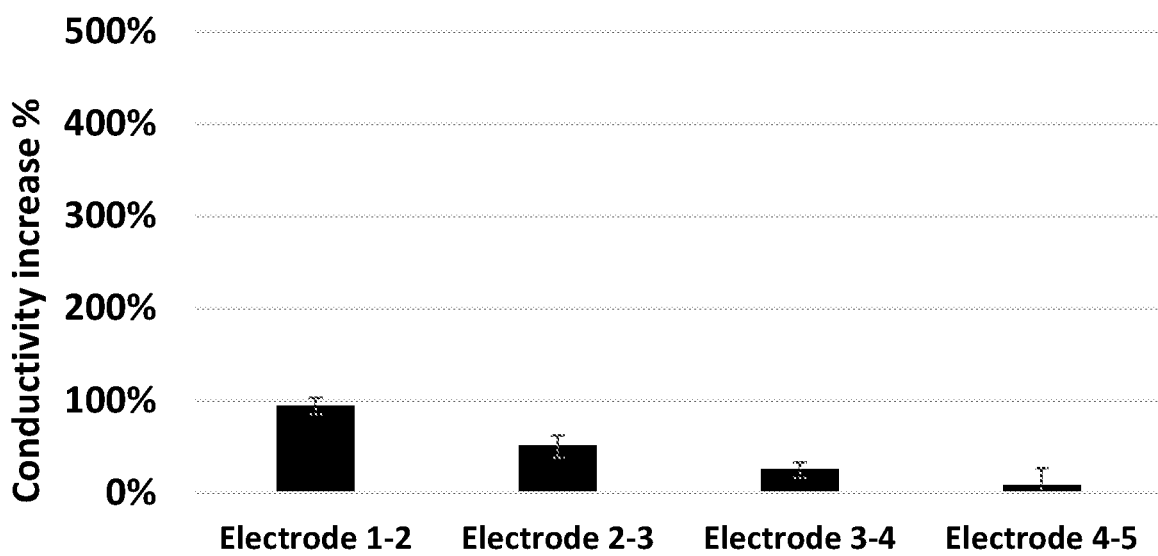
FIGS. 30A-30C show graphs demonstrating experimental results of conductivity change as measured by different sensor pairs along the length of the probe in a potato model, where N=10 (FIG. 30A), N=30 (FIG. 30B), and N=100 (FIG. 30C).
Figure 30B:
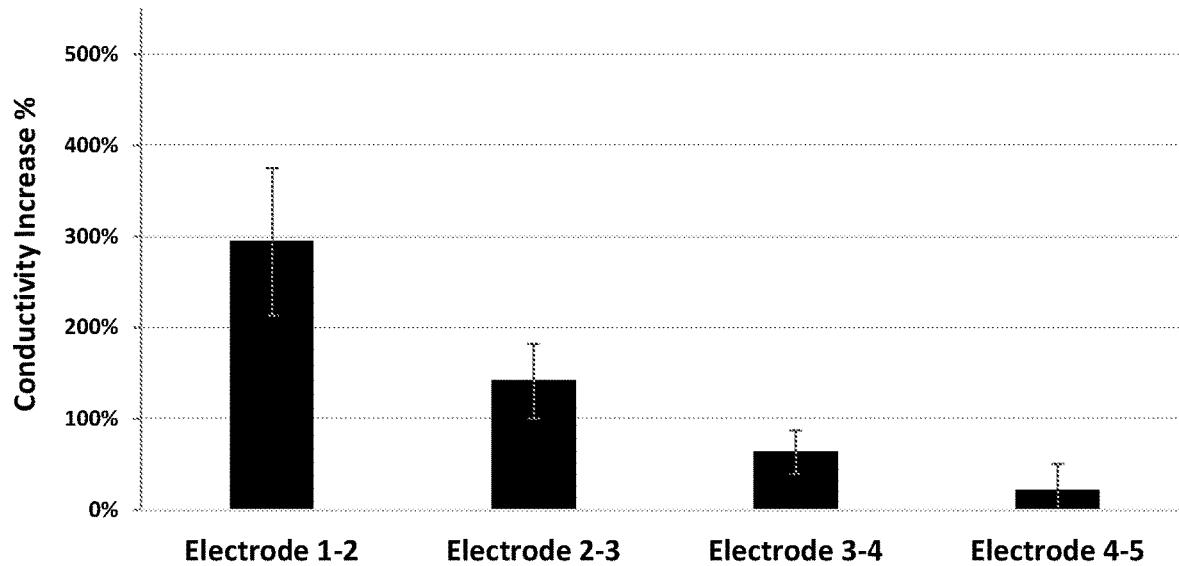
Figure 30C:
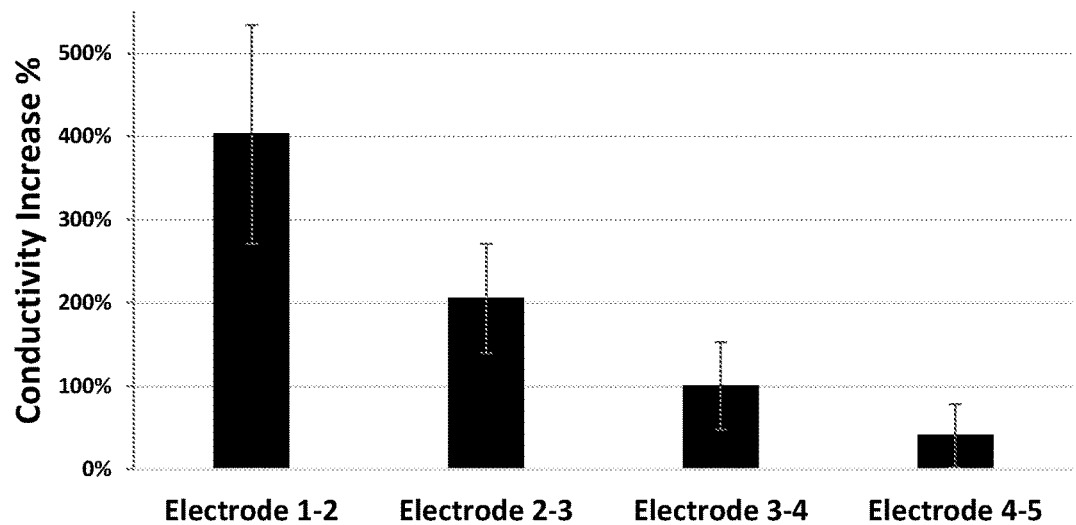
Figure 31A:
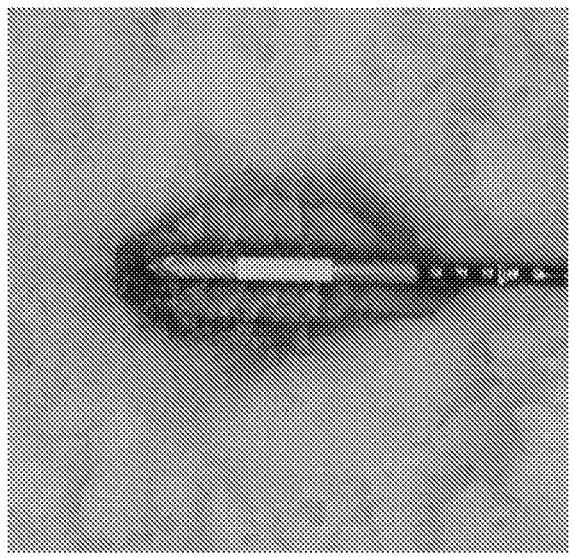
FIGS. 31A-31C show photos demonstrating experimental ablations after delivering a series of IRE pulses to a potato model where N=10 (FIG. 31A), N=30 (FIG. 31B), and N=100 (FIG. 31C).
Figure 31B:
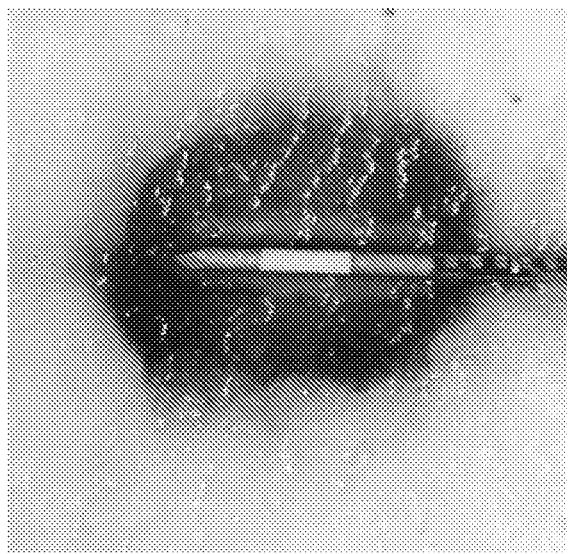
Figure 31C:
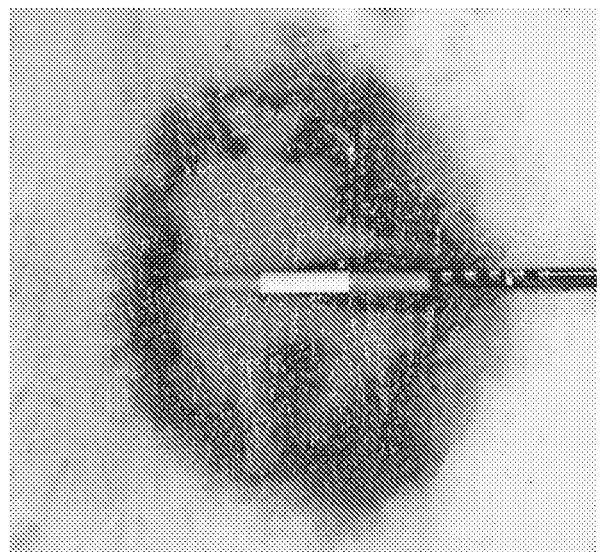

FIGS. 29A-31C describe parts of the methodology related to determining the location of the ablation front and the resulting geometry of the volume of ablation from a series of irreversible electroporation (IRE) pulses through the high voltage portion of a bipolar probe, also containing an impedance sensor array. FIGS. 29A-29C shows the finite element model (FEM) results for electric field distribution along the length of the probe for IRE pulses with a magnitude of 1500V. The dotted line corresponds to a characterized threshold for cell death dependent of a specific number of pulses (N) (e.g., 10, 30, 100). After the tissue has been treated with several IRE pulses an ablation front can be detected in the form of a change in tissue resistivity at different points along the probe (FIGS. 30A-30C). FIGS. 31A-31C shows the resulting volumes of ablation post IRE treatments 10, 30 and 100 pulses of 1500V.

Lesion growth in the perpendicular direction of the probe is also reflected in the impedance measurement by the probe. For example, it is predicted by FEM model (FIGS. 29A-29C, solid line) and observed in FIGS. 31A-31C that for 30 and 100 pulse treatments, probes 1 and 2 would fall within the lesion. However, the corresponding impedance measurement shows 400% and 500% increase in conductivity for 30 and 100 pulses, respectively. This difference is attributed to the depth of lesion in the perpendicular direction. For the case of 10 pulses of 1500V, the small depth of the lesion in perpendicular direction and the marginal location of probe 2 compared with the lesion, results in 200% relative conductivity for sensors 1-2 measurement. For all treatments, the measurements showing 100% relative conductivity correspond to electrodes completely outside of the lesion.

These experimental results show that device (electroporation leads and micro-electrode array) used during these experiments is not only capable of monitoring the lesion length along the probe, but also gives relevant information regarding its other dimensions. This information when combined with FEM modeling can give accurate shape and size of the lesion.

Example 7

Figure 32:
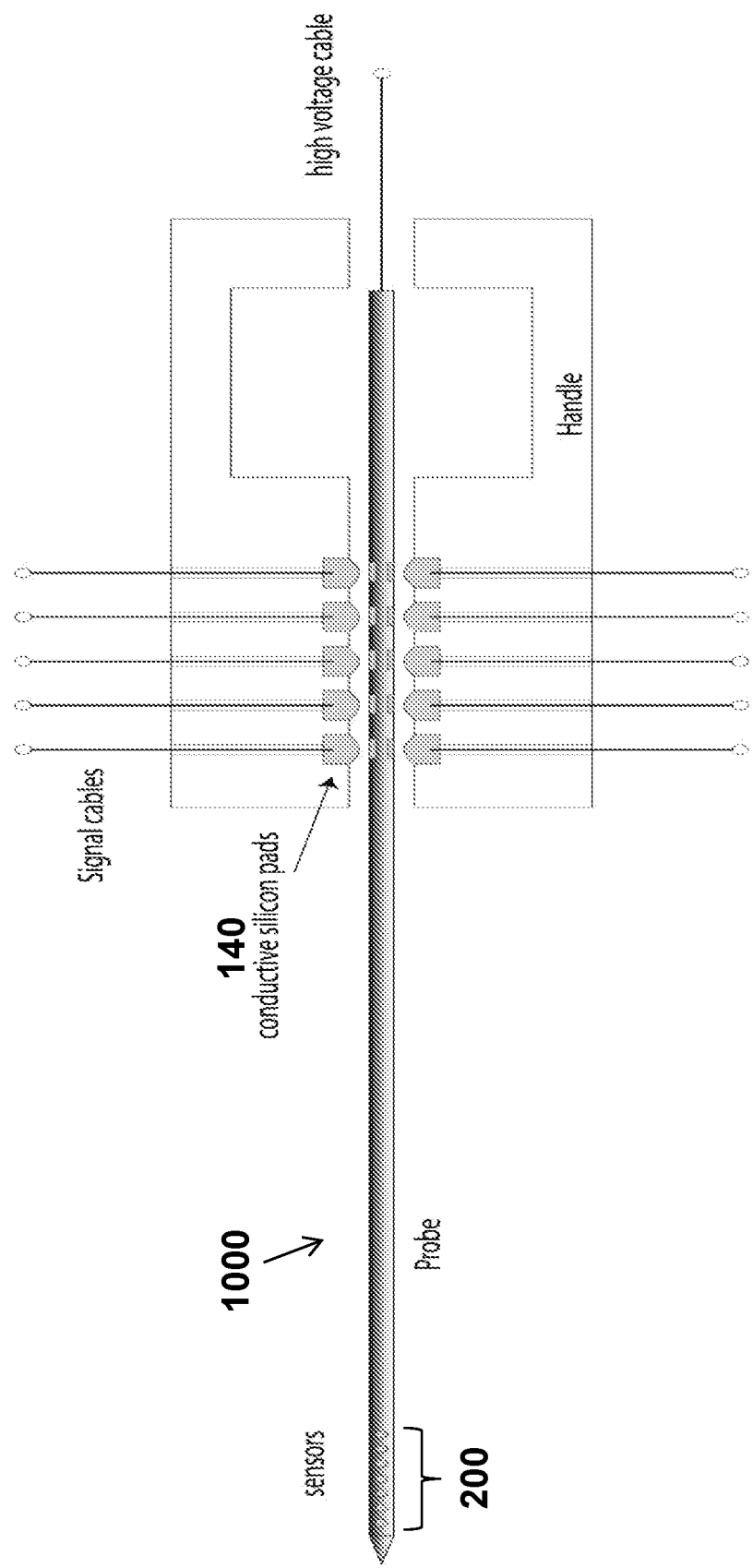
FIG. 32 shows embodiments of installation of a sensor array on a probe and the electrical connections to the sensor.

FIG. 32 shows a diagram demonstrating how the electrical connections to a conductivity probe 1000 can be made through conductive flexible silicon pads or any other flexible conductive material or structure that can be installed in the handle and in opposite side of the conductive pads 140. The conductive silicon pads can be connected to the external wires. Upon assembly, the conductive silicon pads come in conformal contact with the gold pads on the conductivity sensor and make the electrical connection.

Example 8

Figure 33A:
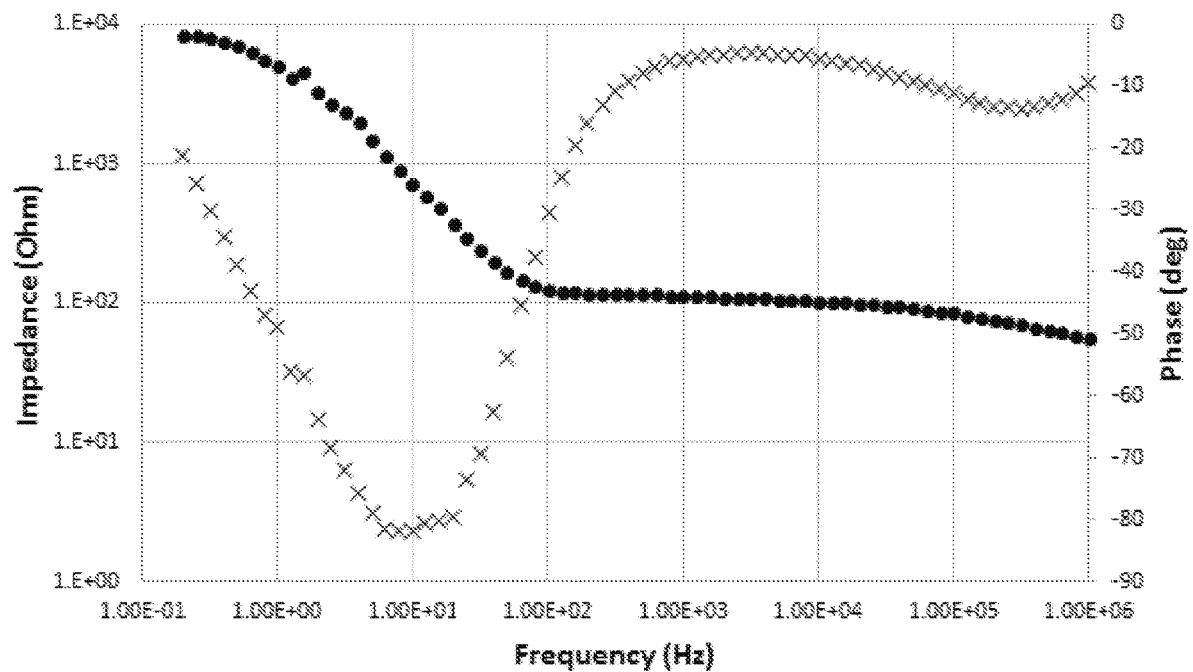
FIGS. 33A-33B shows the electrical impedance spectrum of the porcine liver (FIG. 33A) along with the equivalent circuit model of the tissue (FIG. 33B).
Figure 33B:
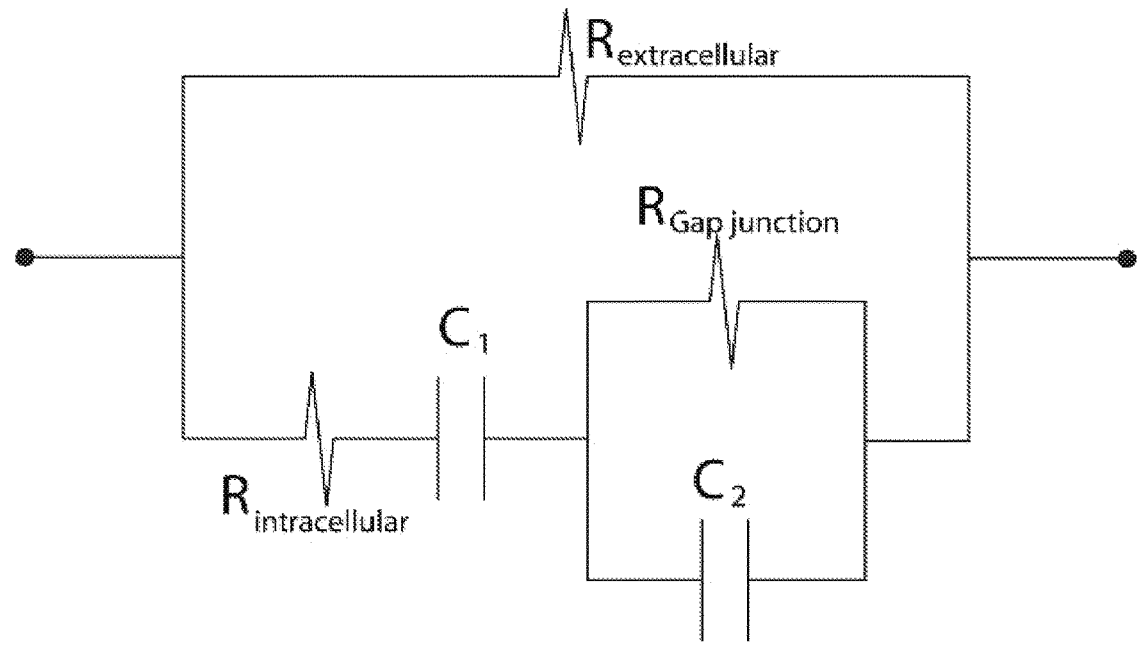

FIG. 33A shows a graph demonstrating the impedance spectrum of porcine liver as measured by the conductivity sensor. Fitting of the spectrum to the equivalent circuit model of tissue reveals critical tissue properties at cellular level which could be used for determination of lesion size during ablation. FIG. 33B shows one example of tissue electric circuit model.

Example 9

Figure 34:
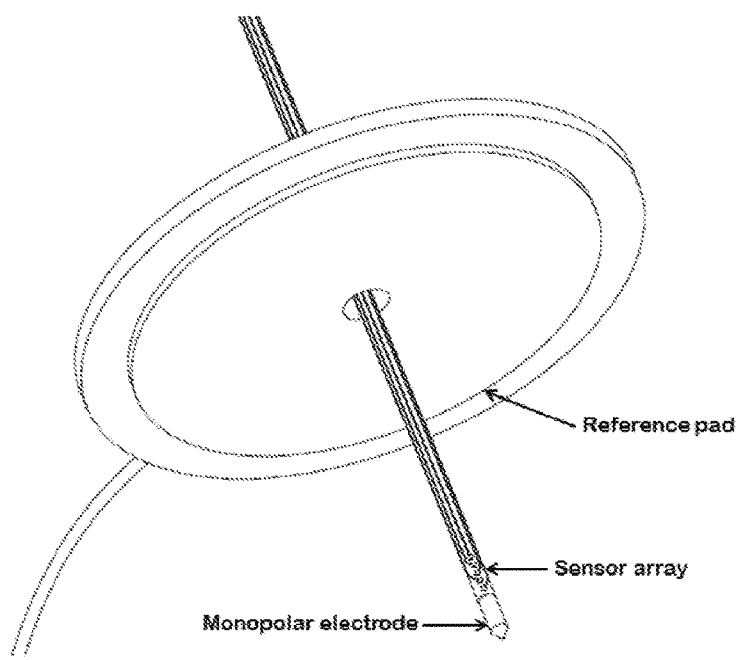
FIG. 34 shows an embodiment of a system where a monopolar electrode and a grounding pad are used to deliver the high voltage pulses.
Figure 35:
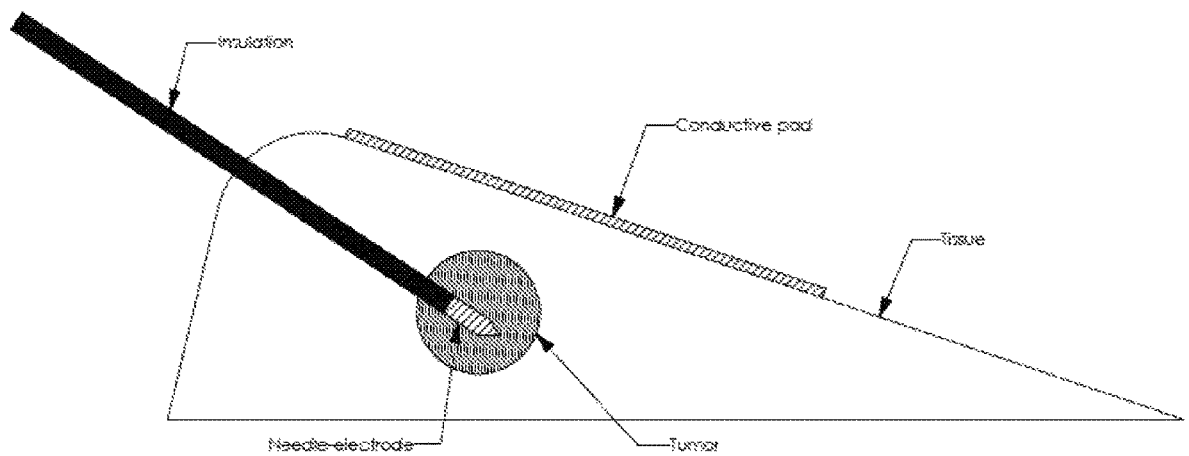
FIG. 35 shows another embodiment of a system where a monopolar electrode and a grounding pad are used to deliver the high voltage pulses.

FIGS. 34 and 35 demonstrate additional embodiments of a system configured to monitor a lesion/treated area front in real-time. In this embodiment, the high voltage energy for tissue ablation can be delivered to the tissue through a single high voltage probe and a large grounding pad, which can be positioned on the surface of the organ/tissue. Due to electric field concentration around the tip of the high voltage electrode, a spherical lesion can form. The spherical lesion can be monitored using the conductivity sensor as described before.

We claim:

1. A system comprising:
   an electrical conductivity probe, wherein the electrical conductivity probe comprises:
      an elongated member;
      an electrical conductivity sensor comprising;
      an impedance sensor, where the impedance sensor is configured to measure a low-frequency and a high-frequency impedance; and
      a substrate, where the impedance sensor is coupled to the substrate, wherein the electrical conductivity sensor is removably coupled to the elongated member;
   a treatment probe configured to deliver an energy to a tissue, where the energy is sufficient to disrupt a cell membrane;
   an impedance analyzer, where the impedance analyzer is coupled to the electrical conductivity probe;
   a low voltage power supply, where the low voltage power supply is coupled to the electrical conductivity probe and is configured to deliver a low voltage energy to the electrical conductivity probe;
   a waveform generator, where the waveform generator is coupled to the low voltage power supply;
   a gate driver, where the gate driver is coupled to the waveform generator and the low voltage power supply;
   a high voltage switch, where the high voltage switch is coupled to the treatment probe and the impedance analyzer; and
   a high voltage power supply, where the high voltage power supply is coupled to the high voltage switch.

2. The system of claim 1, further comprising a computer, wherein the computer is coupled to the impedance analyzer and wherein the computer comprises processing logic configured to determine a position of a lesion or treated area front within a tissue undergoing focal ablation/cell membrane disruption therapy.

3. The system of claim 2, wherein the processing logic is further configured to generate a signal to a user when the position of the lesion or treated area front has reached a predetermined position within the tissue.

4. The system of claim 2, wherein the processing logic is further configured to automatically manipulate the system to adjust or stop treatment of the tissue by the treatment probe when the position of the lesion or treated area front has reached a predetermined position within the tissue.

5. The system of claim 2, wherein the treatment probe is coupled with a grounding pad configured to be located elsewhere in or on a body of a subject being treated.

6. The system of claim 1, wherein the treatment probe and the electrical conductivity probe are probe regions on the same probe.

7. A method of monitoring a lesion, a treated area front, or a size thereof during focal ablation or cell membrane disruption therapy, the method comprising:
   inserting the electrical conductivity probe of the system of claim 1, into a tissue;
   inserting the treatment probe of the system of claim 1, into the tissue;
   applying a treatment to the tissue, wherein the treatment comprises applying said energy to the tissue via the treatment probe;
   measuring a characteristic of the tissue continuously during the treatment; and
   detecting a change in the tissue characteristic;
   wherein the electrical conductivity probe comprises an impedance sensor array comprising two or more impedance sensors, said two or more impedance sensors include said impedance sensor, and further comprising the step of determining the location of the lesion, or the treated area front or the size thereof by comparing impedance data between the two or more impedance sensors of the impedance sensor array.

8. The method of claim 7, wherein the tissue characteristic is impedance.

9. The method of claim 7, wherein the step of measuring comprises measuring both low-frequency impedance and high-frequency impedance and further comprising, determining that the low-frequency impedance is equal to the high frequency impedance; and further comprising the step of stopping the treatment.

10. The method of claim 7, wherein the tissue characteristic is pH, temperature, a gas concentration, a chemical concentration, a nucleic acid concentration, or a combination thereof.

11. The method of claim 7, wherein the change in the tissue characteristic is detected and further comprising the step of stopping the applied treatment.

12. The method of claim 7, wherein the change in the tissue characteristic is detected and further comprising the step of alerting a user of the detected change in the tissue characteristic.

13. The method of claim 7, further comprising the step of comparing the lesion or the treated area front, or size thereof to a threshold value and stopping the applied treatment when the lesion or the treated area front or size is greater than or equal to the threshold value.

14. The method of claim 7, further comprising the step of comparing the lesion or the treated area front, or size thereof to a threshold value and alerting a user when the lesion or the treated area front or size is greater than or equal to the threshold value.

15. The method of claim 7, further comprising the steps of comparing measured changes in impedance to a solution for an electric field distribution during focal ablation or cell membrane disruption and determining a 2D/3D lesion or a 2D/3D treated area geometry of the lesion or the treated area front.

16. The method of claim 15, further comprising the step of overlaying the 2D/3D lesion or treated area geometry on one or more medical images of a subject to generate an image overlay.

17. The method of claim 16, further comprising the step of visualizing migration, growth, or both of the lesion or the treatment area front from the image overlay.

* * * * *

UNITED STATES PATENT AND TRADEMARK OFFICE
CERTIFICATE OF CORRECTION

| | |
|---|---|
| PATENT NO. | : 10,694,972 B2 |
| APPLICATION NO. | : 15/536333 |
| DATED | : June 30, 2020 |
| INVENTOR(S) | : Rafael Davalos et al. |

It is certified that error appears in the above-identified patent and that said Letters Patent is hereby corrected as shown below:

In the Specification

Column 1, Line 22: delete "IIP-1026421" and replace with --IIP-1346343--

Signed and Sealed this
Thirteenth Day of June, 2023

Katherine Kelly Vidal
*Director of the United States Patent and Trademark Office*